(12) United States Patent
Chau et al.

(10) Patent No.: US 9,913,717 B2
(45) Date of Patent: Mar. 13, 2018

(54) PERCUTANEOUS LEAFLET AUGMENTATION

(71) Applicant: Edwards Lifesciences Corporation, Irvine, CA (US)

(72) Inventors: Mark Chau, Aliso Viejo, CA (US); David M. Taylor, Lake Forest, CA (US); Alexander J. Siegel, Costa Mesa, CA (US); Stanton J. Rowe, Newport Coast, CA (US); Bao Khuu, Irvine, CA (US); Yoon H. Kwon, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 168 days.

(21) Appl. No.: 14/622,460

(22) Filed: Feb. 13, 2015

(65) Prior Publication Data
US 2015/0230919 A1    Aug. 20, 2015

Related U.S. Application Data

(60) Provisional application No. 61/940,042, filed on Feb. 14, 2014.

(51) Int. Cl.
*A61F 2/24* (2006.01)
*A61B 17/04* (2006.01)
*A61B 17/00* (2006.01)

(52) U.S. Cl.
CPC .......... *A61F 2/246* (2013.01); *A61B 17/0487* (2013.01); *A61F 2/2409* (2013.01);
(Continued)

(58) Field of Classification Search
CPC ........ A61F 2210/0014; A61F 2250/098; A61F 220/0016; A61F 2/2427; A61F 2/2454;
(Continued)

(56) References Cited

U.S. PATENT DOCUMENTS

| 8,758,431 B2 | 6/2014 | Orlov et al. |
| 8,888,843 B2 | 11/2014 | Khairkhahan et al. |

(Continued)

FOREIGN PATENT DOCUMENTS

WO    2013036742 A1    3/2013

OTHER PUBLICATIONS

Int'l Search Report dated May 1, 2015 for PCT/US2015/015951.
U.S. Office Action and Partial Supplementary Search Report issued for EP 15749188.7-1651 dated Aug. 21, 2017.

*Primary Examiner* — Christopher L Templeton
*Assistant Examiner* — George J Ulsh
(74) *Attorney, Agent, or Firm* — Klarquist Sparkman, LLP

(57) ABSTRACT

In a representative embodiment, an implantable prosthetic heart valve device comprises an elongated body having first and second end portions, the body being configured to be implanted around a native leaflet of a heart valve such that the first end portion is on an atrial side of the leaflet and the second end portion is on a ventricular side of the leaflet and such that the body can coapt with and move away from an opposing native leaflet during operation of the heart valve. The device can further comprises a fastener configured to be mounted on a suture that extends from one of the first or second end portions, through the native leaflet and through the other of the first or second end portions such that the body is secured to the native leaflet.

12 Claims, 50 Drawing Sheets

(52) U.S. Cl.
CPC .......... *A61F 2/2412* (2013.01); *A61F 2/2457* (2013.01); *A61F 2/2463* (2013.01); *A61F 2/2466* (2013.01); *A61B 2017/00243* (2013.01); *A61B 2017/0488* (2013.01)

(58) Field of Classification Search
CPC ...... A61F 2/246; A61F 2/2463; A61F 2/2466; A61F 2/2442; A61B 17/064; A61B 2017/0649
USPC ........................................................ 623/2.11
See application file for complete search history.

(56) References Cited

U.S. PATENT DOCUMENTS

| | | |
|---|---|---|
| 2005/0159810 A1 | 7/2005 | Filsoufi |
| 2005/0216039 A1 | 9/2005 | Lederman |
| 2009/0043381 A1* | 2/2009 | Macoviak ........ A61B 17/00234 623/2.36 |
| 2010/0204662 A1 | 8/2010 | Orlov et al. |
| 2010/0298929 A1 | 11/2010 | Thornton et al. |
| 2013/0211513 A1 | 8/2013 | Rourke et al. |
| 2014/0171984 A1 | 6/2014 | Hillukka |
| 2014/0309727 A1 | 10/2014 | Lamelas et al. |

* cited by examiner

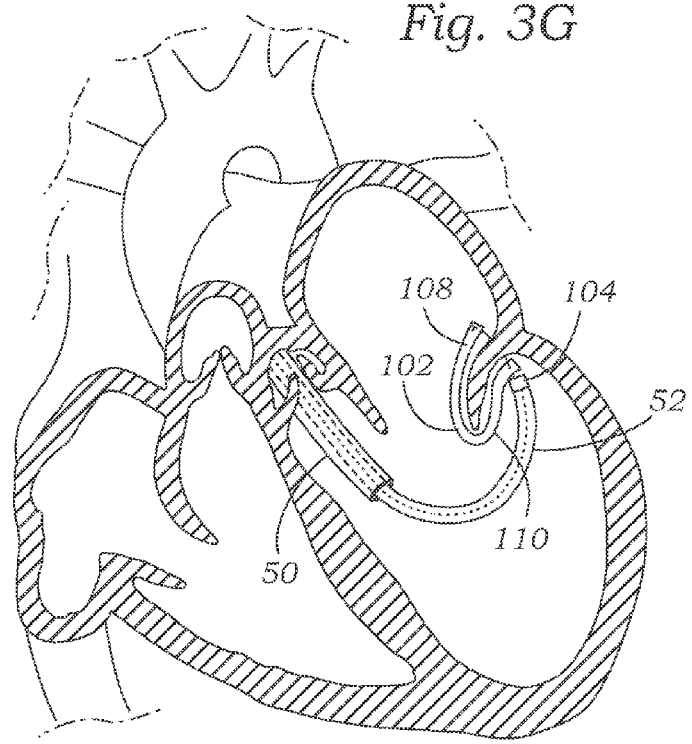
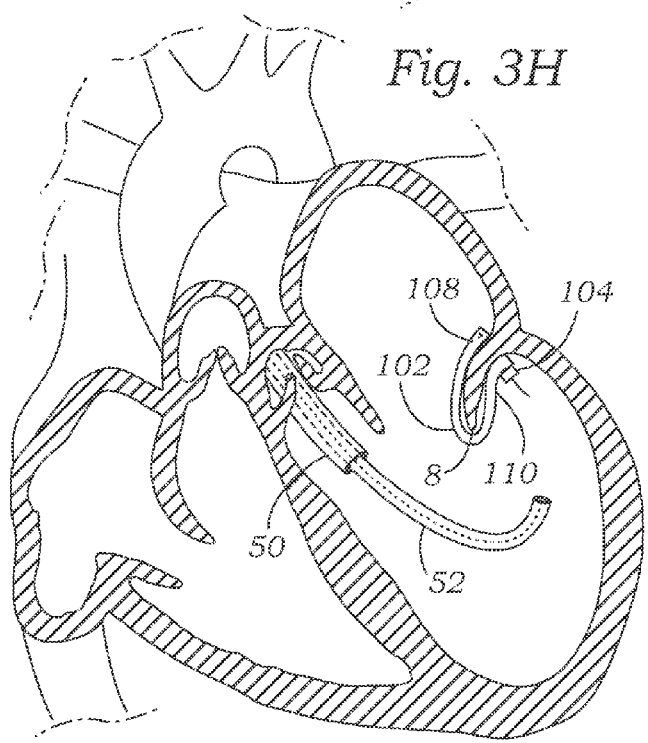

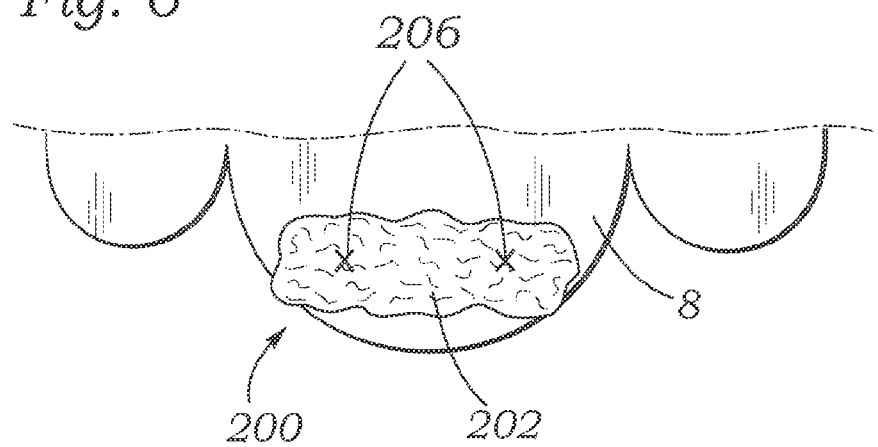
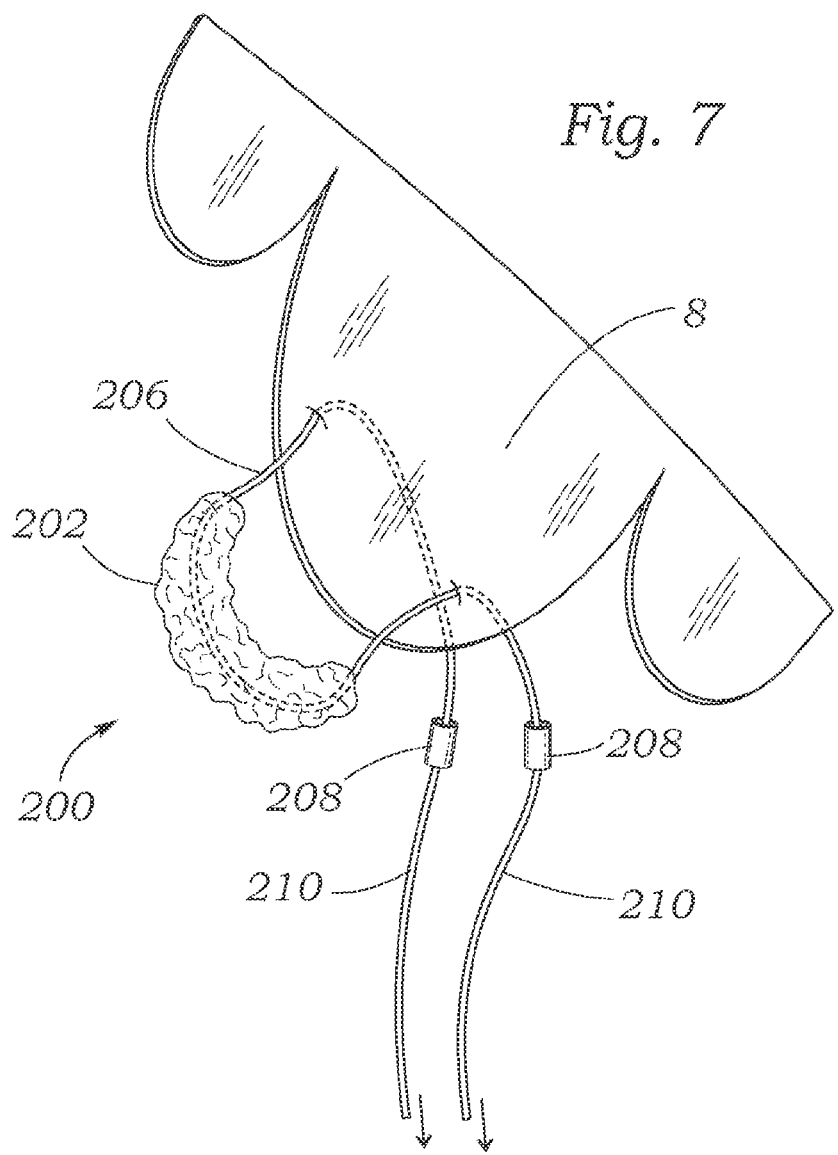

Fig. 13A
Fig. 13B
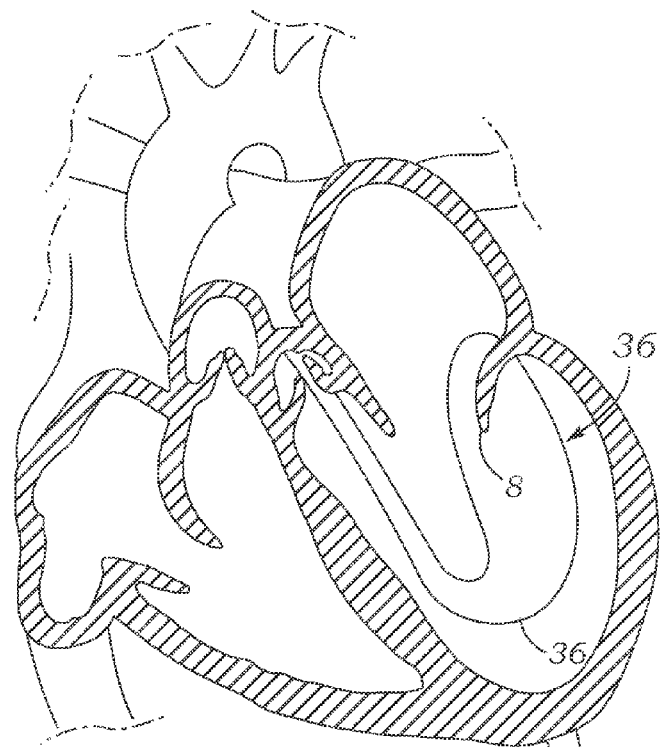
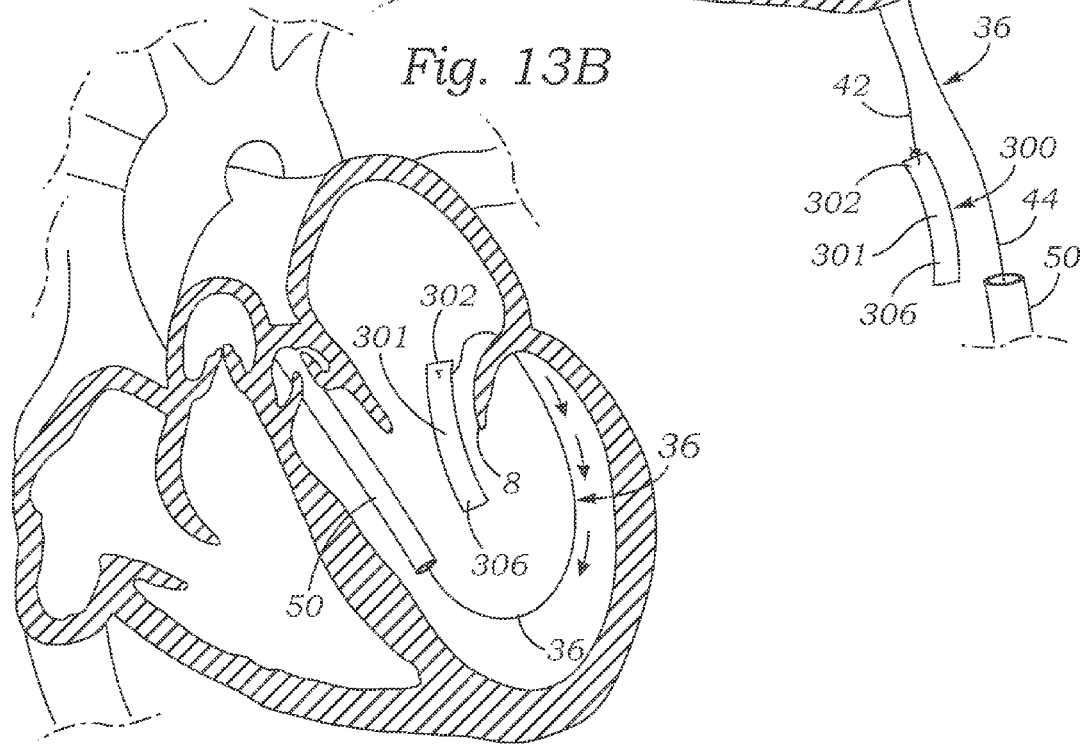

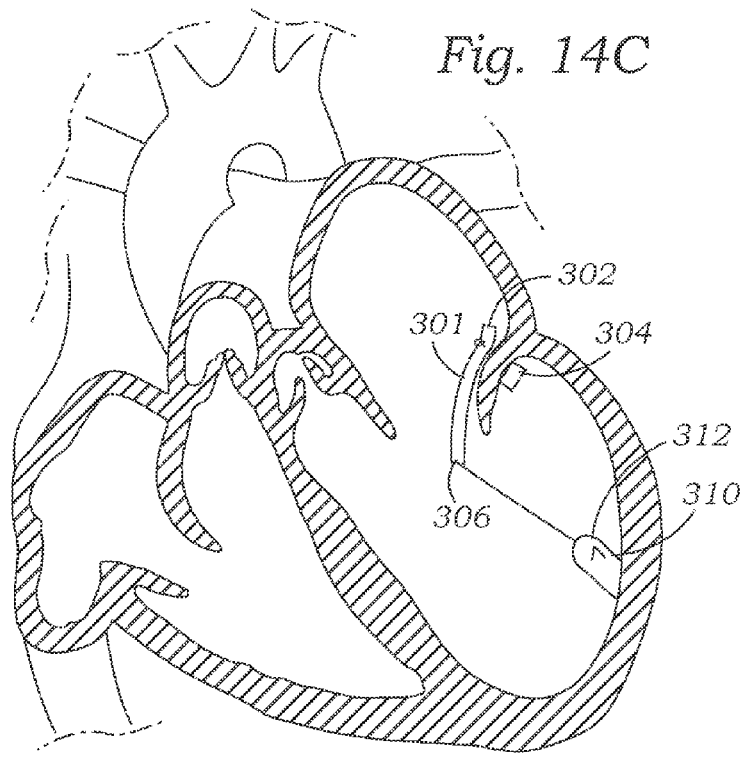
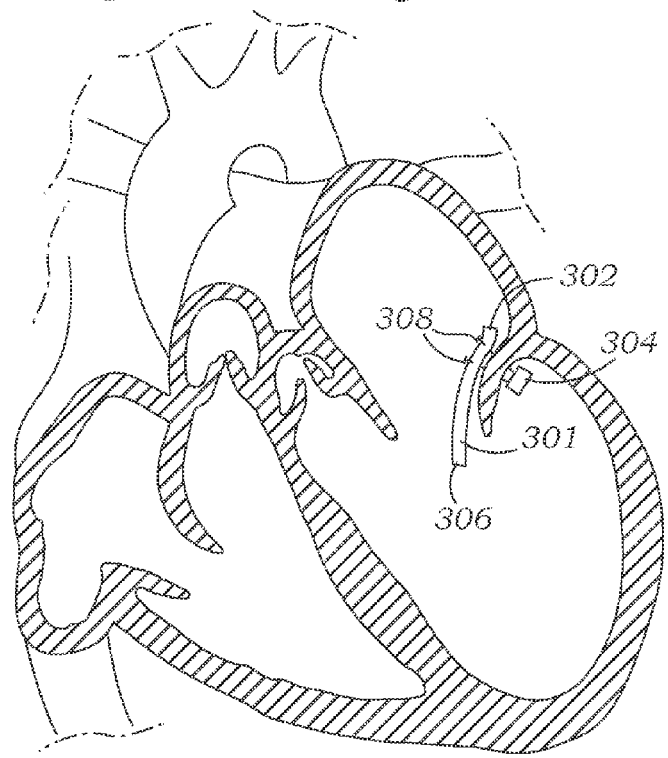

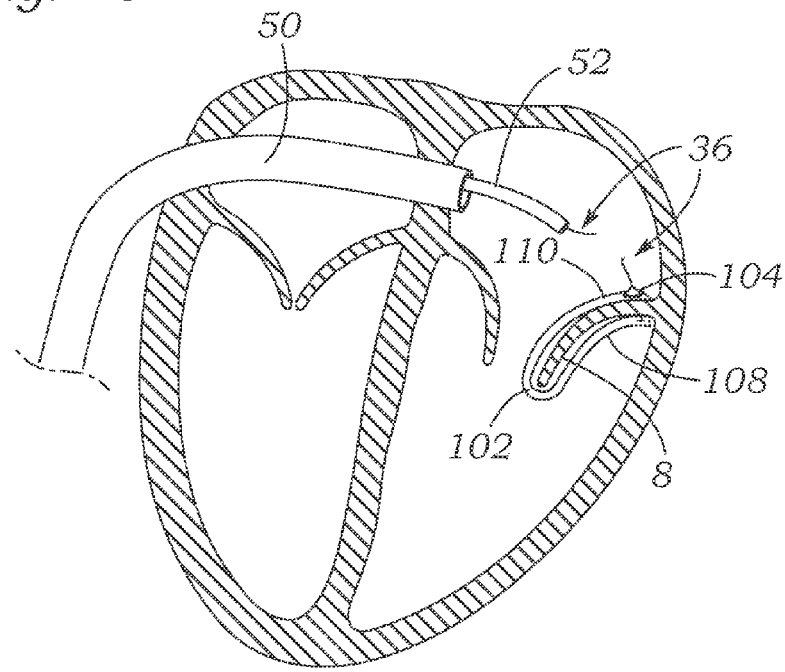
Fig. 18E
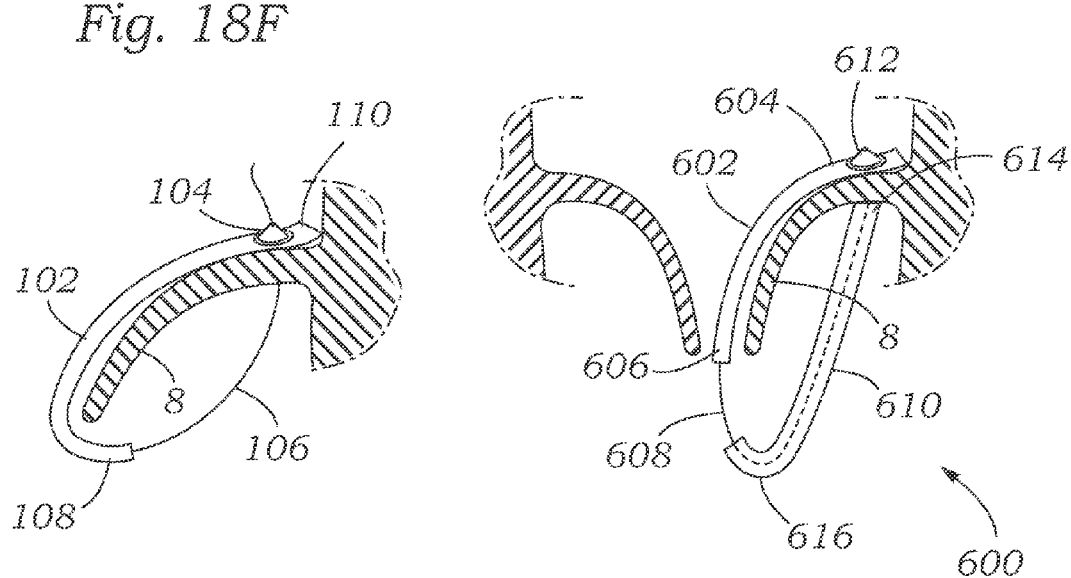
Fig. 18F
Fig. 19

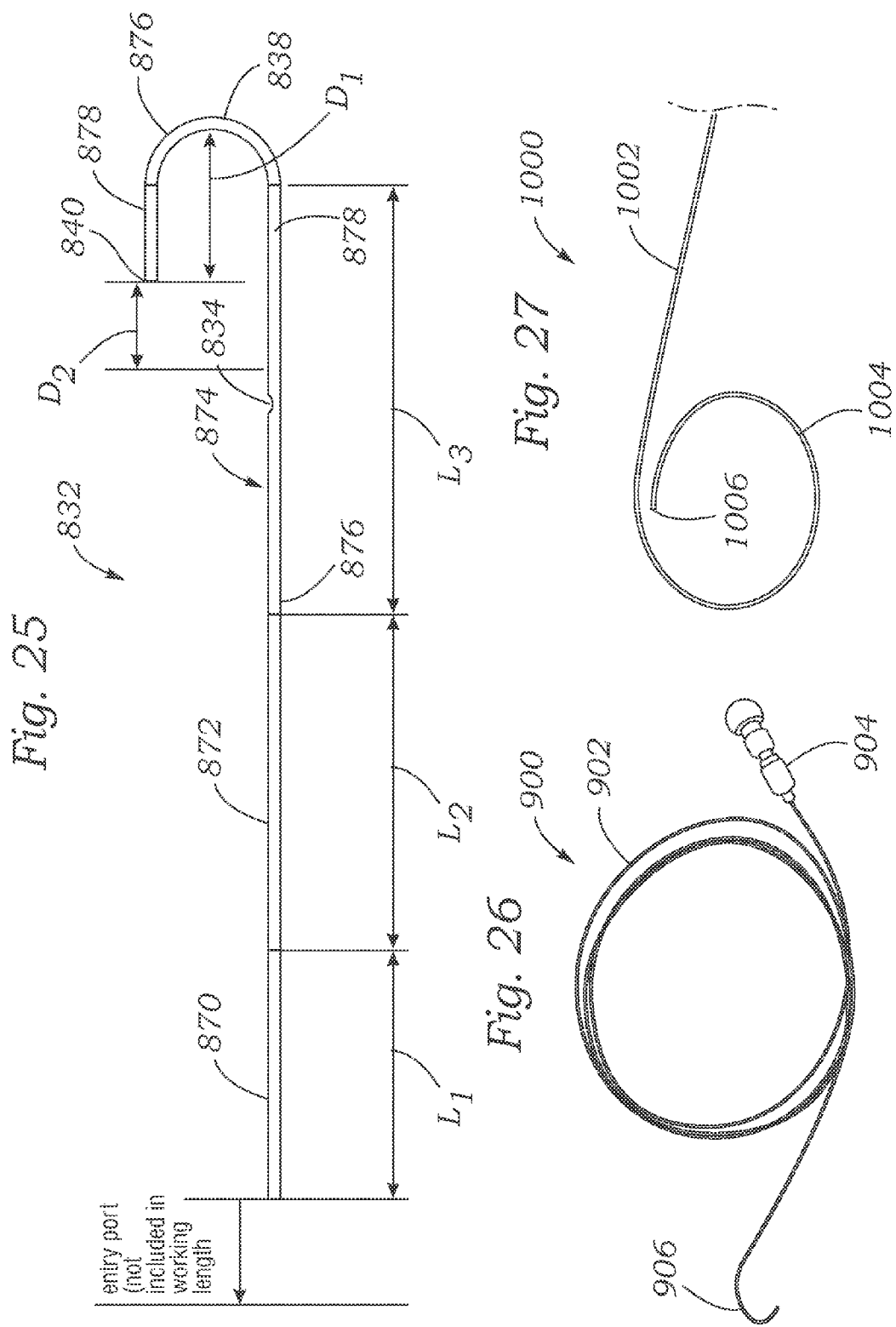

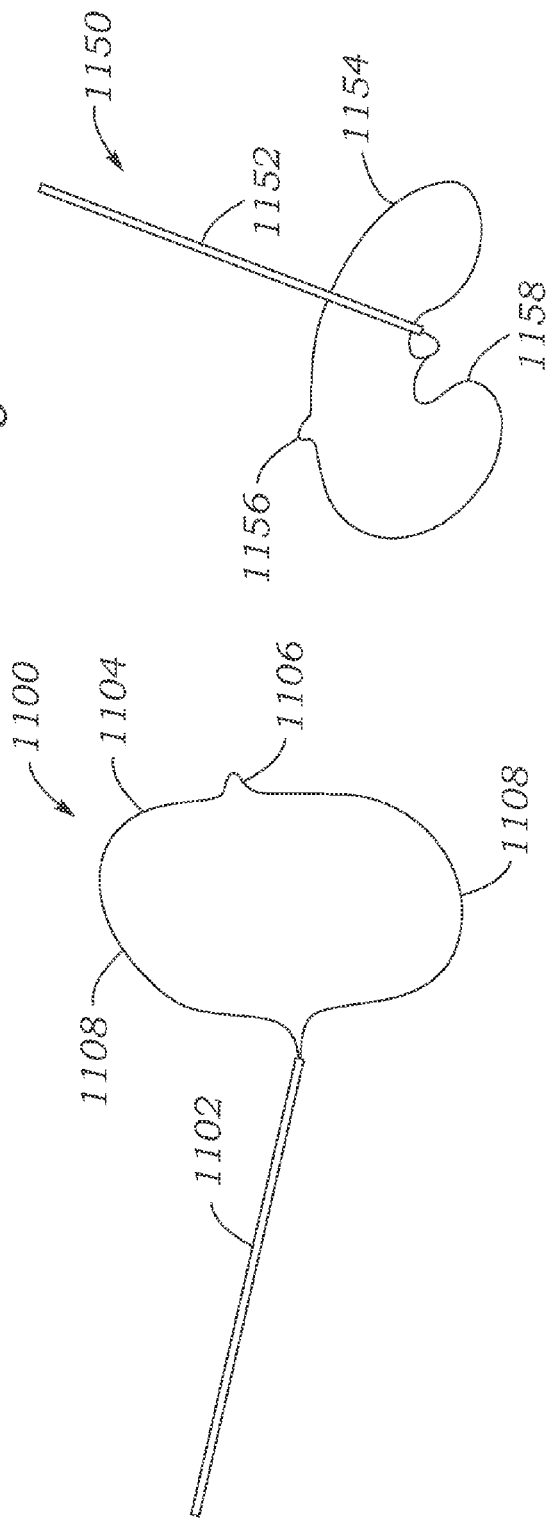
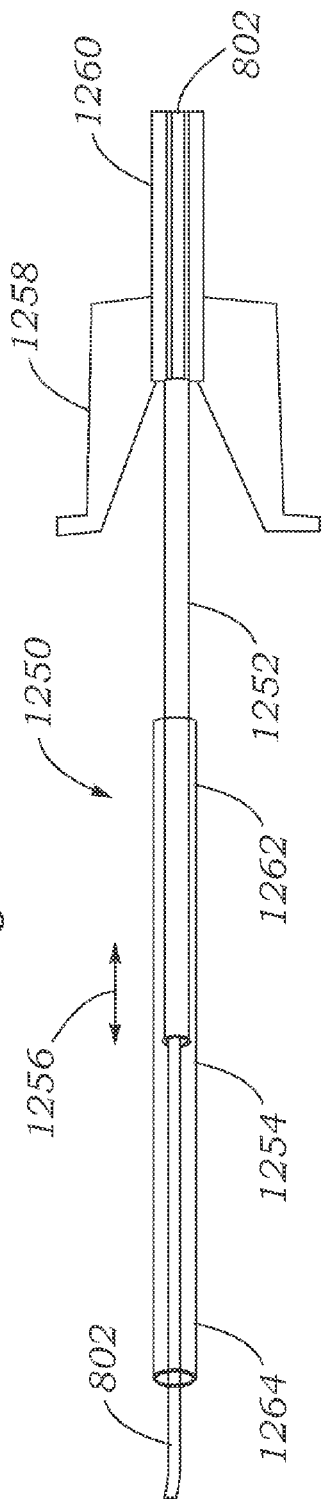

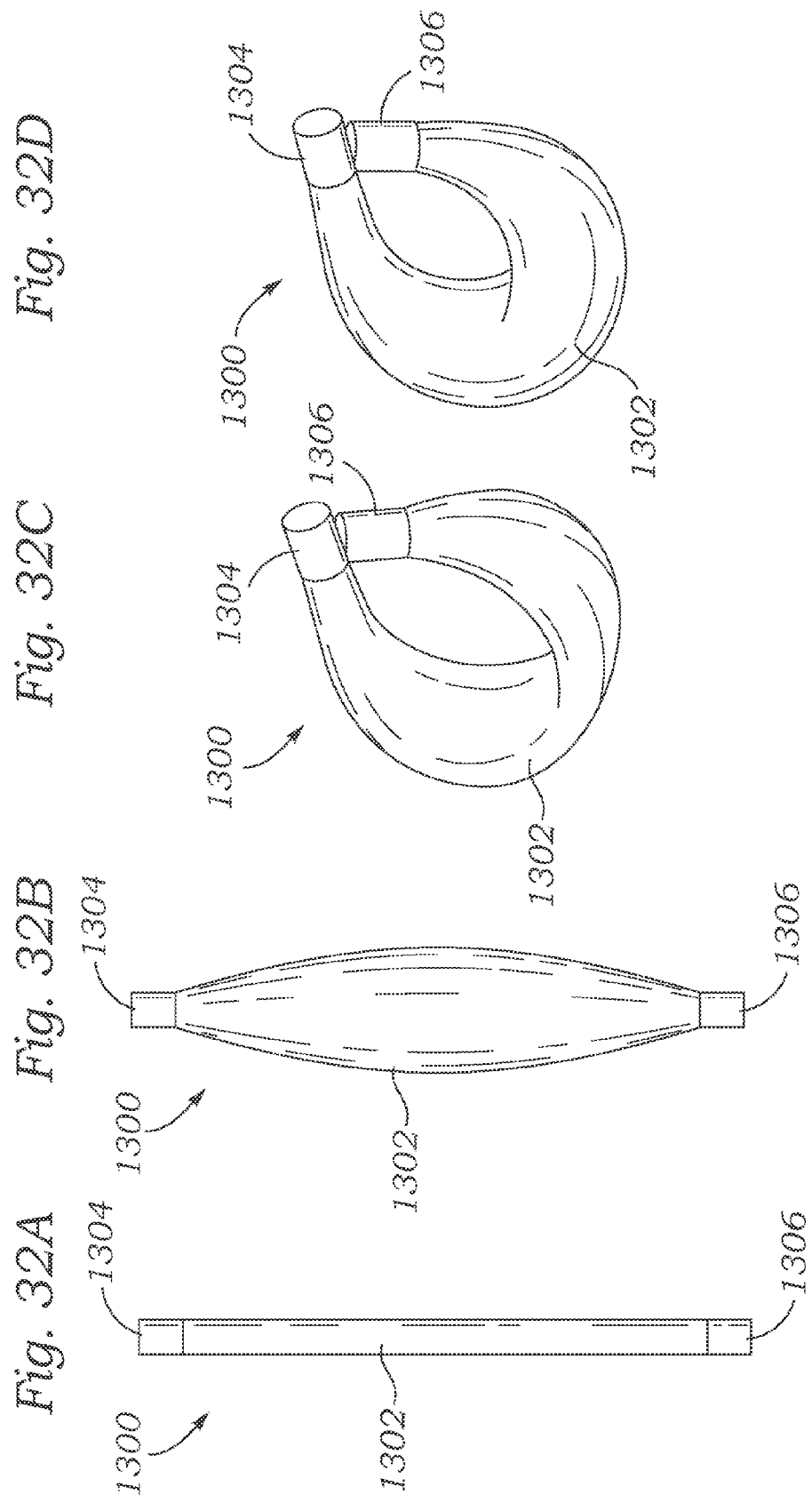

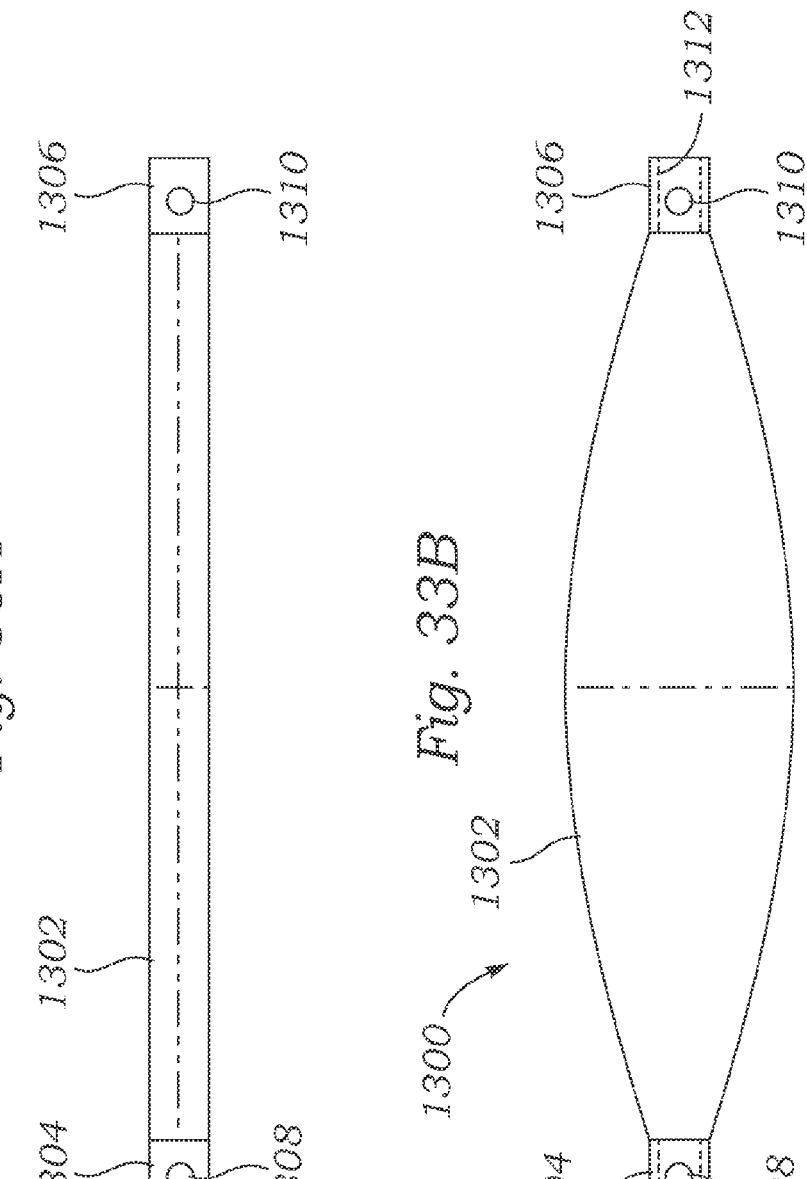
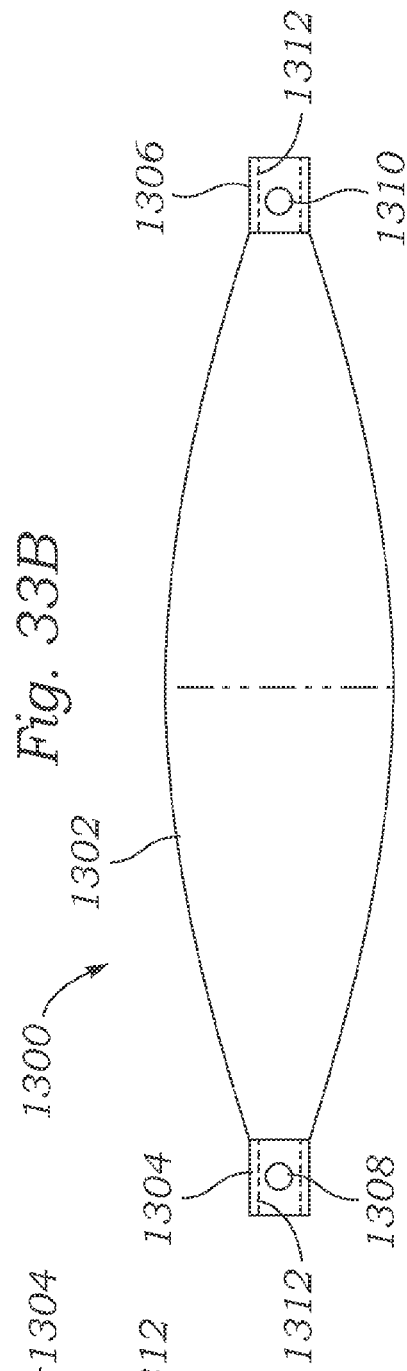
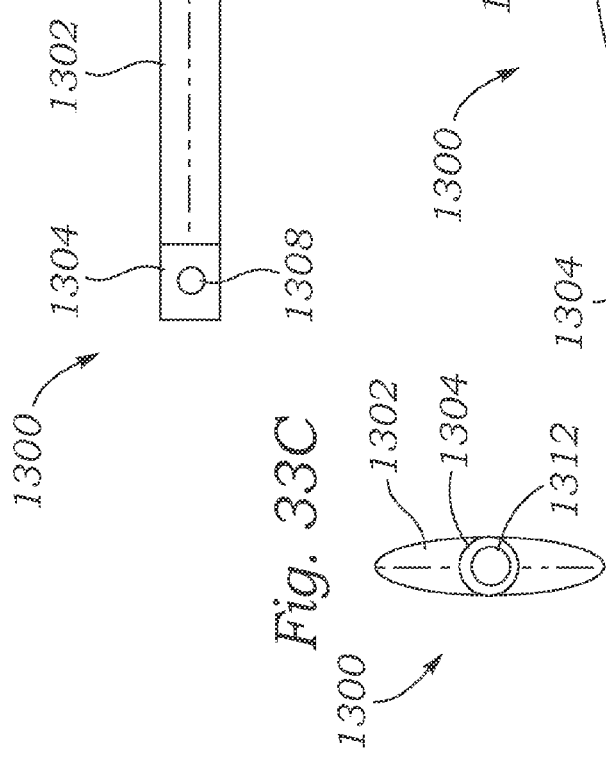

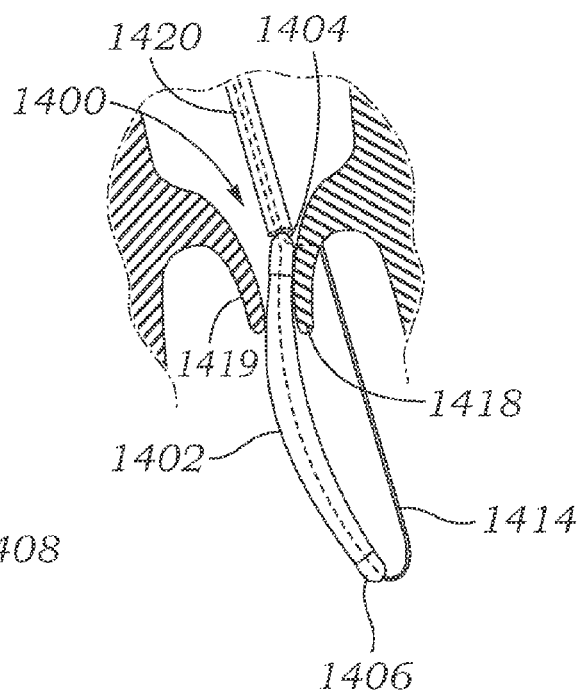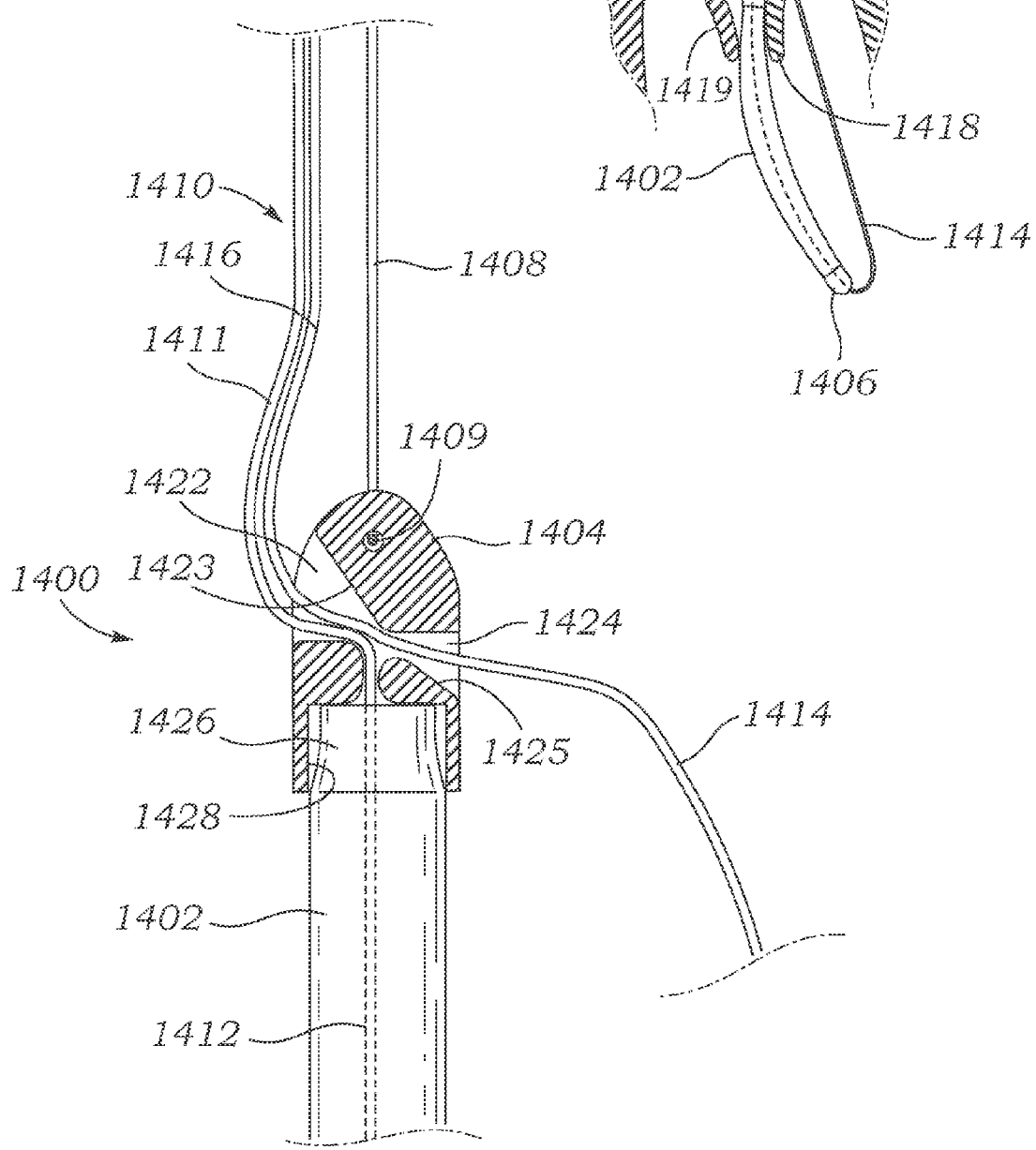

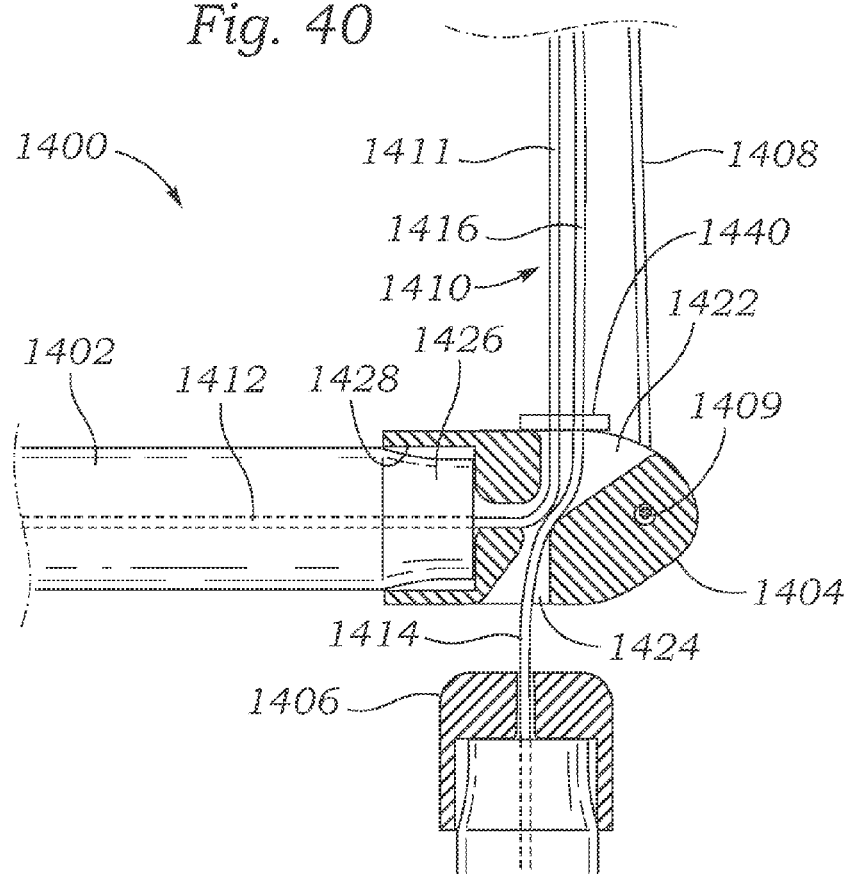
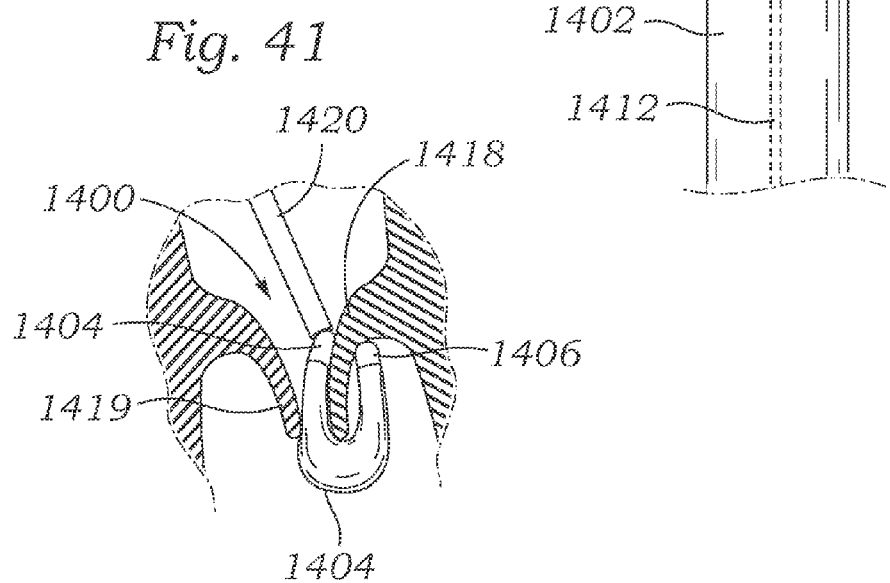

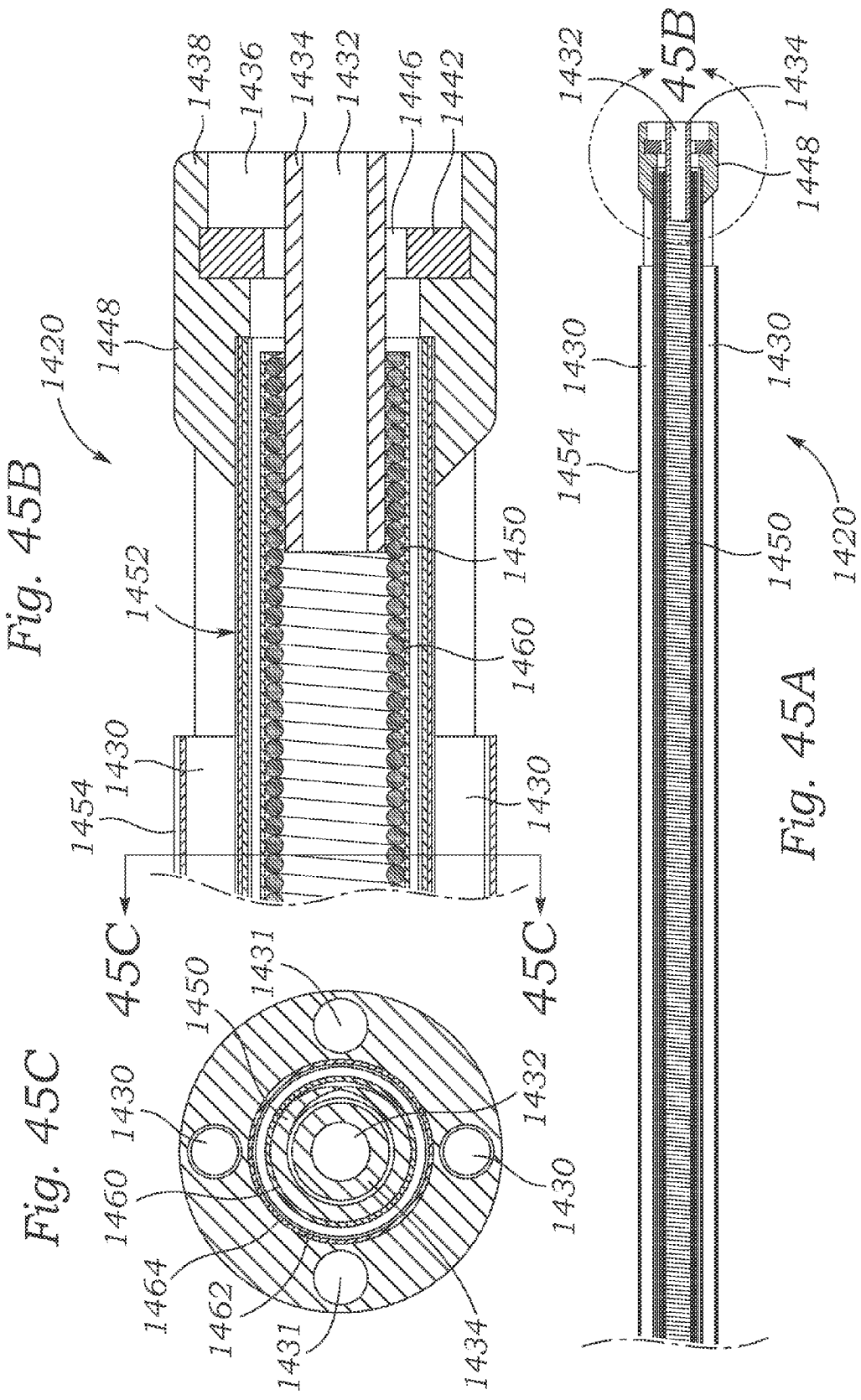

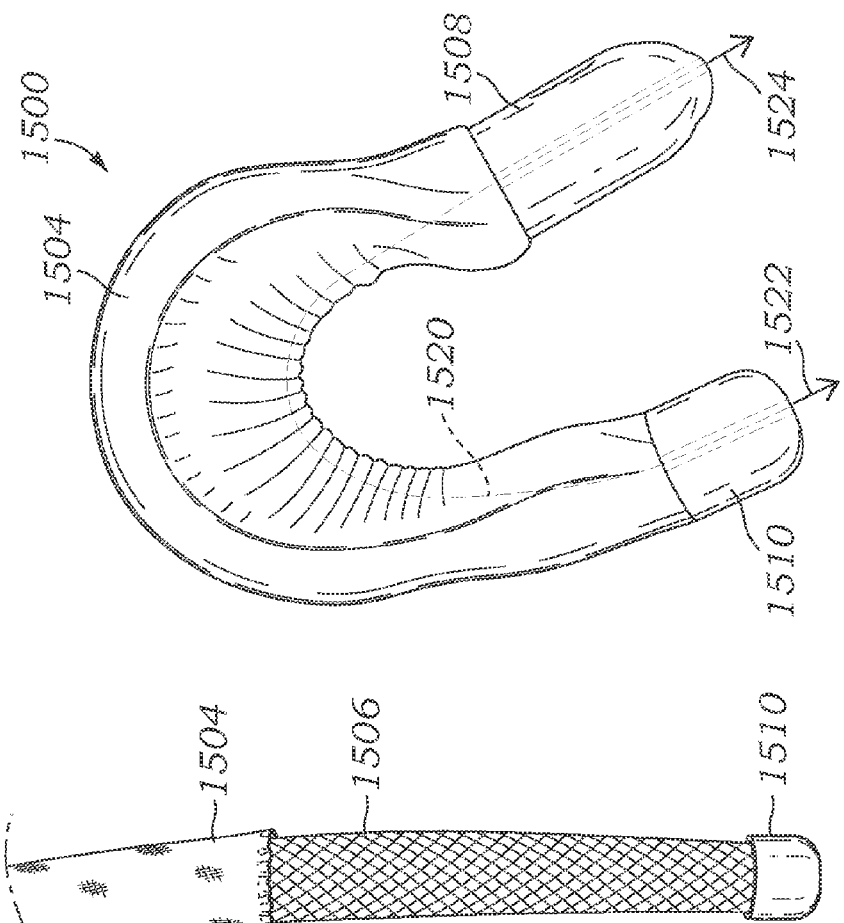
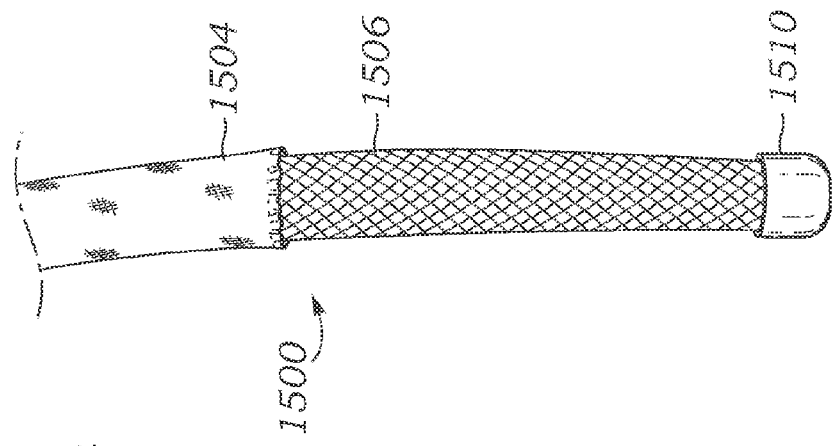
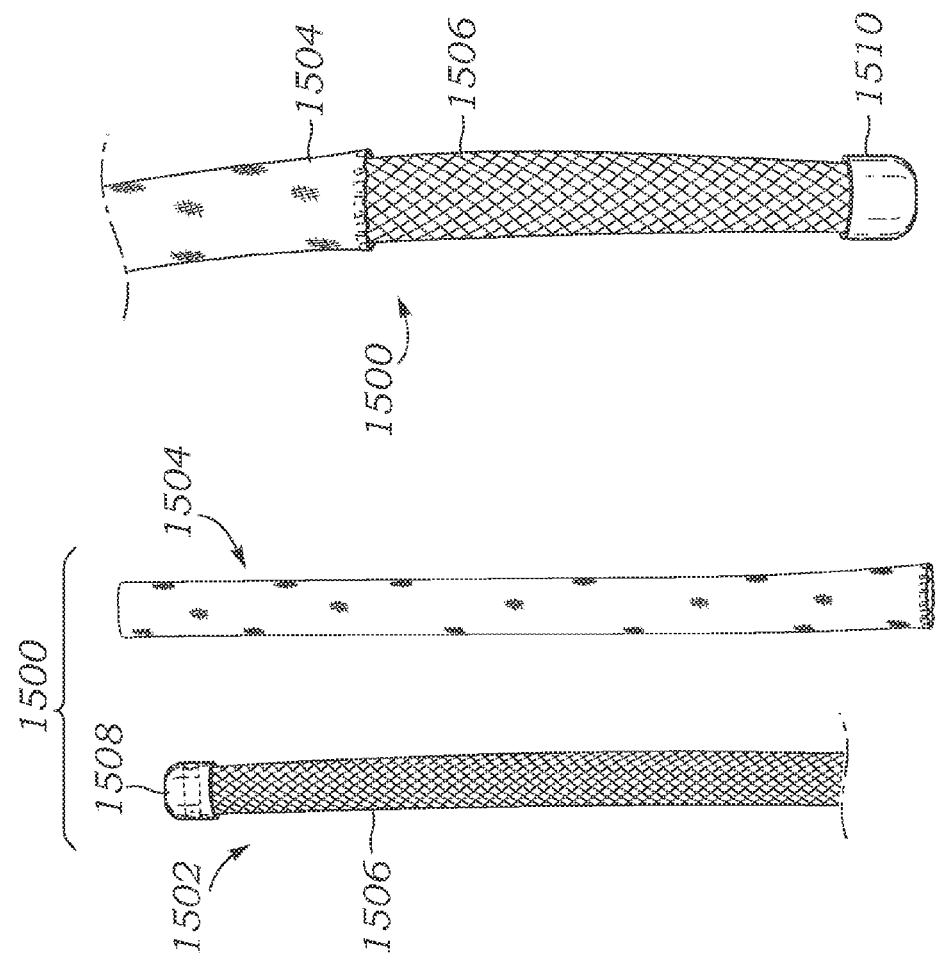

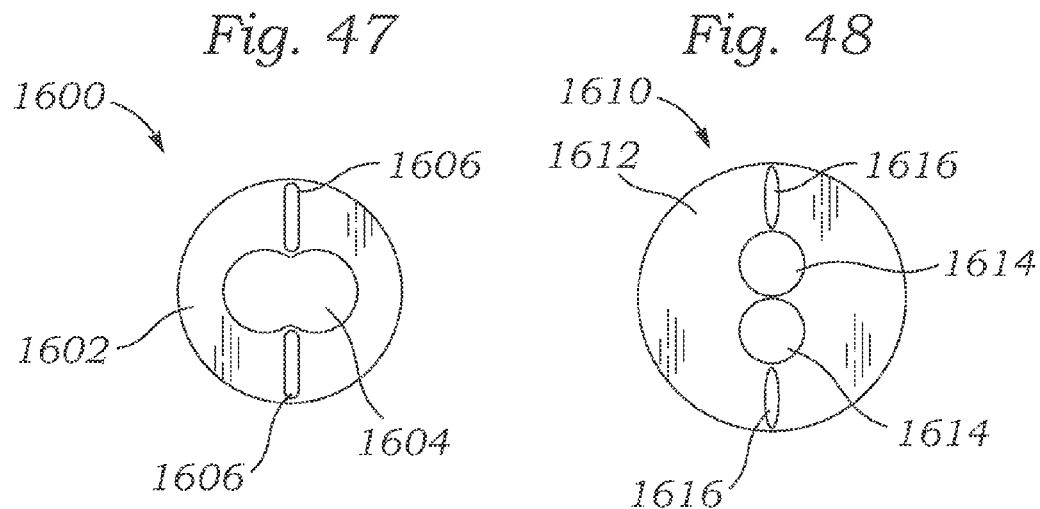
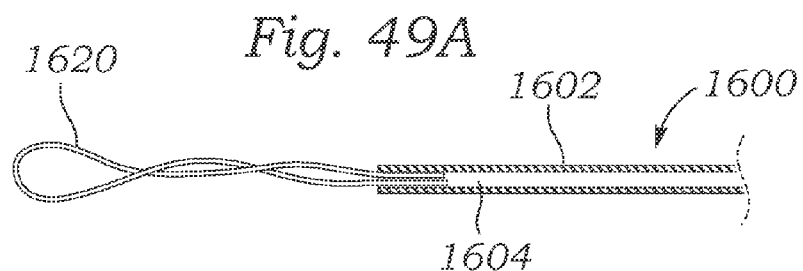
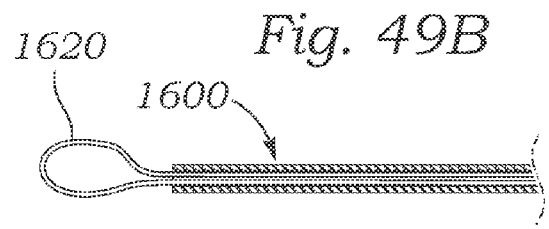
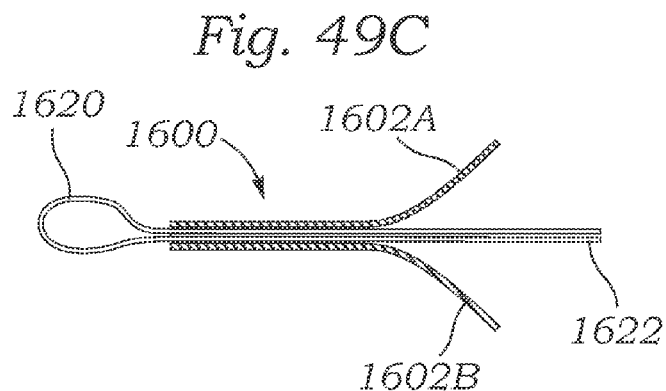

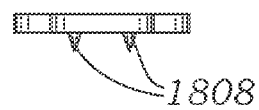
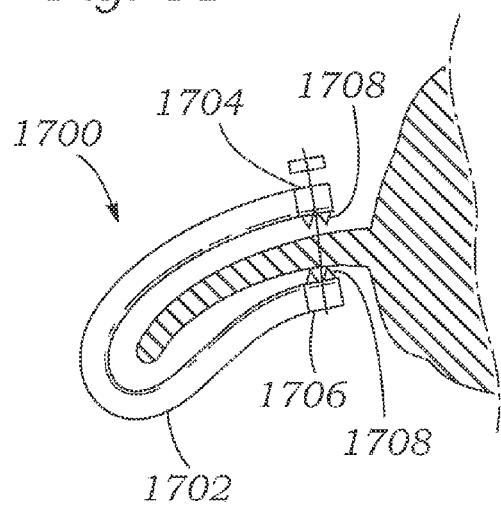
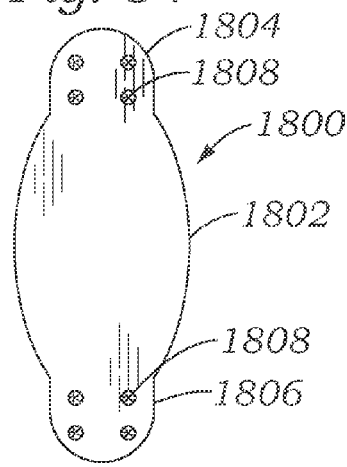
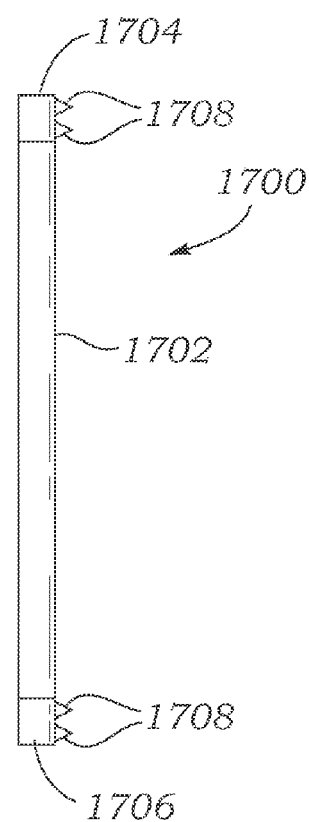
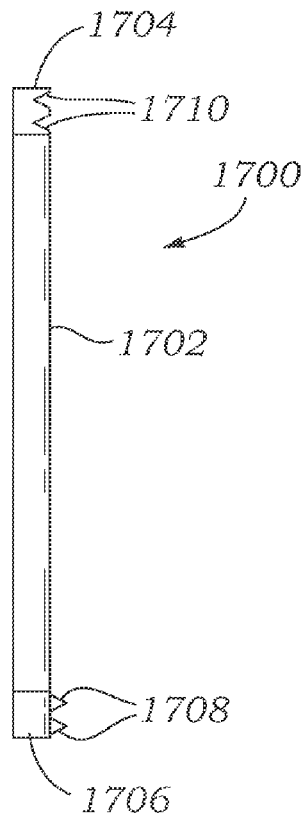

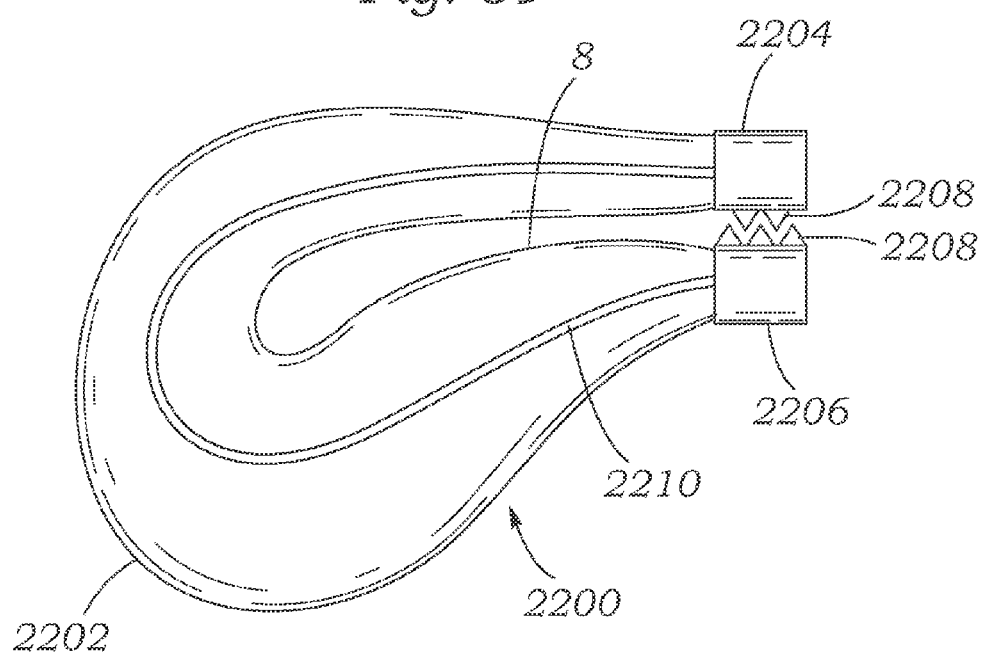

PERCUTANEOUS LEAFLET AUGMENTATION

CROSS-REFERENCE TO RELATED APPLICATION

The present application claims the benefit of U.S. Provisional Application No. 61/940,042, filed Feb. 14, 2014, which is incorporated herein by reference.

FIELD

This disclosure pertains generally to prosthetic devices and related methods for helping to seal native heart valves and prevent or reduce regurgitation therethrough, as well as devices and related methods for implanting such prosthetic devices.

BACKGROUND

The native heart valves (i.e., the aortic, pulmonary, tricuspid, and mitral valves) serve critical functions in assuring the forward flow of an adequate supply of blood through the cardiovascular system. These heart valves can be rendered less effective by congenital malformations, inflammatory processes, infectious conditions, or disease. Such damage to the valves can result in serious cardiovascular compromise or death. For many years the definitive treatment for such disorders was the surgical repair or replacement of the valve during open-heart surgery. However, such surgeries are highly invasive and are prone to many complications. Therefore, elderly and frail patients with defective heart valves often went untreated. More recently, transvascular techniques have been developed for introducing and implanting prosthetic devices in a manner that is much less invasive than open-heart surgery. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets extending downward from the annulus into the left ventricle. The mitral valve annulus can form a D-shaped, oval, or otherwise out-of-round cross-sectional shape having major and minor axes. The anterior leaflet can be larger than the posterior leaflet, forming a generally C-shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates, the oxygenated blood that is collected in the left atrium flows into the left ventricle. When the muscles of the left atrium relax and the muscles of the left ventricle contract, the increased blood pressure in the left ventricle urges the two leaflets of the mitral valve together, thereby closing the one-way mitral valve so that blood cannot flow back into the left atrium and is, instead, expelled out of the left ventricle through the aortic valve. To prevent the two leaflets from prolapse under pressure and folding back through the mitral valve annulus towards the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systole phase of the cardiac cycle. Mitral regurgitation is the most common form of valvular heart disease. Mitral regurgitation has different causes, such as leaflet prolapse, dysfunctional papillary muscles, and/or stretching of the mitral valve annulus resulting from dilation of the left ventricle. Mitral regurgitation at a central portion of the leaflets can be referred to as central jet mitral regurgitation, and mitral regurgitation nearer to one commissure (i.e., location where the leaflets meet) of the leaflets can be referred to as eccentric jet mitral regurgitation.

Some prior techniques for treating mitral regurgitation include stitching portions of the native mitral valve leaflets directly to one another. Other prior techniques include the use of a body implanted between the native mitral valve leaflets. Despite these prior techniques, there is a continuing need for improved devices and methods for treating mitral valve regurgitation.

SUMMARY

This disclosure pertains generally to prosthetic devices and related methods for helping to seal native heart valves, and for preventing or reducing regurgitation therethrough, as well as devices and related methods for implanting such prosthetic devices.

In particular embodiments, the prosthetic device can comprise a body and a fastener. The body can be a relatively thin piece of material that effectively extends the length and/or width of the native leaflet to which it is attached. In other embodiments, the body can have sufficient thickness to function as a spacer that is configured to fill the gap along the coaptation line of the native leaflets. In still other embodiments, the body can be retained in a collapsed delivery state inside a delivery catheter during transvascular delivery through a patient's body to the heart and can expand when deployed from the delivery catheter. In some embodiments, the body also can be configured to expand radially or laterally to increase the width or diameter of the body after deployment from a delivery catheter, such as by tensioning a suture extending through the body.

In some embodiments, the body is sufficiently thick to function as a spacer, while also able to effectively extend the length and/or width of the native leaflet. The body can be positioned within the native valve orifice to help create a more effective seal between the native leaflets to prevent or minimize mitral regurgitation. The body can comprise a structure that is impervious to blood and that allows the native leaflets to close around the body during ventricular systole to block blood from flowing from the ventricle back into the atrium. The body can fill a gap between improperly functioning native leaflets that do not naturally close completely.

In some embodiments, the body can effectively extend the leaflet(s) and/or prevent prolapse of the leaflet(s). In some embodiments, the body covers a large area of an atrial and/or ventricular surface of the leaflet, such as substantially the entire atrial surface, while in other embodiments it covers a smaller area. In some embodiments, the body, in particular, covers the P2 portion of the posterior leaflet of the mitral valve. The body can cover the entire length of the coaptation line, or a portion thereof. In some embodiments, the body covers the length of the coaptation line adjacent to the P2 portion of the posterior leaflet.

The body can have various shapes. In some embodiments, the body can have an elongated cylindrical shape having a round cross-sectional shape. In other embodiments, the body can have an oval cross-sectional shape, a rectangular or other polygonal cross-sectional shape, a crescent cross-sectional shape, or various other non-cylindrical shapes. In some embodiments, the body can be substantially flat. The body can have an atrial or upper end positioned in or adjacent to an atrium (such as the left atrium), a ventricular or lower end positioned in or adjacent to a ventricle (such as the left ventricle), and a surface that extends between the native valve leaflets (such as between the native mitral valve leaflets).

The fastener can be configured to secure the device to one or both of the native leaflets such that the body is positioned between two native leaflets. The fastener can attach to the body at a location adjacent the ventricular end of the body and/or to a location adjacent the atrial end of the body. The fastener can be configured to be positioned behind a native leaflet when implanted such that the leaflet is captured between the anchor and at least a portion of the body.

Some embodiments disclosed herein are generally configured to be secured to only one of the native mitral leaflets (the posterior or anterior leaflet). However, in other embodiments, prosthetic devices can be secured to both mitral leaflets. Unless otherwise stated, any of the embodiments disclosed herein can optionally be secured to the anterior mitral leaflet and/or secured to the posterior mitral leaflet, regardless of whether any particular embodiment is shown as being secured to a particular leaflet. Moreover, any of the embodiments can be implanted on one or more native leaflets of the other valves of the heart.

Some embodiments include two or more fasteners, such as to provide additional stabilization. Unless otherwise stated, any embodiment that includes a fastener on the ventricular side can optionally include a fastener on the atrial side, regardless of whether or not the particular embodiment is shown with an atrial fastener. Likewise, any embodiment that includes a fastener on the atrial side can optionally include a fastener on the ventricular side, regardless of whether or not the particular embodiment is shown with a ventricular fastener.

By anchoring a prosthetic mitral device to one of the mitral leaflets, as disclosed herein, instead of anchoring the device to the walls of the left ventricle, to the walls of the left atrium, to the native valve annulus, and/or to the annulus connection portions of the native leaflets, the device anchorage is made independent of the motions of the ventricular walls and atrial walls, which move significantly during contraction of the heart. Anchoring to a mitral valve leaflet can provide a more stable anchorage for a prosthetic mitral device, and can eliminate the risk of hook-type or corkscrew-type anchors tearing or otherwise causing trauma to the walls of the left ventricle or left atrium. Furthermore, the device body can be held in a more consistent position with respect to the mitral leaflets as the leaflets articulate, eliminating undesirable motion imparted on the device from the contraction motions of the left ventricle walls and left atrium walls. Anchoring to a mitral leaflet can also allow for a shorter body length compared to devices having other anchorage means.

In a representative embodiment, an implantable prosthetic heart valve device comprises an elongated body having first and second end portions, the body being configured to be implanted around a native leaflet of a heart valve such that the first end portion is on an atrial side of the leaflet and the second end portion is on a ventricular side of the leaflet and such that the body can coapt with and move away from an opposing native leaflet during operation of the heart valve. The device further comprises a fastener configured to be mounted on a suture that extends from one of the first or second end portions, through the native leaflet and through the other of the first or second end portions such that the body is secured to the native leaflet.

In some embodiments, the body comprises an intermediate portion extending between the first and second end portions, the body being configured such that the intermediate portion extends beyond a free end of the native leaflet when the body is secured to the native leaflet. In some embodiments, at least one of the first and second end portions of the body comprises one or more barbs that can penetrate the native leaflet.

In some embodiments, the body of the prosthetic device comprises a tubular layer defining a lumen extending from the first end portion to the second end portion. In some embodiments, the tubular layer has a cross-sectional profile in a plane perpendicular to the length of the tubular layer, the cross-sectional profile having a major lateral dimension and minor lateral dimension that is smaller than the major lateral dimension. In some embodiments, the tubular layer comprises a tubular braided layer. In some embodiments, the braided layer comprises a first, inner braided layer and a second, outer braided layer extending over the inner braided layer, the outer braided layer being relatively less porous to blood than the inner braided layer.

In another representative embodiment, an assembly comprises an elongated flexible rail having first and second ends and a length sufficient to form a loop that extends into a patient's body and through a native leaflet of a heart valve with the first and second ends outside of the patient's body. The assembly further comprises an elongated catheter and an implantable prosthetic device configured to be implanted on the native leaflet, the prosthetic device being coupled to the rail and the catheter such that advancing the catheter along the rail is effective to advance the prosthetic device to the native leaflet. The prosthetic device can be configured such that when it is implanted on the native leaflet, the prosthetic device can coapt with and move away from an opposing native leaflet during operation of the heart valve.

In another representative embodiment, a method comprises implanting a flexible rail in the heart of a patient's body such that the rail forms a loop that extends through a leaflet of the native heart valve and first and second ends of the rail reside outside of the patient's body; coupling a prosthetic device to the rail and delivering the prosthetic device to the native leaflet via the rail; and securing the prosthetic device to the native leaflet.

In another representative embodiment, a method comprises inserting an elongated catheter into a patient's body; advancing the catheter through the patient's body into the heart; penetrating a native heart valve leaflet with a distal end portion of the catheter; inserting an elongated rail through the catheter such that a distal end of the rail extends through the native leaflet; and pulling the distal end of the rail outside of the patient's body such that the rail forms a loop extending through the native leaflet.

In another representative embodiment, an assembly comprises a first catheter configured to be inserted into a patient's body and having a distal end portion that can be guided to a position adjacent a native leaflet of a heart valve.

A second catheter is configured to extend through the first catheter and has a distal end portion configured to extend through the native leaflet. An elongated rail is configured to extend from a location outside the patient's body, through the second catheter, and through the native leaflet. A snare catheter is configured to extend through the second catheter, and comprises a snare loop at a distal end thereof configured to capture a distal end of the rail that extends through the native leaflet and retract the distal end of the rail back into the first catheter.

BRIEF DESCRIPTION OF THE DRAWINGS

FIGS. 3A-3H show the implantation of the prosthetic device of FIG. 1 being implanted along the suture shown in FIGS. 2A-2F.

FIGS. 6 and 7 show front and perspective views of a prosthetic device for treating mitral valve regurgitation, according to another embodiment.

FIGS. 13A-13D are cross sections of a heart showing another method of implanting a prosthetic device for treating mitral valve regurgitation on the posterior mitral valve leaflet.

FIGS. 14A-14E show alternative ways of securing the prosthetic device shown in FIG. 13A-13D.

FIGS. 18A-18F are cross sections of a heart showing a method of implanting a suture transseptally through the posterior mitral valve leaflet, and implanting a prosthetic device at the posterior mitral valve leaflet using the suture, according to another embodiment.

FIG. 19 a cross section of a mitral valve with a prosthetic device for treating mitral valve regurgitation with increased stiffness to aid in valve patency, according to one embodiment.

FIG. 25 is an enlarged side view of the shaft of the delivery catheter of FIG. 22.

FIG. 26 is a perspective view of an embodiment of a crossing-catheter that can be used with the delivery catheter of FIG. 22 to implant a suture rail through native valve tissue.

FIG. 27 is a perspective view of an embodiment of a needle wire for puncturing native valve tissue.

FIGS. 28 and 29 are perspective views of two different embodiments of a snare catheter that can be used with the delivery catheter of FIG. 22 when implanting a suture rail through native valve tissue.

FIG. 30 is a side view of an embodiment of a suture-feeding device that can be used to advance a suture rail through a delivery catheter.

FIGS. 32A-32D are various views of another embodiment of a prosthetic device for treating mitral valve regurgitation.

FIGS. 33A-33C are additional views of the prosthetic device shown in FIGS. 32A-32D.

FIGS. 37 and 38 are enlarged views of the proximal end portion of the prosthetic device shown in FIG. 34.

FIG. 39 is a cross sectional view of the mitral valve showing the implantation of the prosthetic device of FIG. 34.

FIG. 40 is an enlarged view of the proximal and distal end portions of the prosthetic device of FIG. 34 after the device is deployed around a native leaflet.

FIG. 41 is a cross sectional view of the mitral valve showing the prosthetic device of FIG. 34 deployed around the native posterior leaflet.

FIG. 45A is a cross sectional view of the delivery catheter of FIG. 42.

FIG. 45B is an enlarged cross sectional view of the distal end portion of the delivery catheter of FIG. 45A.

FIG. 45C is a cross sectional view of the delivery catheter of FIG. 45B taken along line FIG. 45C-45C.

FIG. 46A-46C are various views of another embodiment of a prosthetic device for treating mitral valve regurgitation.

FIGS. 47 and 48 are end views of two different embodiments of an untwisting catheter that can be used to untwist a suture rail extending into a patient's vasculature.

FIGS. 49A-49C are cross sectional views showing the use of the untwisting catheter of FIG. 47 or FIG. 48.

FIG. 50 is a side view of another embodiment of a prosthetic device for treating mitral valve regurgitation.

FIG. 51 shows the prosthetic device of FIG. 50 implanted on a native leaflet.

FIG. 52 shows a modification of the prosthetic device of FIG. 50.

FIGS. 53 and 54 are end view and bottom views, respectively, of another embodiment of a prosthetic device for treating mitral valve regurgitation.

FIG. 59 is a side view of another embodiment of a prosthetic device for treating mitral valve regurgitation.

DETAILED DESCRIPTION

Described herein are embodiments of prosthetic devices that are primarily intended to be implanted at one of the mitral, aortic, tricuspid, or pulmonary valve regions of a human heart, as well as apparatuses and methods for implanting the same. The prosthetic devices can be used to help restore and/or replace the functionality of a defective native mitral valve. The disclosed embodiments should not be construed as limiting in any way. Instead, the present disclosure is directed toward all novel and nonobvious features and aspects of the various disclosed embodiments, alone and in various combinations and sub-combinations with one another.

Figure 1:
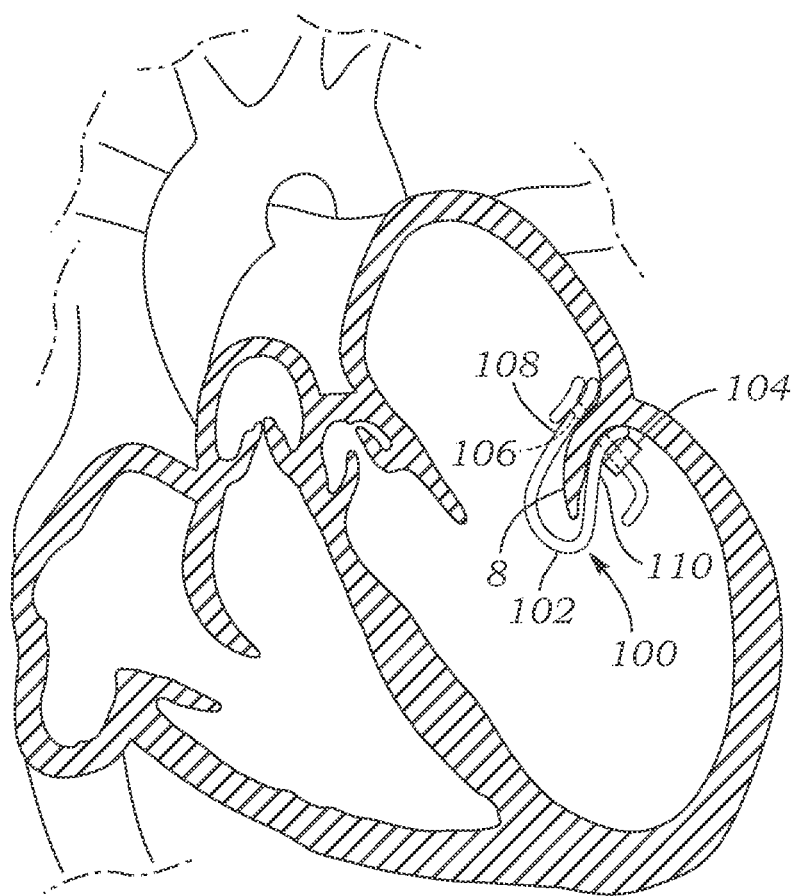
FIG. 1 shows a cross section of a heart with a prosthetic device for treating mitral valve regurgitation implanted on the posterior mitral valve leaflet, according to one embodiment.

FIG. 1 shows a cross sectional view of the heart with a prosthetic device 100 secured to a posterior leaflet 8 of the mitral valve, according to one embodiment. The device can comprise a body 102 (which may be ribbon-like as shown), a fastener 104 (e.g., a suture clip shown on the ventricular side in this example and therefore can be referred to as a ventricular-side fastener), and a length of suture 106 extending (at least) between the body 102 and the fastener 104 through the posterior leaflet 8. The body 102 can be wrapped around the leaflet such that a first end portion 108 of the body 102, fixedly engaged to suture 106, covers an atrial surface of the leaflet 8, while a second end portion 110 covers a ventricular surface of the leaflet 8. The suture 106 can extend from the fastener 104 through, in order, the second end portion 110, the leaflet 8, and the first end portion 108. In one embodiment, the fastener 104 can be positioned at the P2 region of the posterior leaflet 8.

The fastener 104 can be a suture clip, or another type of fastener that can be deployed from a catheter and secured to a suture within the patient's body. Various suture clips and deployment techniques for suture clips that can be used in the methods disclosed in the present application are disclosed in U.S. Publication Nos. 2014/0031864 and 2008/0281356 and U.S. Pat. No. 7,628,797, which are incorporated herein by reference. In the case of a slidable fastener, the fastener 104 can be movable along the suture 106 in the direction of the posterior leaflet 8, and configured to resist movement along the suture 106 in the opposite direction.

The body 102 is configured to treat or minimize mitral regurgitation by promoting coaptation with the opposing leaflet (in this case, the anterior leaflet). For example, the first end portion 108 (in this example on the atrial side) can have a thickness sufficient to serve as a gap filler to treat or prevent mitral regurgitation. In some embodiments, the entire body 102 has a substantially the same thickness. In other embodiments, at least one portion or section of the body 102 has a different thickness than another portion or section, for example, thicker at a central region and thinner at the first end portion 108 and second end portion 110.

Some embodiments in which a portion of the body 102 is relatively thicker at a region that coapts with the opposite leaflet, the anterior leaflet in FIG. 1, exhibit improved coaptation therewith. The device 100 also can effectively extend the length of the native leaflet to promote coaptation, which can be useful to treat or prevent functional mitral regurgitation (FMR). In this manner, the prosthetic device 100 (and other prosthetic devices disclosed herein) augments the overall size and the normal operation of the native leaflet on which it is mounted. Thus, the prosthetic device 100 (and other prosthetic devices disclosed herein) can be referred to as a prosthetic leaflet augmenting device.

The device 100 can be centered between the two bundles of chordae tendons below the mitral valve. In various embodiments, the device 100 geometry can vary to address the particular geometry of the diseased native mitral valve, including any pathological changes to the coaptation line.

The body 102 of the device 100 can be made from any of various suitable materials, including but not limited to, ePTFE (Gore-Text), silicone, polyurethane, PET (polyethylene terephthalate), or other polymeric materials, or biological materials, such as pericardial tissue, or composites thereof.

FIGS. 2A-2F illustrate the placement of an exemplary loop or rail delivery system 30 (for example, via a transfemoral approach) for subsequent introduction of the device 100 into the heart. The loop delivery system 30 can comprise an outer catheter 32, an inner catheter 34 extending through a lumen of the outer catheter 32, and a rail in the form of a guide suture 36 extending through the outer catheter 32 and inner catheter 34. The rail 36 can comprise any kind of flexible material, including conventional suture material or a metal wire (such as used for a conventional guide wire) and is used for subsequent delivery of the prosthetic device, as described in detail below.

Figure 2A:
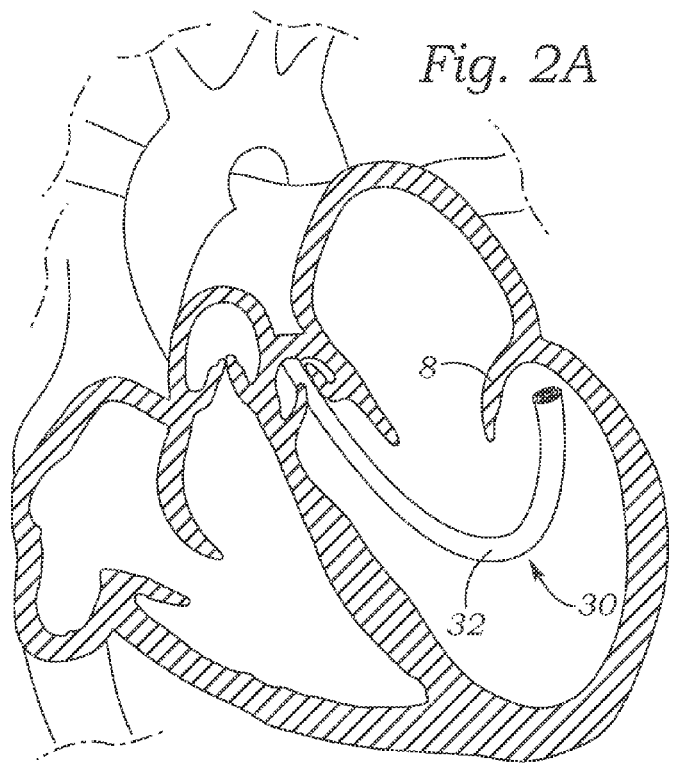
FIGS. 2A-2F show a method of implanting via a transfemoral approach a suture that extends through the left ventricle and the posterior leaflet for subsequent implantation of the prosthetic device shown in FIG. 1.
Figure 2B:
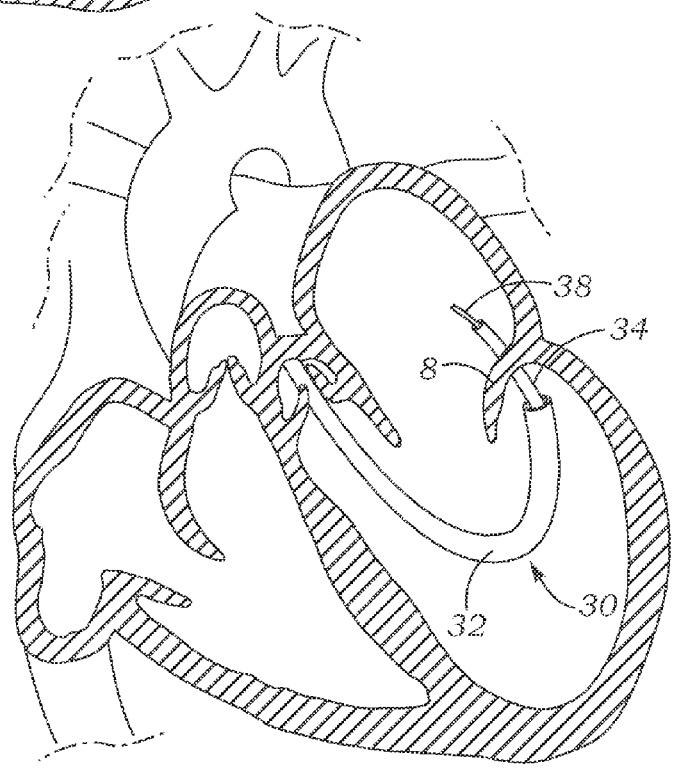

The loop delivery system 30 (including outer catheter 32) can first be advanced, for example, through the femoral artery, into the patient's left ventricle via the aorta and the aortic valve, as shown in FIG. 2A. Once the outer catheter 32 has been advanced into the left ventricle, the inner catheter 34 can be advanced to extend past the distal end of the outer catheter 32 towards the posterior leaflet (FIG. 2B). The distal end of the inner catheter 34 can comprise a hollow needle 38 to penetrate through the native leaflet, annulus, or muscle tissue. The inner catheter 34 can be advanced to abut the ventricular side of the posterior leaflet 8 (such as at the P2 position), such that, with additional force, the needle 38 can pierce the leaflet 8 and create an opening in the leaflet 8. The inner catheter 34 can then be further advanced such that a distal end of the inner catheter 34 can extend through the opening. In some embodiments, the inner catheter 34 and/or the outer catheter 32 are sufficiently stiff to promote piercing of the leaflet 8.

Figure 2C:
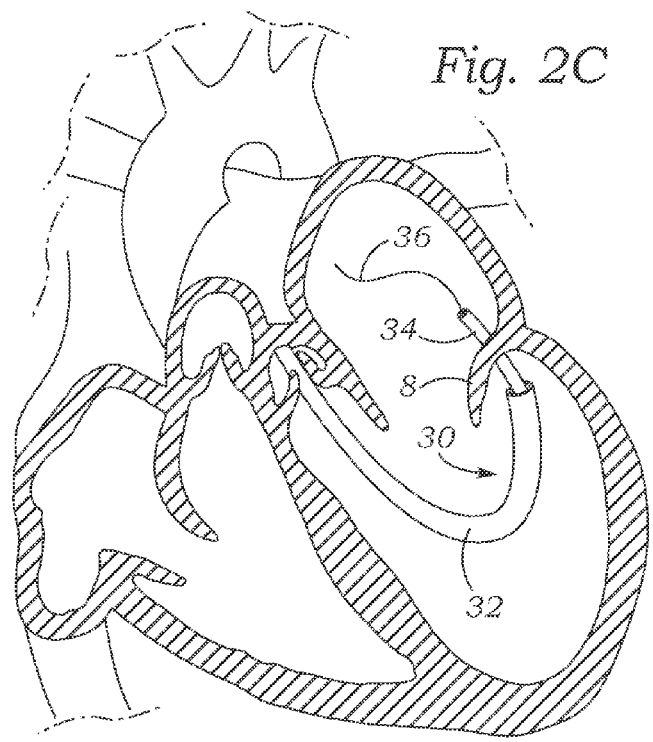

As shown in FIG. 2C, the suture 36 can then be advanced distally out of the inner catheter 34 and into the left atrium (FIG. 2C). In some embodiments, the suture 36 can run through an interior lumen of the inner catheter and the needle. In other embodiments, the needle 38 is not hollow and/or the suture 36 does not extend through the needle 38. In some embodiments, a portion of the guide suture 36 is releasably attached to an interior surface of the inner catheter 34 during placement of the suture 36.

Figure 2D:
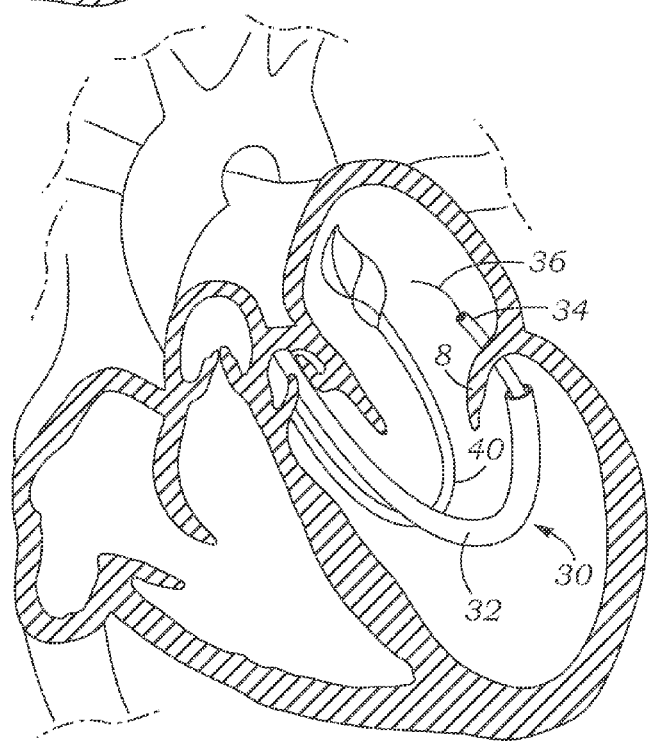
Figure 2F:
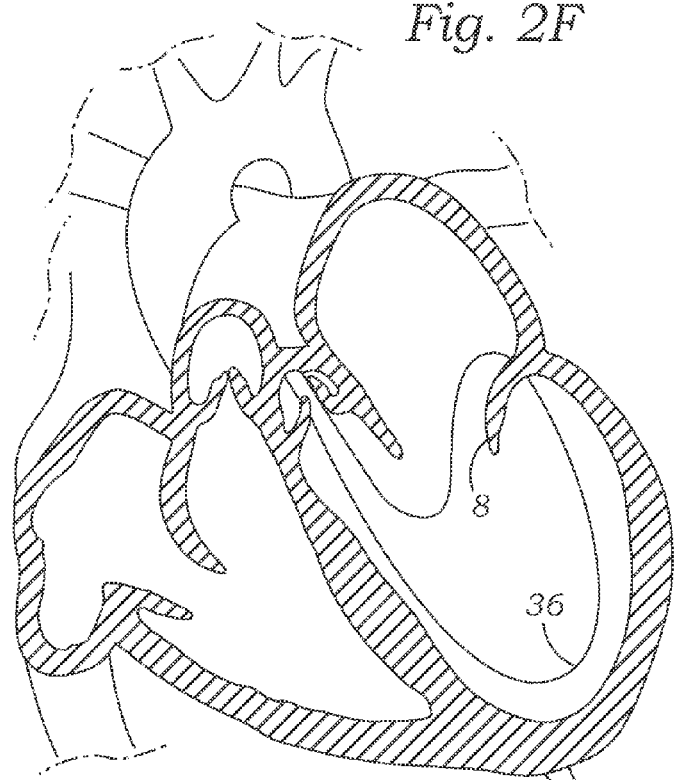
Figure 2E:
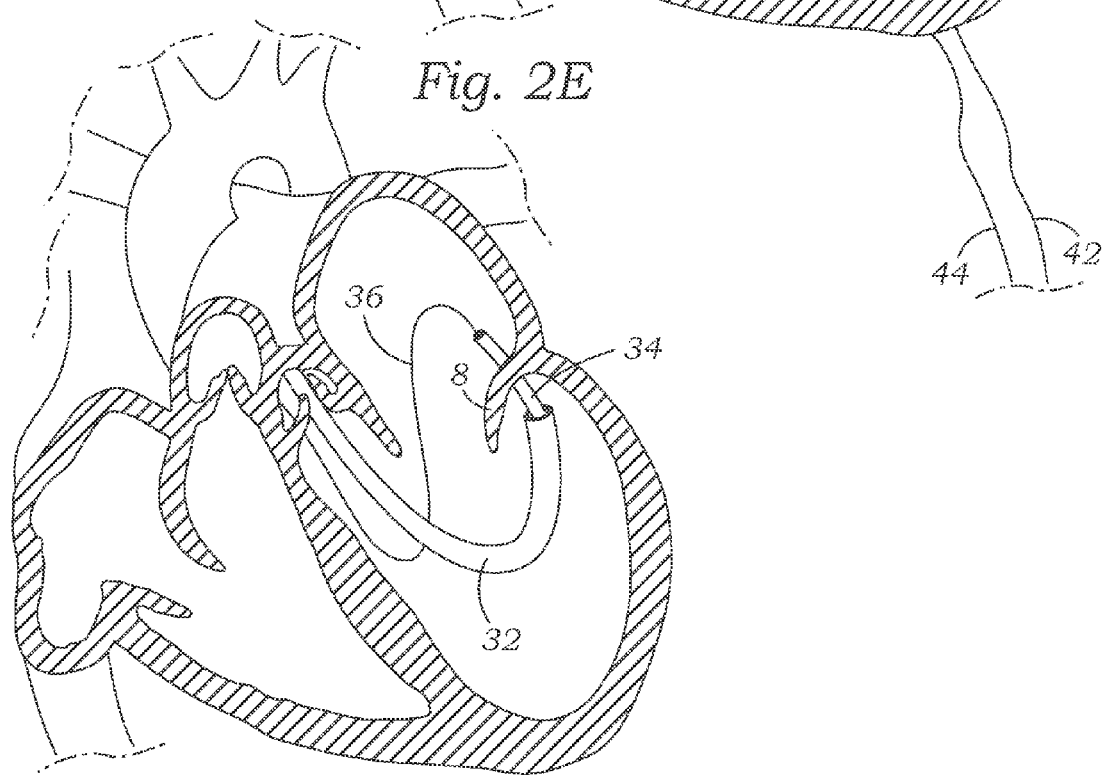

As shown in FIG. 2D, a separate snare catheter 40 can then be inserted, for example, transfemorally, into the heart to capture the leading end of the suture 36. Alternatively, the snare catheter 40 extends through a lumen of the outer catheter 32 and is advanced distally out from the outer catheter 32 in ensnaring the suture 36. The snare catheter 40 can be manipulated to enter the left ventricle and then to cross the mitral valve into the left atrium to capture the suture 36, (e.g., by positioning a loop at the end of the snare catheter around the end portion of the suture 36). The snare catheter 40 can then be retracted to pull the suture 36 between the leaflets of the mitral valve (FIG. 2E), into the left ventricle, and out the patient's body, for example, via the femoral artery (FIG. 2F). In some embodiments, the snare catheter 40 (with the captured suture 36) can be configured to be pulled into the outer catheter 32. In alternative embodiments, the snare catheter 40 and the outer catheter 32 can be deployed from a common catheter that extends into the aorta or the left ventricle. In still other embodiments, the snare catheter 40 can be deployed from a separate outer catheter that extends into the aorta or the left ventricle.

The inner and outer catheters 32, 34 can then be withdrawn, leaving behind a loop of guide suture 36 (FIG. 2F). In particular, the loop of suture 36 can enter the left ventricle via the aortic valve, extend through the posterior leaflet 8 from the ventricular side, and extend into the left atrium, before then looping back into the left ventricle via the mitral valve and exiting via the aortic valve. In various other embodiments, the directionality of the loop delivery system 30 can be reversed (i.e., the suture 36 enters the posterior leaflet from the atrial side and extends into the left atrium). Moreover, it should be noted that the suture 36 need not extend through the native leaflet and instead can extend through the native mitral valve annulus (desirably at or adjacent the P2 position) or through the muscle behind the native annulus (desirably at or adjacent the P2 position). Thus, for any of the embodiments disclosed herein, a guide rail (e.g., a suture) can be implanted to extend through a native leaflet, a native valve annulus, or the muscle behind the native valve annulus.

Figure 3A:
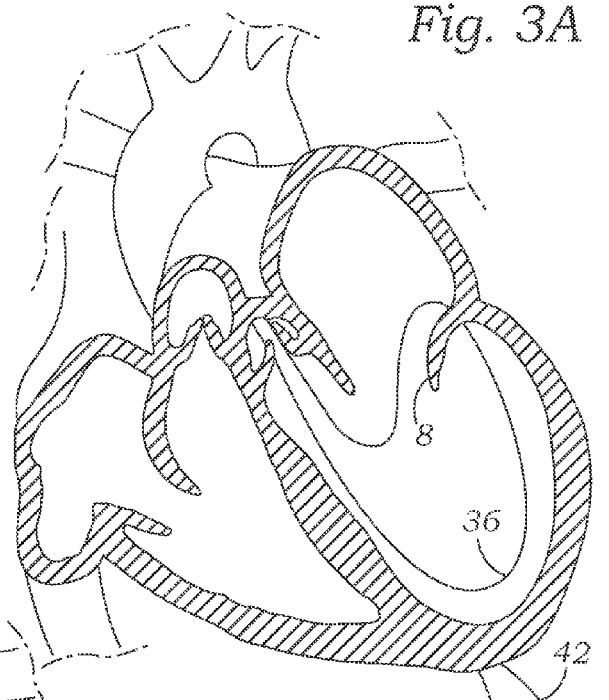
Figure 3B:
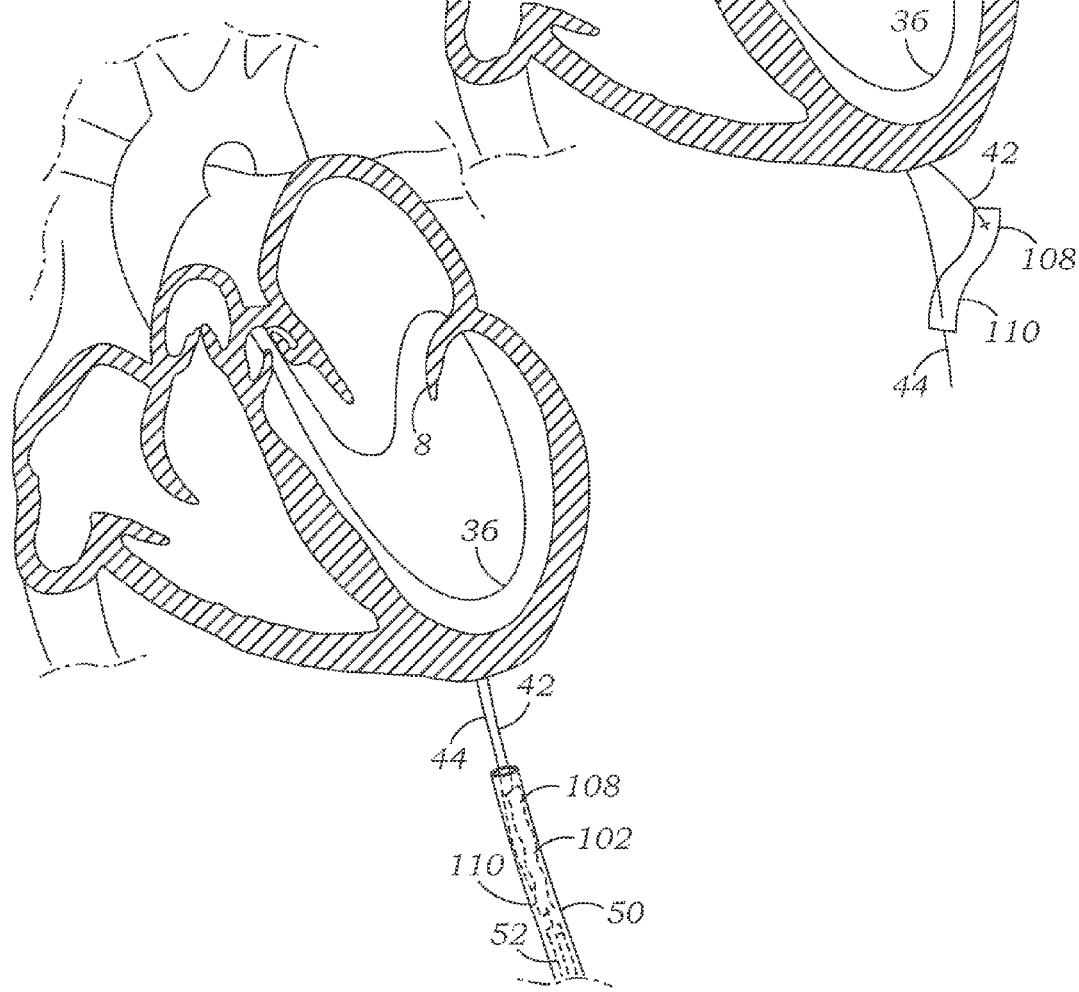

FIGS. 3A-3G illustrate an exemplary process of introducing and implanting the device 100 into a left ventricle of the heart. As shown in FIG. 3A, a first end segment 42 of the suture 36 (outside of the patient) can be configured to fixedly engage the first end portion 108 of the body 102. Also, a second end segment 44 of the suture 36 (also outside of the patient) can be configured to extend through the second end portion 110 of the body 102. In particular, the second end segment 44 can extend through a small opening or aperture in the body 102, which is small enough such that substantial blood cannot flow therethrough. Then, as shown in FIG. 3B, the body 102 and both suture end segments 42, 44 can be enclosed within a delivery catheter 50 for delivery to the heart. In some embodiments, the body 102 can be contained in a compressed state within the catheter 50. For example, the body 102 can be resiliently deformed in this compressed configuration, such that the body 102 resiliently returns to the configuration shown in FIG. 3A when released from constraint. The second end segment 44 can extend out the proximal end of the catheter, outside of the patient, and is thus available for manipulation during the process of installing the device 100. The suture 36 can thus be used to guide the delivery of the device 100 and other delivery components to an appropriate location within a patient's vasculature.

Figure 3C:
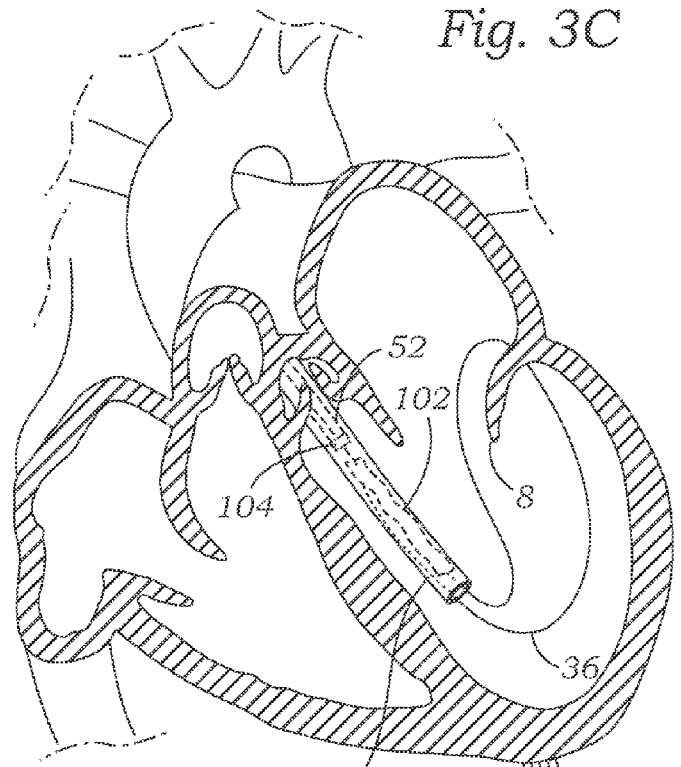
Figure 3D:
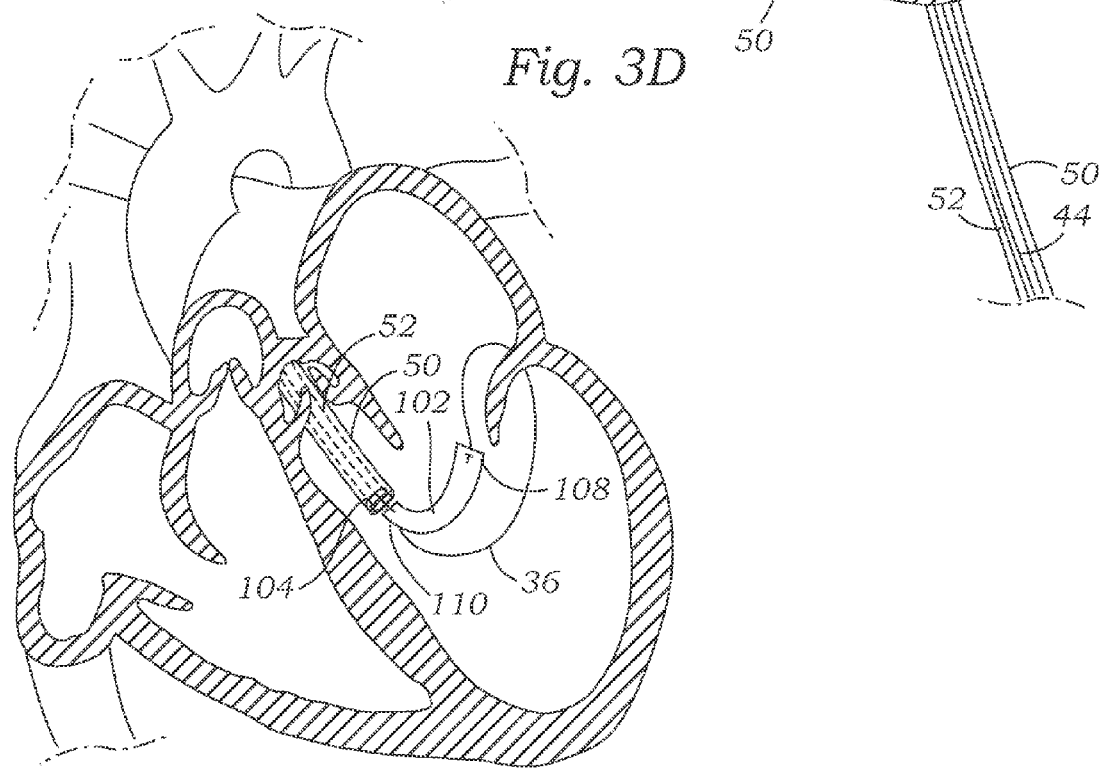
Figure 3E:
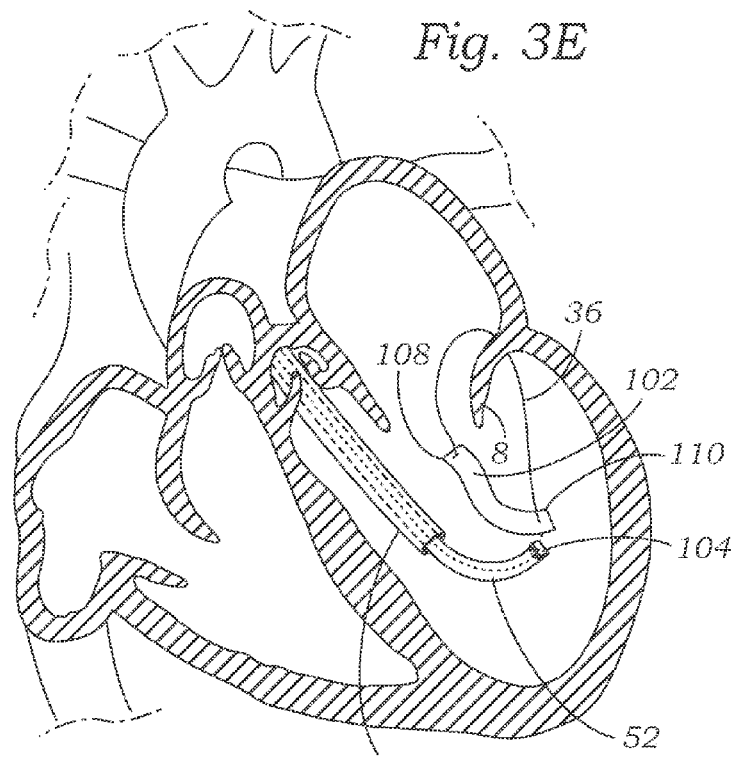

As shown in FIG. 3C, the delivery catheter 50 can be advanced into the left ventricle. Once a distal end of the catheter 50 is within the left ventricle, an inner catheter or pusher member 52, configured to extend through the delivery catheter 50 proximal to the body 102, can be advanced to advance the device 100 out of the delivery catheter 50. In various embodiments, the delivery catheter 50, inner catheter 52, and guide suture 36 can be independently retracted proximally or extended distally with respect to one another. The inner catheter 52 can operate as a pusher, urging the device 100 distally along the suture 36. The inner catheter 52 can be used to urge the device 100 distally along the suture 36 in the direction of the native mitral valve (FIGS. 3D-3E).

Figure 3F:
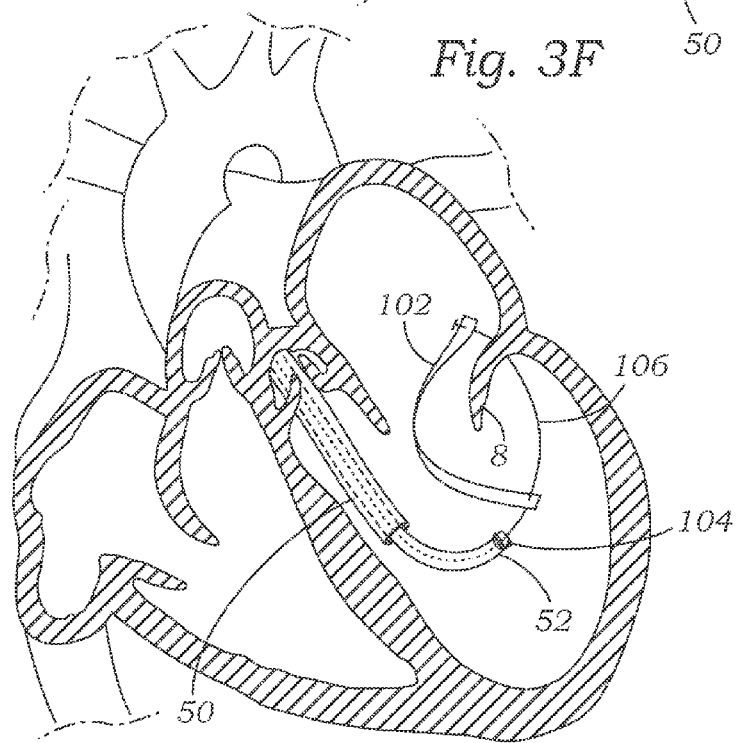

The second end segment 44 of the suture 36 (extending outside of the patient) can be pulled simultaneously and/or in tandem with advancement of the delivery catheter 50 and/or the inner catheter 52. This pulling of the second end segment 44 pulls the suture loop 36 through the body 102 as the body is advanced distally toward the posterior leaflet 8. Pushing the body 102 while pulling the suture loop brings the body 102 into a suitable orientation for installation at the posterior leaflet 8 (FIG. 3F). Ultimately, as shown in FIG. 3G, the first end portion 108 can be brought adjacent to the atrial side of the posterior leaflet 8, while the second end portion 110 can be brought adjacent to the ventricular side.

Once the body 102 is in its final, operating position, the device 100 can be secured in place using the fastener 104 (FIGS. 3G-3H), which can be deployed from the inner catheter 52, the outer catheter 50, or a separate catheter. As shown in FIGS. 3F-3G, the fastener 104 can be seated at a distal end of the inner catheter 52 to eventually fix the device 100 in place on the posterior leaflet 8 once positioned. The outer and inner catheters 50, 52 can then be retracted from the site of implantation within the heart and removed from the patient (FIG. 3H).

In some embodiments, placement of the body 102 can be reversed during delivery, such that first end segment 42 of the suture 36 (and the first end portion 108 of the body 102) can be brought against the ventricular side of the leaflet 8, and the second end segment 44 of the suture 36 (and the second end portion 110 of the body 102) can be brought against the atrial side. In some embodiments, this reversal of placement is accomplished simply by reversing the orientation of the body 102 during loading onto the sutures 36, for example, in the step illustrated in FIG. 3A. FIGS. 18A-18E show an exemplary process for delivering the body 102 transseptally, for example, from the right atrium, through the atrial septum, and into the left atrium, which results in such a configuration.

Figure 18A:
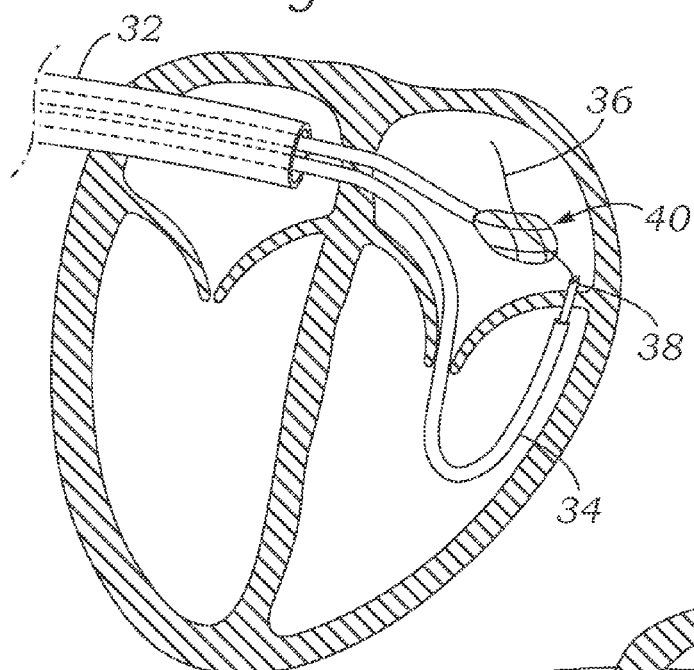
Figure 18B:
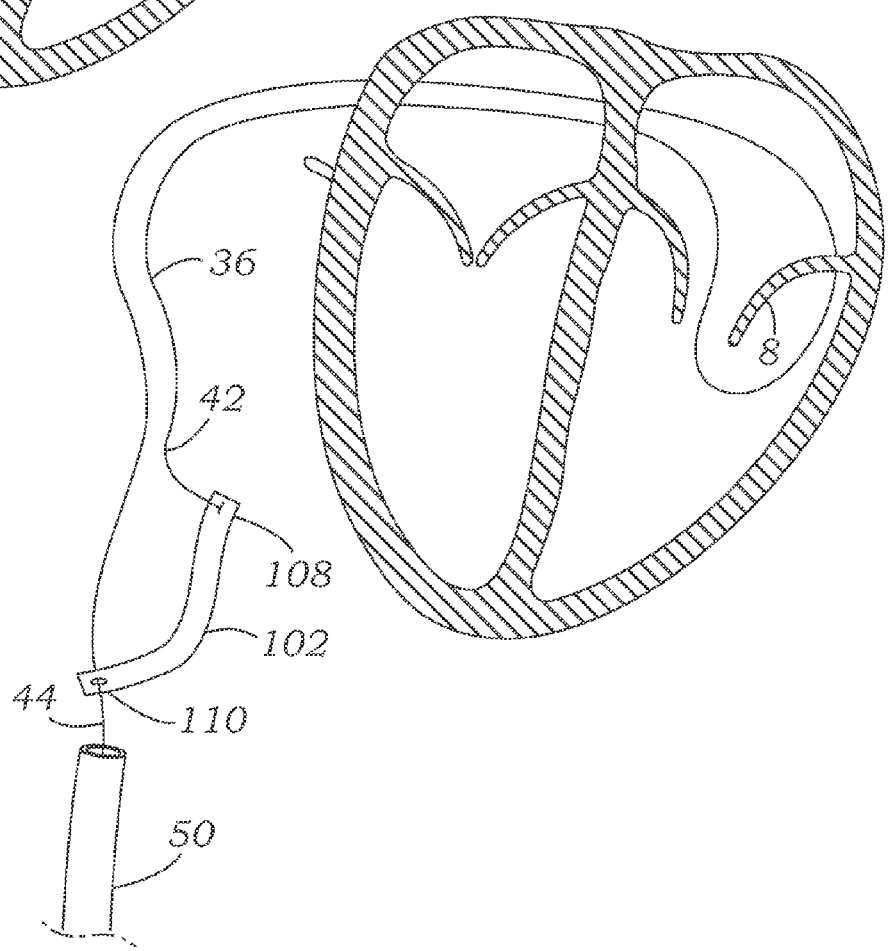
Figure 18C:
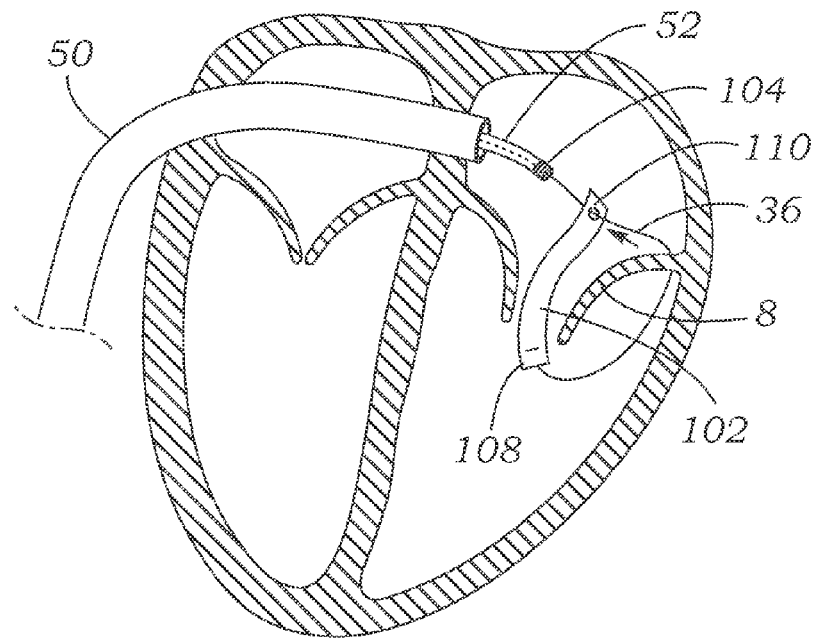
Figure 18D:
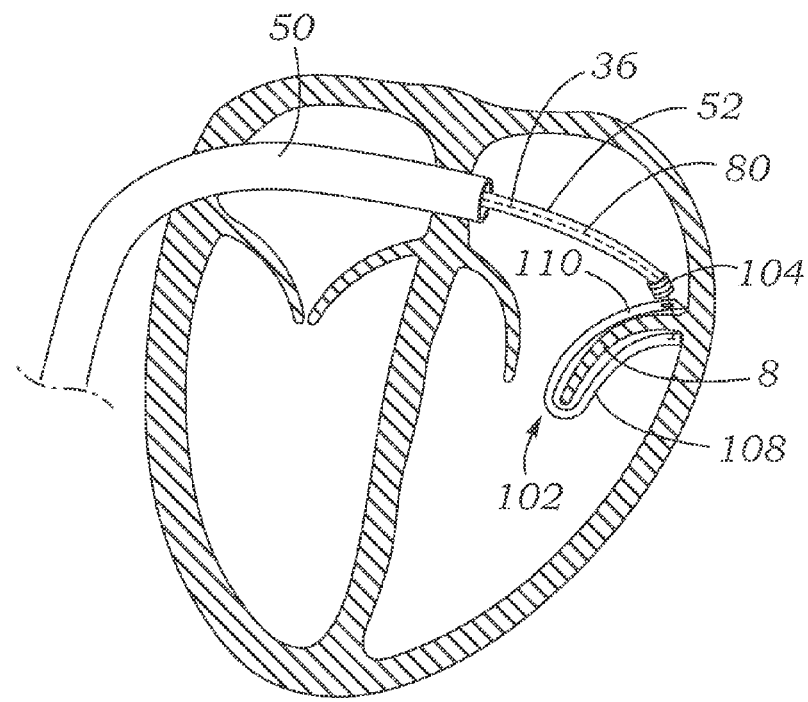

As shown in FIG. 18A, the outer catheter 32 and/or inner catheter 34 can be inserted into the left atrium transseptally, and the inner catheter 34 can bring the suture 36 between the leaflets 6, 8 of the mitral valve into the left ventricle, and then through the posterior leaflet 8 back into the left atrium. The snare catheter 40 (which also can extend through the outer catheter 32) can be inserted transseptally to capture the suture 36 and bring it outside of the patient's body. The body 102 can then be loaded on the suture 36 (FIG. 18B) and delivered to the posterior leaflet 8 (FIGS. 18C and 18D). As shown in FIGS. 18D-18E, the fastener 104 can also be located on the atrial side of the leaflet 8, and the installed suture length 106 can extend from the fastener 104 through, in order, the first end portion 108 of the body, the posterior leaflet 8, and the second end portion 110.

FIG. 18F shows that the tension in the suture 106 can be adjusted to affect the position of the first end portion 108 of the implant. In FIG. 18F, the suture 106 is not pulled tight to pull the first end portion 108 against the ventricular side of the posterior leaflet 8. Instead, a sufficient degree of slack in the suture 106 allows the first end portion 108 to hang or "float" below the posterior leaflet. Also, the tension of the suture 106 can be adjusted to fit the device 100 to the size of the native leaflet 8. In this manner, the device 100 has the benefit of being a "one-size-fits-all" and/or otherwise adaptable to fit around leaflets of varying sizes and/or geometries.

Figure 4:
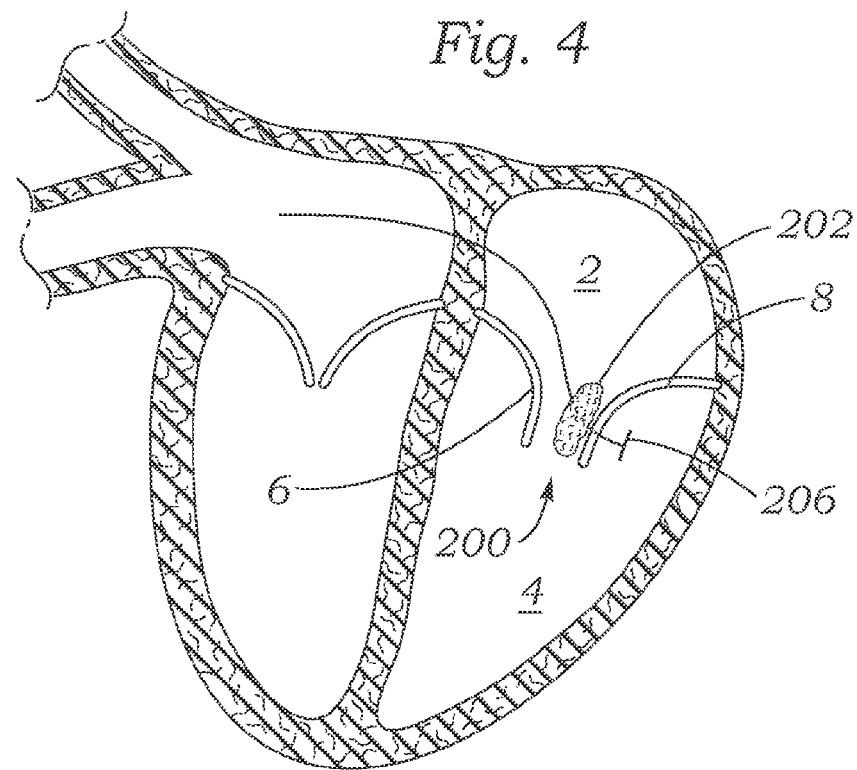
FIG. 4 shows a cross section of a heart with a prosthetic device for treating mitral valve regurgitation implanted on the posterior mitral valve leaflet, according to another embodiment.
Figure 5:
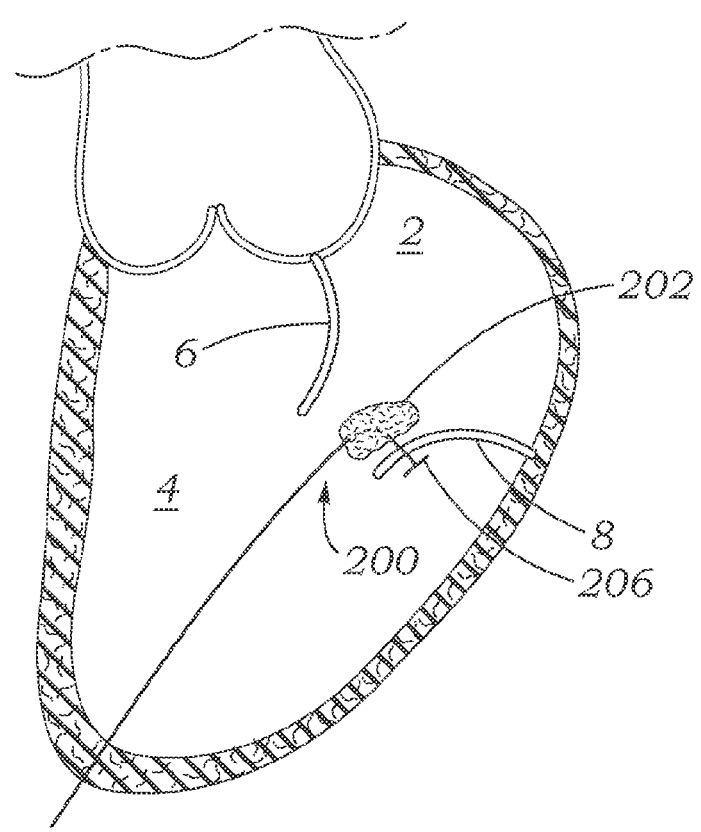
FIG. 5 shows a cross section of the left side of a heart with a prosthetic device for treating mitral valve regurgitation implanted on the posterior mitral valve leaflet, according to another embodiment.

FIGS. 4-7 show an alternative device 200 comprising a body 202 according to another embodiment, wherein the body 202 is coupled to one of the native leaflets using, for example, suture. The body 202 can be formed from any of various suitable materials, including bio-compatible materials such as pericardial tissue, polymer, sponge, foam, gel, or a gel or saline filled structure such as a balloon. The material composition of the body 202 can be selected to increase desirable characteristics of the body 202, such as performance, durability, promotion of native tissue in-growth, etc. The body 202 can be formed in any of various suitable shapes, such as a rectangle, a semi-elliptical ring or U-shape, or a semi-ellipse. As shown in FIG. 4, the body 202 can be sutured to the posterior leaflet 8 using suture(s) 206 via a transseptal approach. Alternatively, as shown in FIG. 5, the body 202 can be sutured to the posterior leaflet 8 using suture(s) 206 via a transapical approach. In use, the opposite leaflet (the anterior leaflet in the illustrated embodiment) can coapt against the body 202 to prevent, reduce, or minimize regurgitation.

FIG. 6 shows the body 202 after suturing to the native posterior leaflet 8. In this embodiment as shown, two sutures 206 can be sufficient to couple the body 202 to the leaflet 8. The sutures 206 can be positioned as shown, with one suture 206 at either end of the body 202, which spans a width of the leaflet 8. In other embodiments, additional or fewer sutures can be used, and the sutures can be situated in alternative locations on the body 202 and/or on the leaflet 8.

FIG. 7 shows an embodiment of a method for coupling the body 202 to the posterior native leaflet 8 using a length of elongate material 206 and a pair of fasteners in the form of slidable locking devices 208. The elongated material 206 can comprise, for example, a length of thread or suture material, or a metal or polymeric wire, or any other material suitable for suturing, such as biological tissue. In the illustrated embodiment, a single strand of material 206 is used, although in alternative embodiments, two or more strands 206 can be used to couple the body 202 to the native leaflet 8.

In order to couple the body 202 to the native posterior leaflet 8, one or both of the slidable locking devices 208 can be guided along the strand of material 206 toward the native leaflet 8, thereby decreasing the length of the strand 204 between the locking devices 208 until the body 202 is held firmly against the leaflet 8 in a desired deployed configuration. Because the locking devices 208 are positioned behind the posterior leaflet 8 in this configuration (that is, they are located between the native leaflet 8 and the wall of the left ventricle 2), the potential for interference between the locking devices 208 and the coaptation region of the leaflets is minimized. Once the body 202 is situated in this configuration, any excess material 210 can be trimmed to prevent the material 206 from interfering with the operation of the heart valve. The locking devices 208 can be configured to slide or pass over a suture in one direction and to resist movement in the opposite direction. Examples of locking devices (also referred to as suture securement devices) that can be implemented in the embodiment of FIG. 7 are disclosed in U.S. Publication No. 2014/0031864, which is incorporated herein by reference.

As discussed above, FIGS. 4-7 show a body 202 coupled or secured to the posterior leaflet 8. In alternative embodiments, a body 202 can be coupled as described above to the anterior leaflet in place of or in addition to the body 202 coupled to the posterior leaflet 8.

Figure 8:
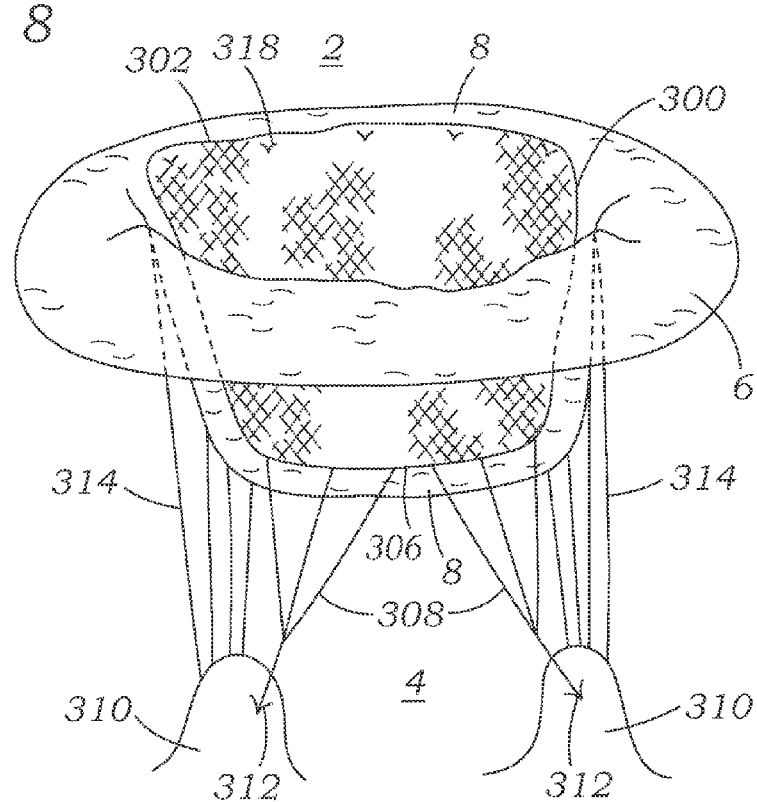
FIGS. 8-10 show perspective and side views a prosthetic device for treating mitral valve regurgitation implanted on the posterior mitral valve leaflet, according to another embodiment.
Figure 9:
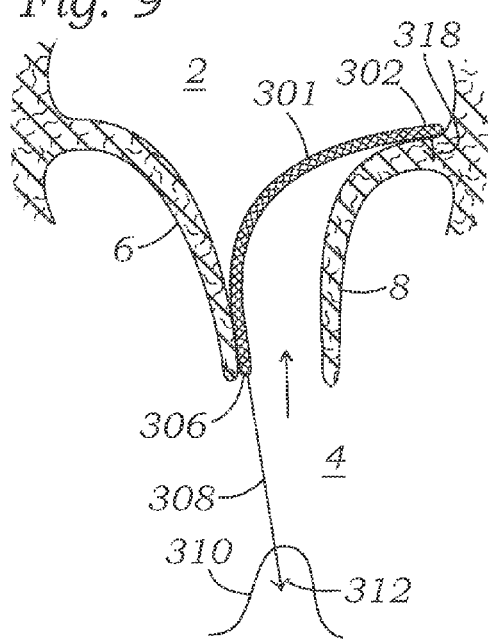
Figure 10:
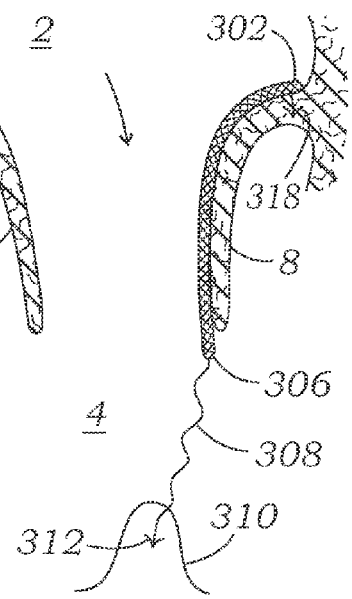

FIGS. 8-10 show another exemplary device 300, which can be implanted at the mitral valve region for treatment of mitral regurgitation. The device 300 can comprise a strong, flexible sheet of blood-impermeable material. The device 300 can have a body 301 with an upper, first end portion 302 that is secured to the mitral annulus and/or the region of a mitral valve leaflet adjacent to the mitral annulus. The portion of the body 301 extending away from this first end portion 302 is a free end portion of the body 301. In the illustrated example, the first end portion 302 is attached to the mitral annulus above the posterior leaflet 8. In other examples, the arrangement can be reversed with the device 300 secured to an anterior leaflet 6. The device 300 can be secured to the native tissue by various means, such as suture, barbed anchors, and/or microanchors 318. The first end portion 302 of the body 301 can be wider than the free end portion of the body 301, and thus the body 301 can have a generally trapezoidal shape.

In FIG. 8, the lower end of the anterior leaflet 6 is not shown in order to show the lower end of the posterior leaflet 8 and a lower, second end portion 306 of the device 300 extending downwardly through the mitral orifice and into the left ventricle 2. The second end portion 306 of the device can be shorter, longer, or about the same length as the leaflet to which it is attached. As shown in FIGS. 9 and 10, the second end portion 306 of the device in the illustrated embodiment can extend below the lower end of the posterior leaflet during diastole (FIG. 10), and extends short of the lower end of the anterior leaflet 6 during systole (FIG. 9).

The second end portion 306 can be tethered to a location in the left ventricle 4. For example, the second end portion 306 can be tethered to the papillary muscle heads 310 via tethers 308 (which can be made of, for example, suture material) and anchors 312, as shown, (similar to the manner in which the native chordae tendineae 314 tether the native leaflet 8 to the papillary muscles 310), and/or can be tethered to the apex of the left ventricle 4.

During systole, as shown in FIG. 9, the device 300 inflates or fills with blood from the left ventricle 4 and expands laterally toward the anterior leaflet 6. This expansion causes the lower portion of the device 300 to seal against the anterior leaflet 6, thereby blocking the flow of blood back into the left atrium 2. The lateral edges of the device 300 can seal between the two native leaflets adjacent to the commissures where the native leaflets still naturally coapt with each other. The tethers 308 prevent the second end portion 306 of the device 300 from moving toward and/or into the left atrium 2 and thereby breaking the seal with the anterior leaflet 6. Thus, the device 300 augments the native posterior leaflet and helps seal the mitral orifice in the case where the native leaflets 6, 8 do not otherwise not fully coapt, thereby allowing regurgitation therebetween.

During diastole, as shown in FIG. 10, the device 300 collapses against the posterior leaflet 8, allowing blood to flow from the left atrium into the left ventricle 4 with minimal obstruction from the device 300.

Figure 11:
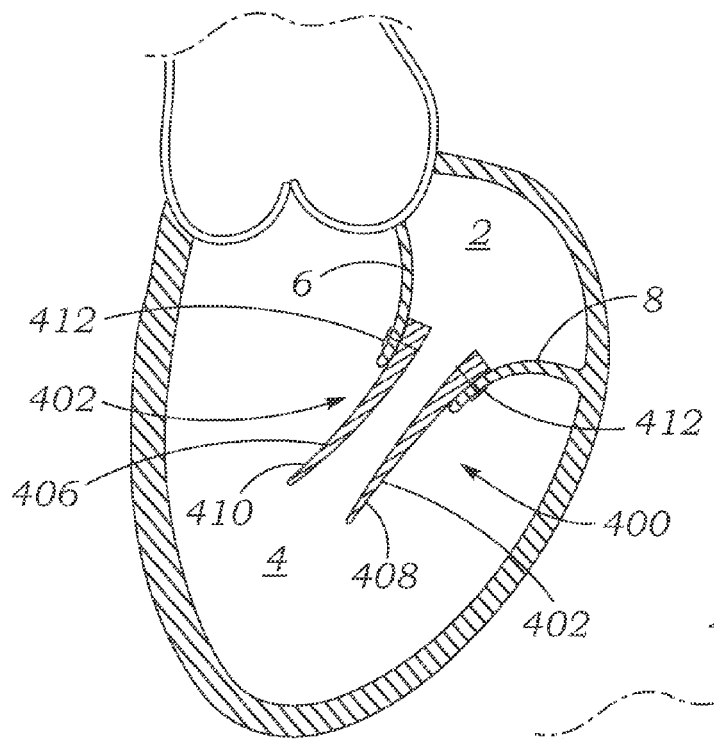
FIG. 11 shows a cross section of the left side of a heart with prosthetic devices for treating mitral valve regurgitation implanted on the posterior and anterior mitral valve leaflets, according to another embodiment.

FIG. 11 shows embodiments of prosthetic devices 400, 402 that can be used to extend the effective lengths of the native leaflets 6, 8. The prosthetic devices 400, 402 can comprise bodies 404, 406 and one or more sutures 412 for coupling each body 404, 406 to a respective anterior or posterior native leaflet 6, 8. In use, the bodies 404, 406 have free end portions 408, 410 extending away from the ends of the native leaflets, extending the effective lengths of the native leaflets, thereby increasing the chance of and extent of coaptation between them, as described more fully below.

The bodies 404, 406 can comprise a material that is sufficiently stiff to reduce leaflet prolapse, and sufficiently flexible to increase the extent of leaflet coaptation. Suitable materials can include, for example, biological materials such as pericardial tissue, ePTFE (Gore-Tex®), silicone, polyurethane, PET, or other polymeric materials, or composites thereof. FIG. 11 shows that a device 400, 402 can be used on each of the anterior and posterior native leaflets 6, 8, but in alternative embodiments, only one such device can be used. In some embodiments, tethers can be used to tether free end portions of the bodies 404, 406 to locations in the left ventricle 4, thus reducing the chances of prolapse of the prosthetic devices 400, 402 during systole.

Figure 12:
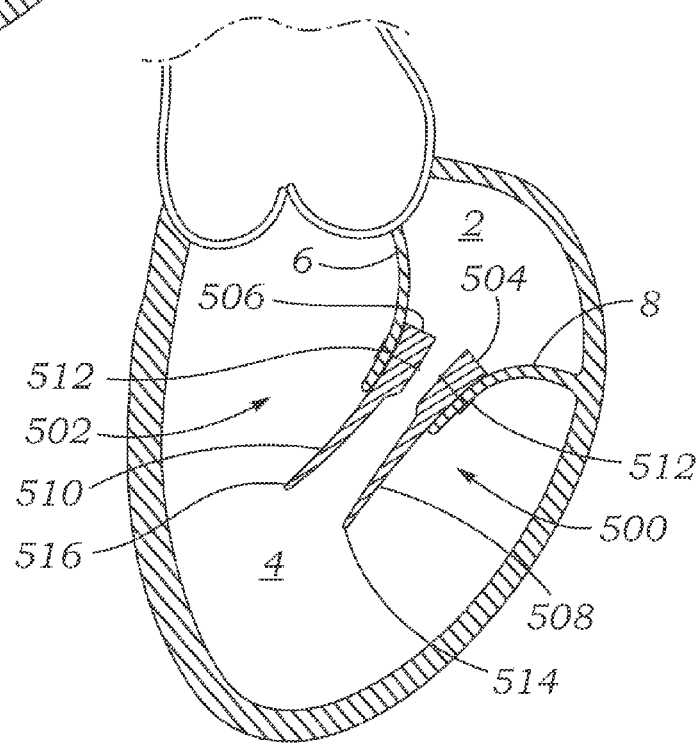
FIG. 12 shows a cross section of the left side of a heart with prosthetic devices for treating mitral valve regurgitation implanted on the posterior and anterior mitral valve leaflets, according to another embodiment.

FIG. 12 shows exemplary prosthetic devices 500, 502 which combine features of the prosthetic bodies described above. The prosthetic device 500 is shown coupled to the posterior native leaflet 8, while the prosthetic device 502 is shown coupled to the anterior native leaflet 6. The prosthetic devices 500, 502 include relatively thick upper portions 504, 506 and relatively thin, elongate free end portions 508, 510, which function in a manner similar to the devices 300, 400, 402 described above. The free end portions 508, 510 can have respective distal end portions 514, 516, which represent the effective distal ends of the extended leaflets.

In use, the free end portions 508, 510 extend the effective lengths of the respective leaflets, and can facilitate initiation of leaflet coaptation during ventricular systole. During systole, the leaflets are urged toward one another due to the pressures extant in the left ventricle 4 and left atrium 2. Due to the extended effective length of the leaflets, the distal end portions 514, 516 are more likely to coapt than the ends of the native leaflets absent the extensions. Once coaptation is initiated, and thus blood flow from the left ventricle 4 to the left atrium 2 at least partially impeded, the pressure in the left ventricle 4 can increase, further increasing the pressure differential between the left ventricle 4 and the left atrium 2, thus further urging the leaflets 6, 8, towards one another.

As a result, the portions of the leaflets 6, 8, and their respective extensions 502, 500 which coapt, increases (both in the direction from the distal end portions 514, 516 toward the left atrium 2, and from the locations of the devices 500, 502, toward the commissure points of the mitral valve), leading to a cycle of increasingly impeded blood flow, increased pressure differential, and increased coaptation of the leaflets. Thus, by facilitating initiation of coaptation, the free end portions 508, 510 can help to reduce regurgitation of blood from the left ventricle 4 to the left atrium 2 during ventricular systole. Further, the upper portions 504, 506 can further help to prevent regurgitation in the manner described above with respect to prosthetic devices 100, 200, 300, 400, 402.

FIG. 12 shows that the devices 500, 502 can be sutured to the native leaflets 8, 6, with sutures 512, but in alternative embodiments, the devices 500, 502 can be clipped or otherwise fastened to the native leaflets 8, 6. In alternative embodiments, only one of the devices 500, 502 can be used rather than both.

FIGS. 13A-13D show an embodiment of an exemplary process for introducing the device 300 (which can also be used for implanting devices 200, 400, 402, 500, 502 described above). First, a loop delivery system can be used, as described above with respect to the introduction of device 100, to run a suture 36 into the left ventricle, through the posterior leaflet 8, and into the left atrium. As with device 100, the first end segment 42 of the looped suture 36 can be fixedly attached to a first end portion 302 of the body 301. However, unlike with the device 100, the second end segment 44 of the suture 36 does not extend through the second end portion 306 of the body 301. That is, the second end portion 306 is not attached to the suture 36 and thus the second end portion 306 need not comprise an opening for a suture, a guidewire, or the like.

Figure 13C:
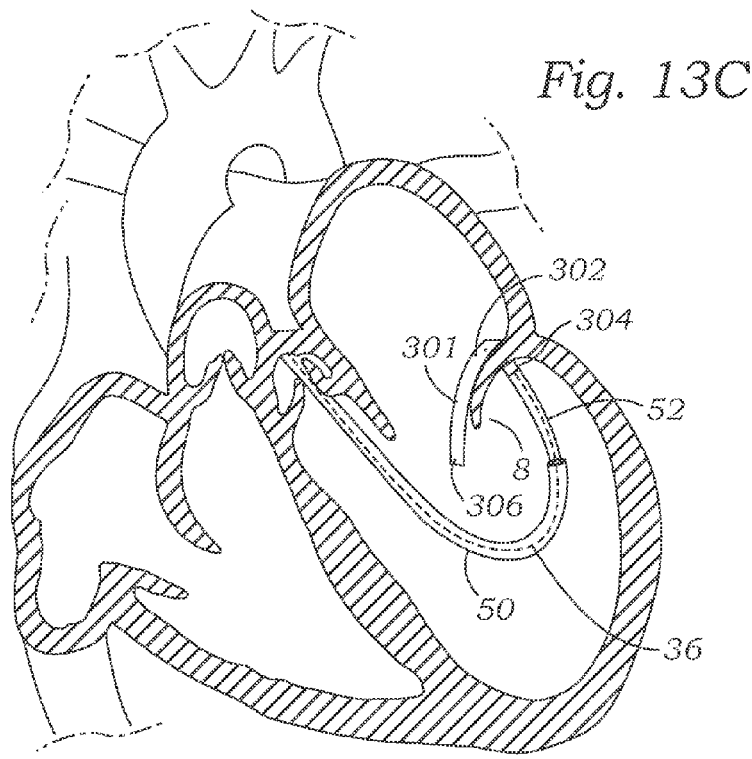
Figure 13D:
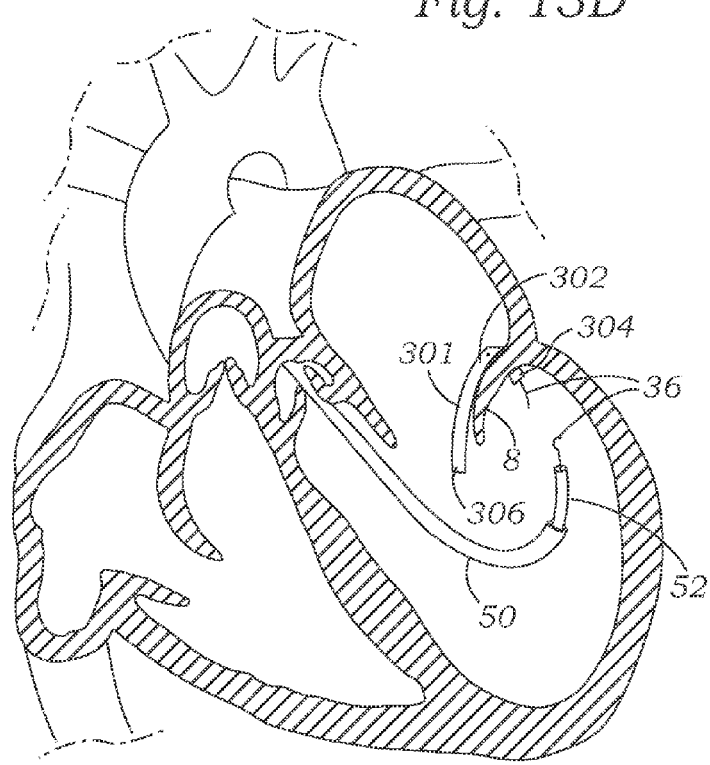

Once the guide suture 36 is in place, the device 300 can be advanced along the suture 36 into the left ventricle and into the vicinity of the native mitral valve using outer and inner catheters 32, 34 as described above. During delivery, the delivery catheter 50 can sit adjacent and proximal to the second end portion 306 of the body 301. Once ejected from the catheter 50 in the vicinity of the native mitral valve, the body 301 can be positioned as shown in FIG. 13B, with the first end portion 302 positioned in the atrium, in the vicinity of the atrial side of the posterior leaflet 8 (such as near the P2 position) and the second end portion extending through the mitral valve into the left ventricle. To promote this placement, the suture 36 can be tightened by pulling on the second end segment 44 (in the direction of the arrows as shown in FIG. 13B, simultaneously and/or in tandem with advancing the delivery catheter 50 and/or inner pusher catheter 52) to bring the first end portion 302 against the atrial side of the posterior leaflet 8 (FIGS. 13B-13C). The fastener 304 can then be deployed to secure the device 300 in place at the posterior leaflet 8. Finally, the suture 36 can be cut proximal to the fastener 304, and the catheters 50, 52 can be withdrawn (FIG. 13D).

Figure 14A:
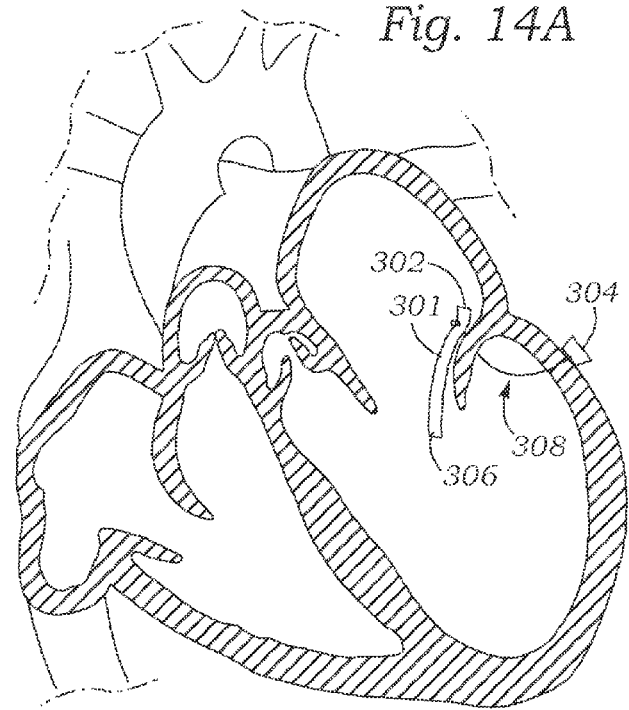
Figure 14B:
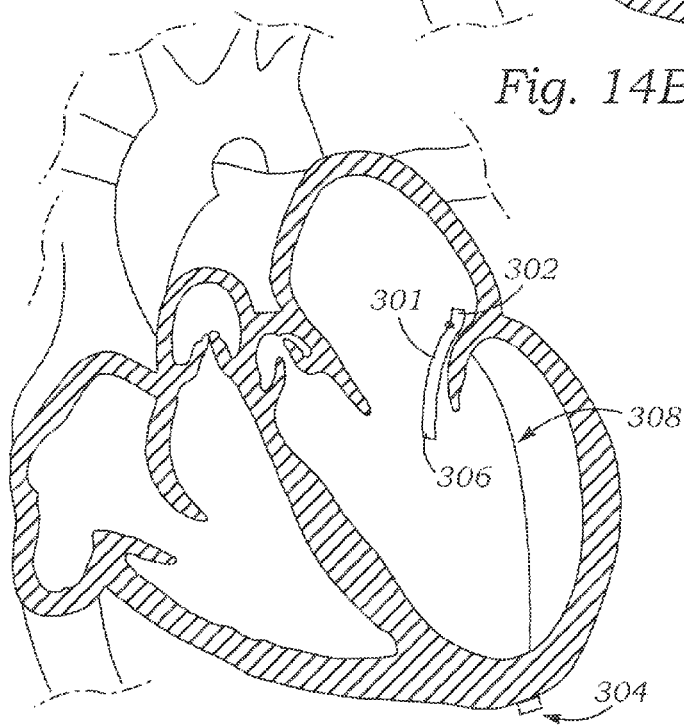

FIGS. 14A-14E show various alternative means for fastening the device 300 to location(s) within or along the heart. FIG. 14A shows the device 300 fastened to the ventricular wall, with the fastener 304 located along an external lateral surface of the heart. The implanted suture 308 can extend through the heart muscle, into the left ventricle and across the posterior leaflet 8. FIG. 14B shows the fastener 304 instead located outside the heart at the left ventricular apex. In FIG. 14C, the fastener 304 fixes the first end portion 302 to the posterior leaflet 8, while a suture or tether 308 connects the second end portion 306 to an anchor 312 attached to a papillary muscle head 310.

Figure 14E:
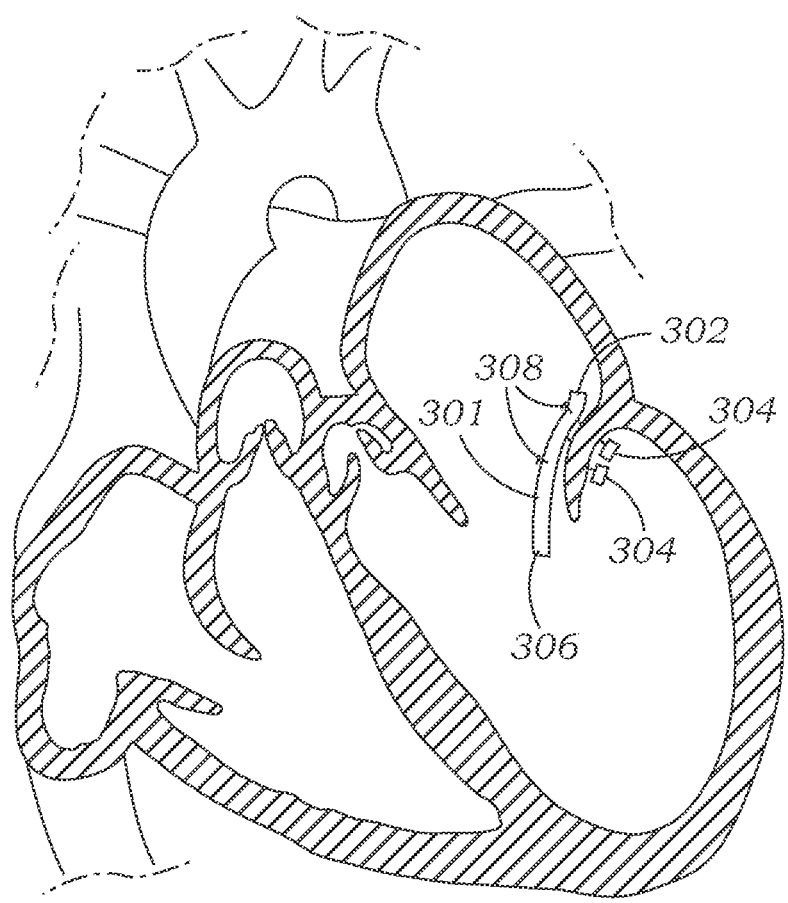

In various embodiments, the methods of delivering the device 300 may vary, such that the sutures can run in the directions shown. In some embodiments, the device 300 can be delivered via a transapical or other approach that extends directly through a wall of the heart from the outside of the heart. In some embodiments, as shown in FIG. 14D, there can be two (or more) implanted sutures 308 extending through a single fastener 304 attached to the ventricular side of the posterior leaflet. In some embodiments, as shown in FIG. 14E, there can be two (or more) fasteners 304 attached to the ventricular side of the posterior leaflet, which can be delivered along two or more suture loops 36.

Figure 15A:
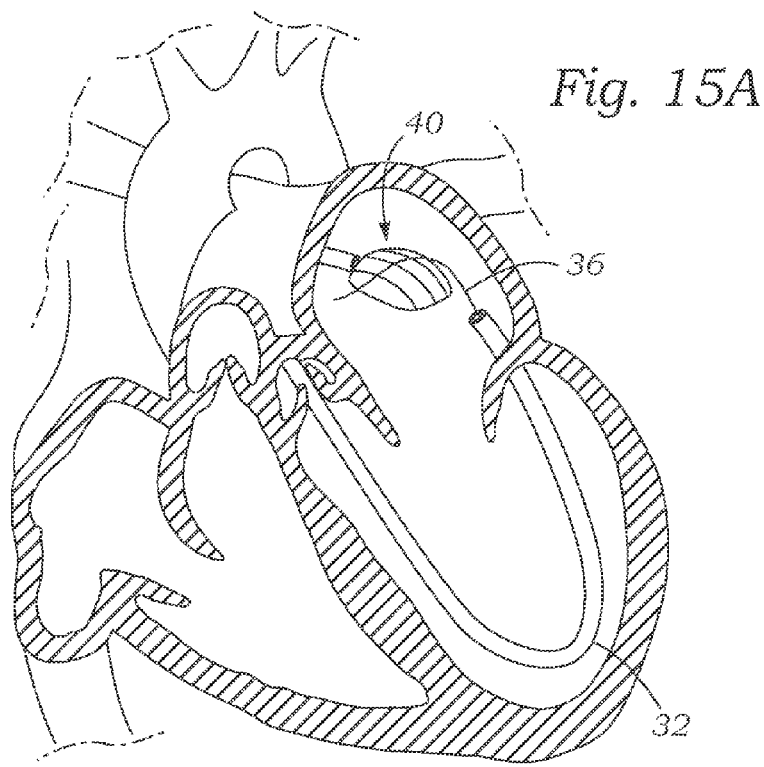
FIGS. 15A-15B are cross sections of a heart showing the implantation of a suture through the posterior mitral valve leaflet, according to another embodiment.
Figure 15B:
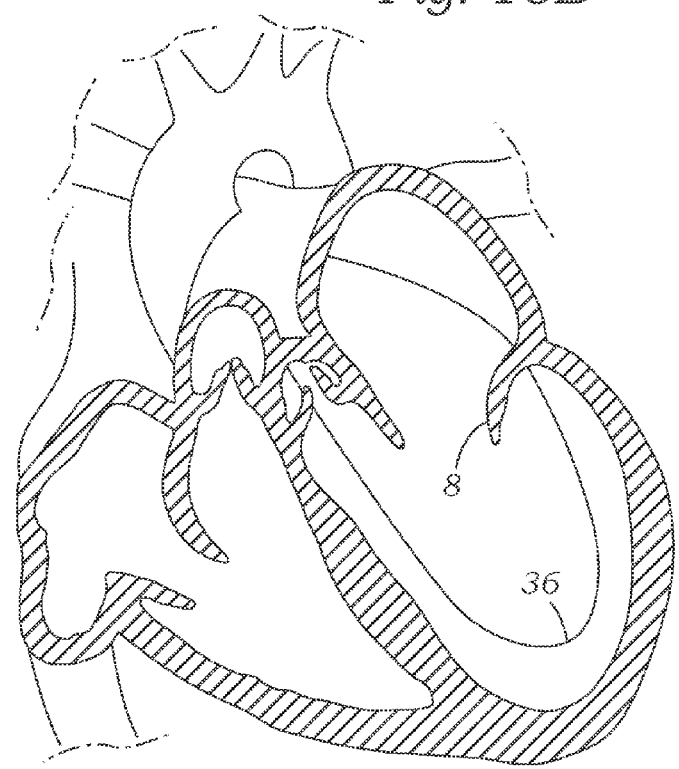

FIGS. 15A-15B shows an embodiment of an alternative process for delivering a suture or rail 36 into the heart. The catheters 32, 34 can bring the suture 36 transfemorally through the aortic valve into the left ventricle, across the posterior leaflet 8, and into the left atrium. The snare catheter 40 can then be inserted into the right atrium (such as via the superior vena cava), then transseptally across the atrial septum (FIG. 15A) into the left atrium to capture a leading end of the suture 36 and bring it back outside the patient's body, leaving behind a suture loop as shown in FIG. 15B for subsequent device deployment.

As discussed, in some embodiments, the snare catheter 40 can emerge from the outer catheter 32, whereas in other embodiments the snare catheter 40 is separate from the delivery catheter. In some embodiments, the directionality of suture loop 36 delivery can be reversed (i.e., the suture enters the posterior leaflet from the atrial side). In one such embodiment, the snare catheter can be inserted transfemorally into the left ventricle while the delivery catheter can deliver the suture 36 into the left atrium transseptally.

Figure 16A:
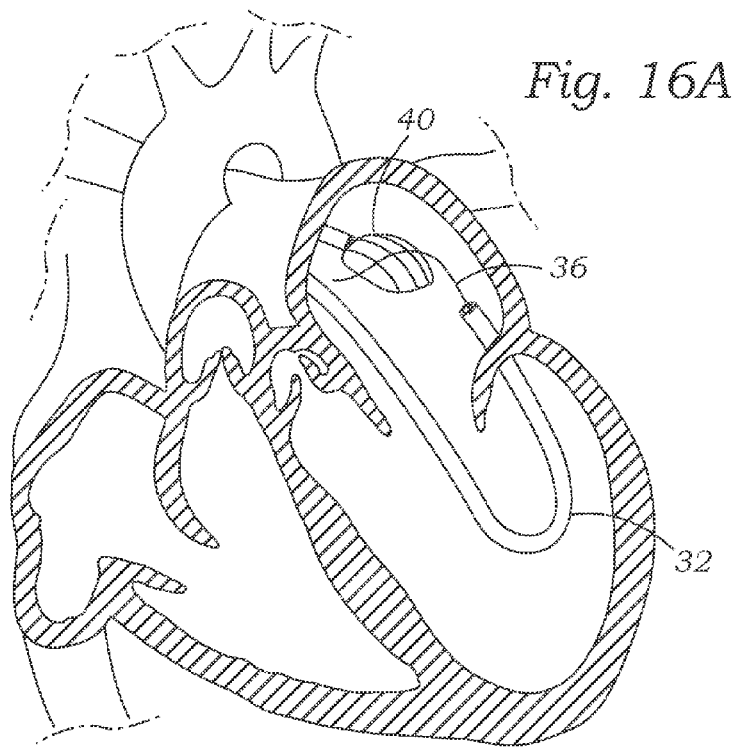
FIGS. 16A-16B are cross sections of a heart showing the implantation of a suture through the posterior mitral valve leaflet, according to another embodiment.
Figure 16B:
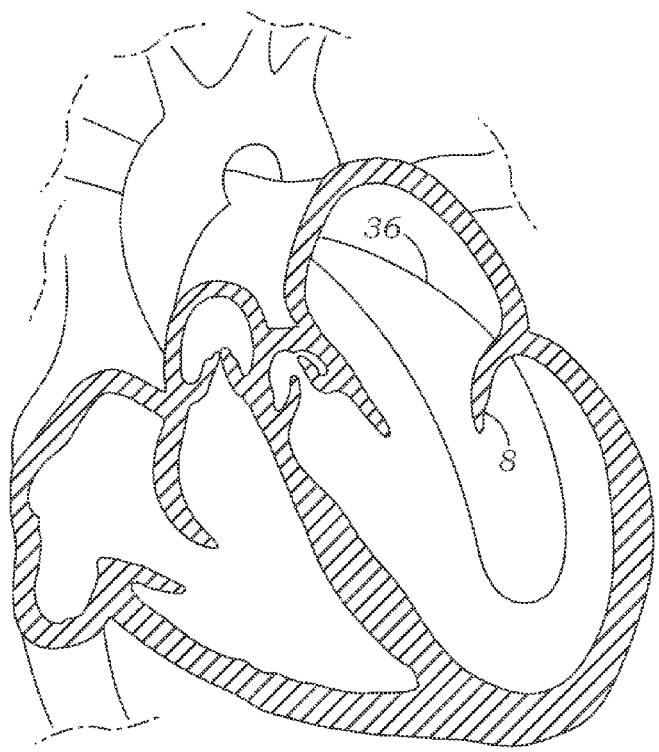

FIGS. 16A-16B shows an embodiment of another alternative method of delivering a suture or rail 36 into the heart, with the suture loop 36 extending through the atrial septum into the left atrium, then between the leaflets of the mitral valve into the left ventricle, and finally through the posterior leaflet 8 into the left atrium. The snare catheter 40 can be inserted transseptally (FIG. 8A) into the left atrium to capture the leading end of the suture 36 and bring it back outside the patient's body, leaving behind a suture loop as shown in FIG. 16B for subsequent device deployment. As discussed above, in some embodiments, the directionality of suture loop 36 delivery can be reversed (i.e., the suture enters the posterior leaflet from the atrial side).

Figure 17A:
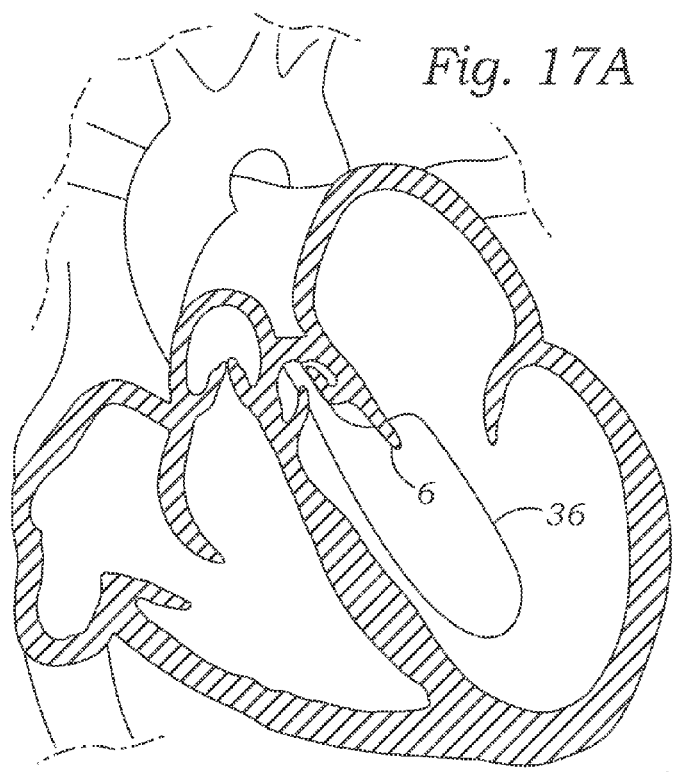
FIGS. 17A-17C are cross sections of a heart showing various ways of implanting a suture through the anterior mitral valve leaflet.
Figure 17B:
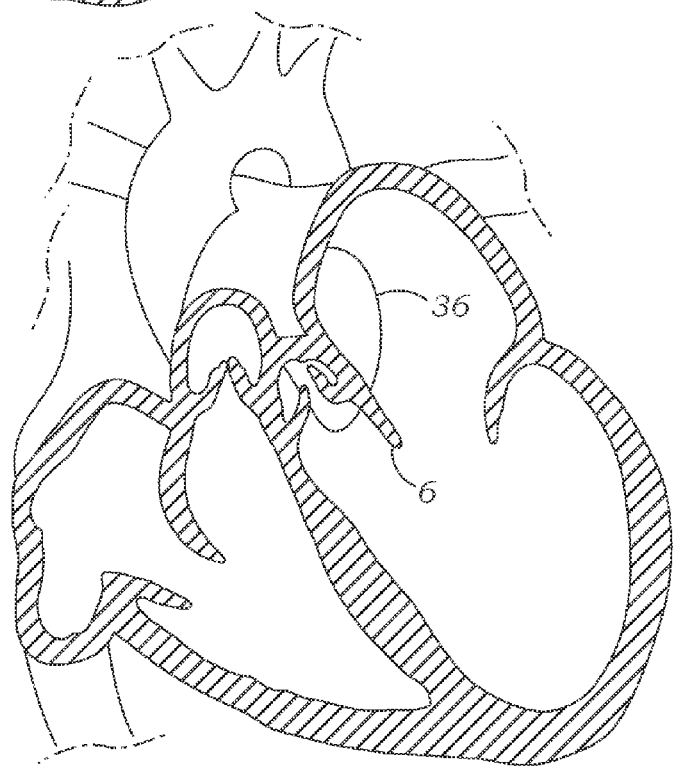
Figure 17C:
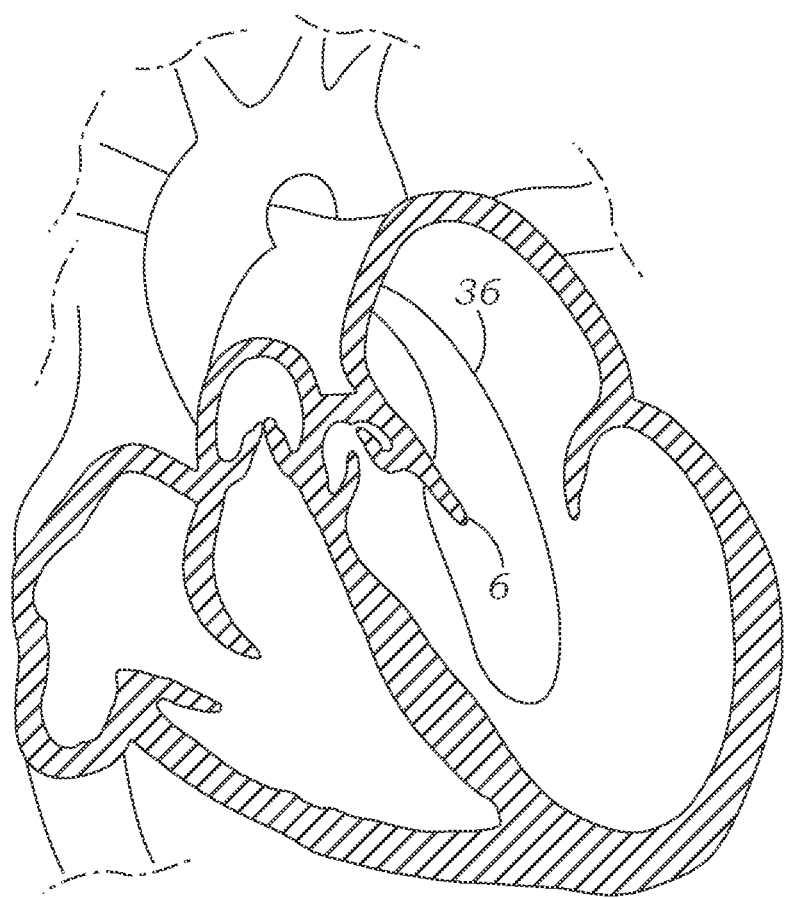

FIGS. 17A-17C show embodiments of exemplary suture loops for delivery of a device to an anterior leaflet 6 of the mitral valve. FIG. 17A shows a loop 36 that extends into the left ventricle via the aortic valve, then enters the left atrium between the leaflets of the mitral valve, then extends through the anterior leaflet 6 into the left ventricle, and exits the heart via the aortic valve. FIG. 17B shows a suture loop 36 that extends into the left ventricle via the aortic valve, then through the anterior leaflet 6 into the left atrium, and exits the left atrium transseptally. FIG. 17C shows a loop that enters the left atrium transseptally, extends through the anterior leaflet 6 into the left ventricle, then enters the left atrium between the leaflets of the mitral valve, and finally exits the left atrium transseptally.

FIG. 19 shows an alternative embodiment of a prosthetic device, indicated generally at 600. The prosthetic device 600 provides increased downward force on the free end of leaflet 8. The prosthetic device 600 includes a body 602 having a first end portion 604 and a second end portion 606. The body 602 can be positioned on the atrial surface of the native leaflet as shown and can be secured thereto with a suture or tether 608. The suture 608 can be secured at a first end to the first end portion 604 of the body 602, such as with a fastener 612 (as previously described), extends through the leaflet 8, and is secured at its opposite end to the second end portion 606 of the body.

The prosthetic device 600 further includes a stiffening member 610 placed at the subannular surface of mitral valve 8, such as by mounting or coupling the stiffening member to the suture 608. The stiffening member can comprise a segment of wire, a polymer and/or Nitinol band, or a polymer and/or Nitinol tube. Other biocompatible material of suitable stiffness may also be used. Generally speaking, the stiffening member 610 is relatively more stiff or rigid than the body 602 and the suture 608. In the illustrated embodiment, the stiffening member 610 comprises a tubular or cylindrical member (e.g., a polymer tube) that can be coaxially disposed around the suture 608. The stiffening member 610 can be sized such that an upper end 614 can contact or is in close proximity to the subannular surface of the native valve 8 and can have a upwardly curved lower portion 616 spaced from the free end of the leaflet 8.

The prosthetic device 600 can be implanted as described above in connection with FIGS. 18A-18F, but with the stiffening member 610 being threaded on the suture 608 adjacent the second end portion 606 of the body. Slack in the suture 608 in the suture may be adjusted (as described above in connection with FIG. 18F) to produce or less force in the ventricular direction. The downward force, in the ventricular direction, increases the efficacy of the device by increasing the overall stiffness the prosthetic device and the native leaflet, thereby promoting a better seal with the opposing native leaflet.

Figure 20:
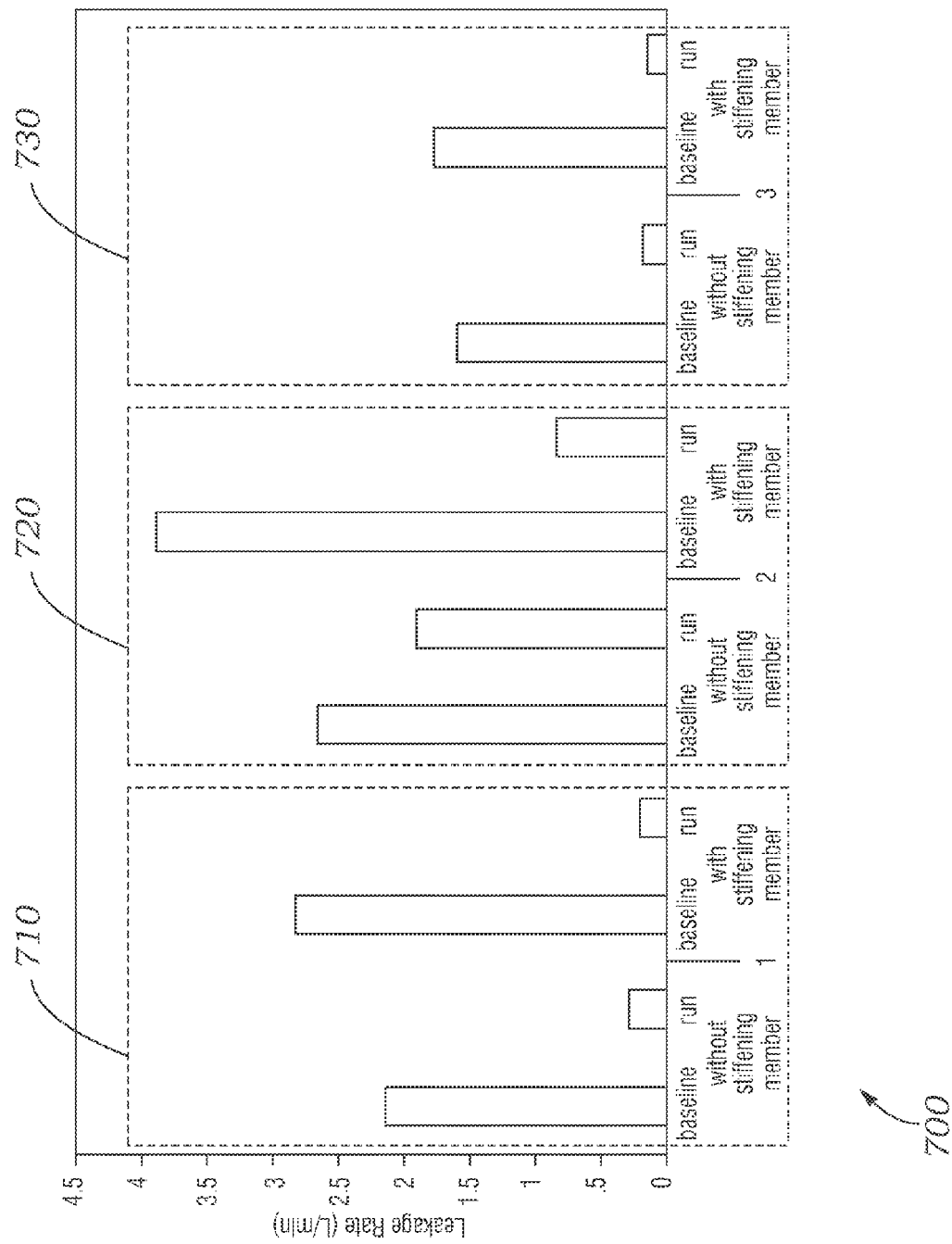
FIG. 20 shows decreased leakage rates for mitral valves fitted with prosthetics disclosed herein.

FIG. 20 shows comparison data before and after implantation of a prosthetic device 100 without a stiffening member and a prosthetic device 600 with a stiffening member 610. Graph 700 show results for three hearts with different degrees of mitral valve regurgitation, indicated at 710, 720, and 730. In the graph, "baseline" refers to regurgitation of the mitral valve without a prosthetic device, and "run" refers to regurgitation of the mitral valve in which either the prosthetic device 100 or the prosthetic device 600 has been implanted. As can be seen, in all three examples 710, 720, 730 use of the stiffening member further reduced regurgitation, with the most significant improvement occurring in example 720.

FIGS. 21-31 show additional embodiments of a suture-rail delivery assembly and methods to deploy a suture rail 800 through a native leaflet for subsequent implantation of a prosthetic device (e.g., a prosthetic device 100) on the native valve leaflet. The suture-rail delivery assembly in the illustrated embodiment generally comprises a steerable catheter 816, a crossing catheter 900, a needle wire 1000, and a snare catheter 1110.

Figure 21:
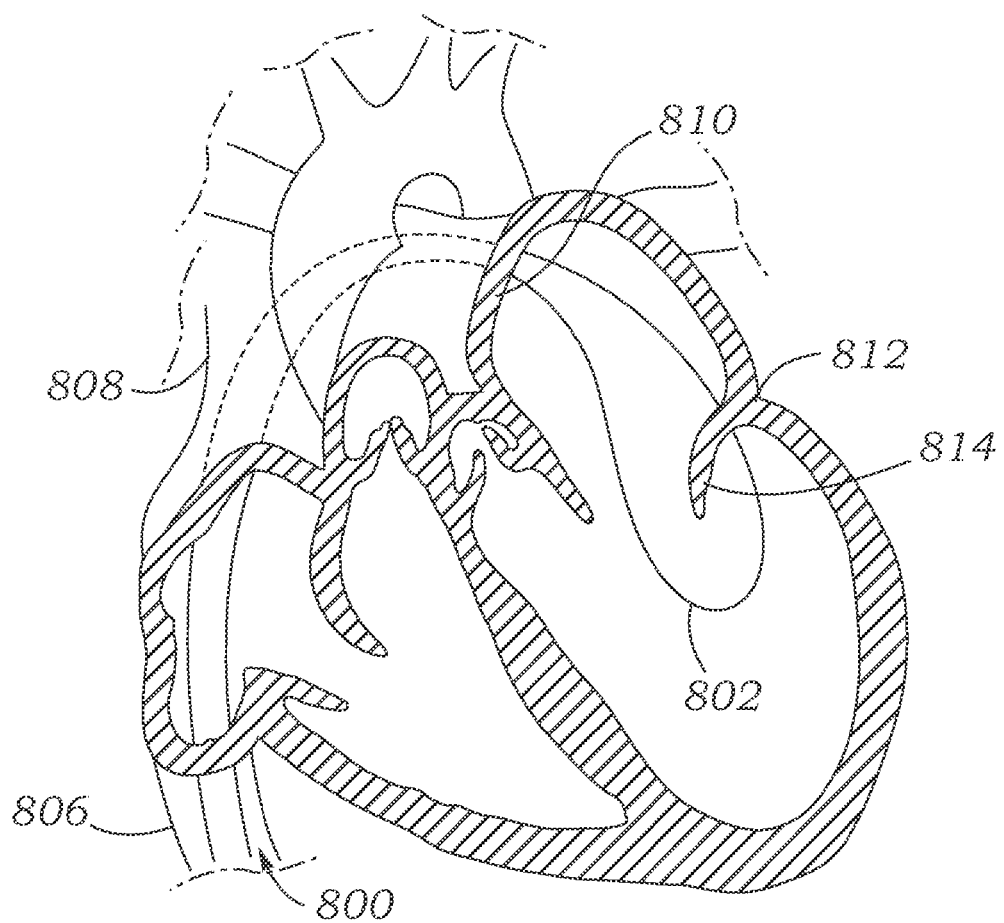
FIG. 21 shows a cross section of a heart with an example of a suture rail extending from the inferior vena cava transseptally through the posterior leaflet of the mitral valve.

FIG. 21 shows the suture rail 800 deployed within the heart. The suture rail 800 comprises a length of suture 802, for example 2-0 monofilament polyethylene, such as Deklene® II, or other suitable material or size. The suture 802 can extend from a suitable insertion point into the vasculature, such as the femoral vein, and extend to the heart 804. In the example shown in FIG. 21, the suture 802 extends from the peripheral vasculature through the inferior vena cava 806, into the right atrium 808, through the interatrial septum 810, through the atrial side of the posterior leaflet 814 adjacent the annulus 812 (desirably at the P2 position of the leaflet 814), around the free end of the leaflet 814 and then back into the peripheral vasculature following the same path from where it came, forming a loop extending through the leaflet 814.

The suture rail 800 may also originate in the high pressure vasculature and advanced to the heart in a retrograde direction, for example from the femoral artery, or be inserted via the superior vena cava, for example from the jugular vein. The suture 802 alternatively can extend through the annulus 812 (such as at a location adjacent the P2 position of the native leaflet) rather than through the leaflet itself.

Figure 22:
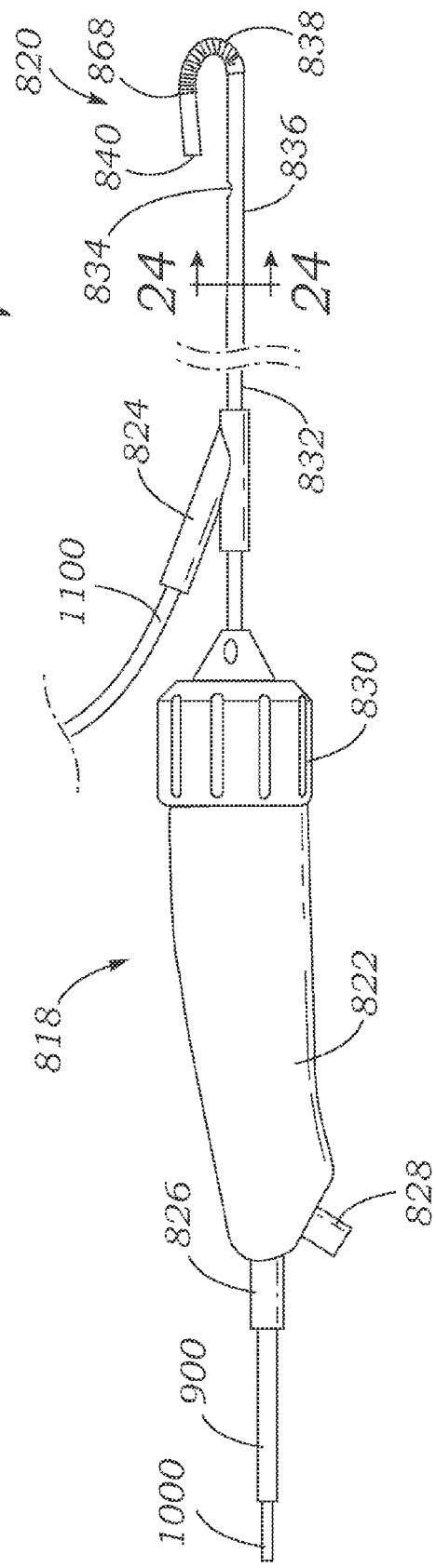
FIG. 22 is a side view of a delivery catheter for use in implanting a suture rail through native valve tissue, according to one embodiment.

FIG. 22 shows an embodiment of the steerable catheter 816, which is configured to extend into the left ventricle and deliver the suture rail 800 to an area below the posterior leaflet 814, as described in greater detail below. The steerable catheter 816 comprises a proximal end portion 818 and a distal end portion 820. The proximal end portion 818 of the steerable catheter 816 can comprise a handle 822, from which a shaft 832 extends. Mounted on the shaft 832 adjacent the handle 822 is an entry port, such as in the form of a y-connector 824 that is in communication with a side opening in the shaft and a respective lumen in the shaft. The y-connector 824 can be used to allow insertion of other tools, for example a snare catheter 1100 or guide wire, into the steerable catheter, as further described below.

The handle 822 can also comprise a plurality of other access ports, for example, ports 826 and 828 extending from the proximal end of handle 822. The access ports 826, 828 allow other tools or catheters to be inserted in lumens in the shaft 832. For example, as shown in FIG. 22, the crossing catheter 900 can be inserted into and through the steerable catheter 816 via the access port 826 and the needle wire 1000 can be inserted into and through a respective lumen of the crossing catheter. The handle 822 of the steerable catheter 816 can further comprise an adjustment mechanism 830 configured to adjust the curvature of a steerable section 838 of the shaft 832, as further described below.

Figure 24:
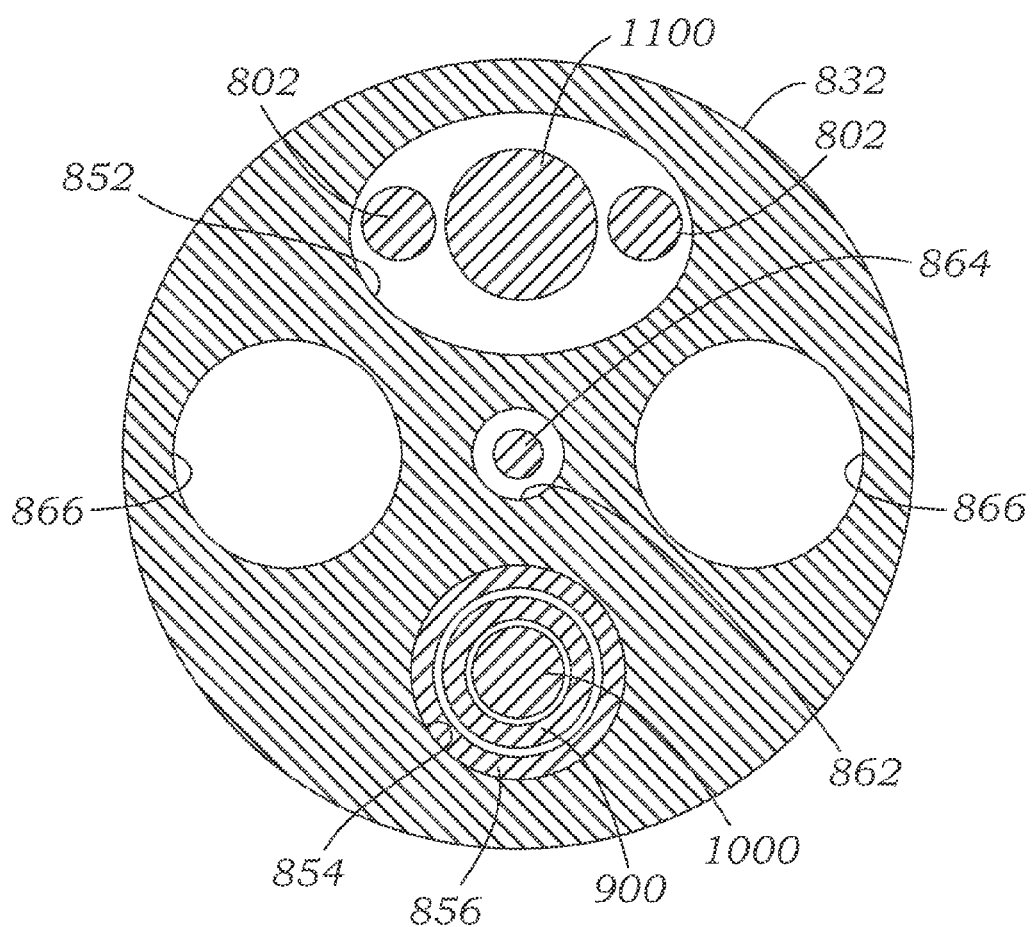
FIG. 24 is a cross sectional view of the delivery catheter of FIG. 22 taken along line 24-24.

FIG. 24 shows a cross-sectional view of the shaft 832, according to one embodiment. In the illustrated embodiment, the shaft 832 has five lumens, including a first side lumen 852, a second side lumen 854, third and fourth side lumens 866, and a central lumen 862. The first side lumen 852 (also referred to as a "snare-catheter lumen") is sized and shaped to receive the snare catheter 1100 and two sections of the suture 802. As shown, the snare-catheter lumen 852 can have an oval cross-sectional shape (in a plane perpendicular to the length of the shaft 832) to better accommodate the snare catheter 1100 and the two sections of the suture 802. The snare-catheter lumen 852 has a proximal end in communication with the entry port 824 and a distal end in communication with a side opening 834 formed in the distal end portion of the shaft 832 (FIG. 22).

The second side lumen 854 desirably extends the entire length of the shaft and has a proximal end in communication with the entry port 826 and a distal end forming a distal opening at the distal end of the shaft 832. Thus, as can be seen in FIGS. 22 and 24, the crossing catheter 900 can be inserted into the entry port 826 and advanced through the lumen 854, and the needle wire 1000 can be inserted into and advanced through the lumen of the crossing catheter 900. The lumen 854 can have an inner liner 856 that desirably extends the entire length of the shaft 832. The inner liner 856 can comprise, for example, a braid reinforced polymer extrusion having one or more extruded layers. The reinforcing braid can be a braided sleeve (e.g., a braided metal sleeve) extending coaxially over the one or more extruded layers. In one specific implementation, the inner liner 856 comprises a nylon 12 outer extrusion, a Pebax® inner extrusion, and a braided stainless steel sleeve extending over the outer extrusion, although other suitable materials can be used. The outer surface of the inner liner 856 can be fixedly secured to the inner surface of the lumen 854, such as with a suitable adhesive.

The central lumen 862 serves as a pull wire lumen that allows passage of a pull wire 864. The third and fourth side lumens 866 can be open lumens or "dummy" lumens 866, which can extend along diametrically opposing sides of the central lumen 864. The lumens 866 can be potted, or otherwise sealed, to maintain hemostasis. Alternatively, one or both lumens may be used to pass a guide wire or other tool into the shaft 832. The lumens 866 can aid in providing uniform stiffness about the central axis of the shaft 832, which in turn provides for a smoother torque response of the shaft when it is torqued while in a deflected state.

The pull wire 864 has a proximal end operatively connected to the adjustment mechanism 830 and a distal end fixed within the shaft 832 at a distal end 868 of the steerable section 838. The adjustment mechanism 830 is configured to increase and decrease tension in the pull wire to adjust the curvature of the steerable section 838 of the shaft 838. For example, rotating the adjustment mechanism 830 in a first direction (e.g., clockwise) increases the tension in the pull wire, which causes the steerable section 838 to bend or deflect into a curved configuration (as shown in FIG. 22). Rotating the adjustment mechanism in the opposite direction (e.g., counter-clockwise) reduces tension in the pull wire, which allows the steerable section 838 to return to its non-deflected configuration under its own resiliency. In the illustrated configuration, as shown in FIG. 22, the steerable section 838 can bend 180 degrees to permit navigation around the posterior leaflet 814 and positioning of the distal end 840 of the shaft 832 at the subannular groove of the posterior leaflet 814, as further described below.

The steerable section 838 can be constructed from a relatively more flexible material than the portion of the shaft proximal of the steerable section or otherwise can be constructed to be relatively more flexible than the portion of the shaft proximal to the steerable section. In this manner, the curvature of the proximal portion can remain substantially unchanged when the curvature of the steerable section is adjusted by application of tension from the pull wire. Further details of the construction of the handle and the adjustment mechanism are described in U.S. Patent Application Publication Nos. 2013/0030519, 2009/0281619, 2008/0065011, and 2007/0005131, which are incorporated herein by reference.

Figure 23:
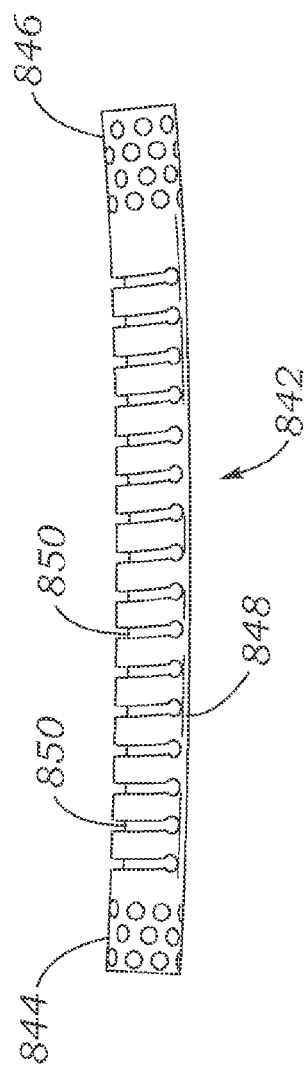
FIG. 23 is a side view of an embodiment of a laser cut tube that can be used in the steerable section of the delivery catheter shown in FIG. 22.

The steerable section 838 can comprise a slotted metal tube 842 (FIG. 23) covered by a polymer sleeve or outer layer. As shown in FIG. 23, the slotted tube 842 in the illustrated configuration comprises a proximal end portion 844, a distal end portion 846, an intermediate portion 848 extending between the proximal and distal end portions, and a plurality of circumferentially extending, axially-spaced slots 850 formed in the intermediate portion 848, which impart flexibility to the steerable section. The tube 842 can be made of Nitinol or another suitable biocompatible metal with sufficient stiffness. The tube 842 can be formed, for example, by laser-cutting the slots 850 in a tubular piece of metal. The distal end of the pull wire 864 can be affixed to the distal end portion 846 of the tube, such as by welding. Except where the distal end of the pull wire 864 is affixed to the distal end portion 846, the pull wire can be "free-floating" within the much larger lumen of the tube 842, meaning that the pull wire can easily slide relative to the inner surface of the lumen with minimal friction, thereby preventing or at least minimizing kinking of the pull wire.

A conventional steerable catheter has a pull wire located within a pull wire lumen that is offset to one side of the central longitudinal axis of the catheter. A drawback of this design is that the catheter suffers from a phenomenon known as "whipping" when it is torqued or rotated relative to its central longitudinal axis to adjust the rotational position of the distal end portion of the catheter while it is in a contoured configuration following the contour of the anatomical pathway through which the catheter extends. When the catheter is rotated in this contoured configuration, the pull wire exerts uneven forces along the length of the delivery device, which causes the delivery device to become unstable and spring back to its non-torqued, low energy state.

As noted above, the pull wire 864 extends through a centrally located lumen 862 that extends along the central longitudinal axis of the shaft 832. Advantageously, placing the pull wire in a centrally located lumen prevents the so-called "whipping" phenomenon of the shaft when a torquing force is applied to shaft, allowing for controlled 360-degree torquing of the shaft 832; that is, the distal end of the shaft can be rotated relative to the central longitudinal axis to any position through 360 degrees in three-dimensional space.

FIG. 25 shows details of the construction of a specific implementation of the shaft 832. In the illustrated configuration, the shaft 832 comprises a first section 870, a second section 872, a third section 874, and a fourth section 876. The fourth section 876 includes a steerable section 838 and a tip portion 878 distal to the steerable section. The first section 870 can be connected to the handle 820 (not shown in FIG. 25). The first section 870 has a length $L_1$, which can vary depending on a patient's height or point of vascular access. The first section 870 can comprise a polymer extrusion formed from one or more layers of different material. In a specific implementation, for example, the first section 870 comprises an inner layer made of nylon or ProPell and an outer layer made of 72D Pebax® or ProPell.

The second section 872 has a length $L_2$, which in certain embodiments can be approximately 10-12 cm. The second section 872 can comprise a polymer extrusion formed from one or more layers of different material. In a specific implementation, for example, the second section 872 comprises an inner layer made of 72D Pebax® or ProPell and an outer layer made of 72D Pebax® or ProPell.

The third section 874 has a length $L_3$, which in certain embodiments can be approximately 8 cm. The third section 874 can comprise a polymer extrusion formed from one or more layers of different material. In a specific implementation, for example, the third section 874 comprises an inner layer made of 55D Pebax® or ProPell and an outer layer made of 55D Pebax® or ProPell.

The shaft 832 can further comprise a braided outer layer or sleeve extending over one or more of the first, second, and third sections 870, 872, 874, respectively. In particular embodiments, the braided layer extends over the entire length of the first and second sections 870, 872, and extends over the third section 874 from a first location where the third section is connected to the second section to a second location just proximal to the opening 834. Thus, the third section 874 can be subdivided into a braided section 876 and an unbraided section 878. The braiding can comprise, for example, 304V stainless steel wire, with dimensions of approximately 1 mil by 5 mil. The braid can have sixteen carriers, with fifty-five picks per inch (PPI), in a standard 1-over-2-under-2 pattern. In alternative embodiments, the braided layer can extend the entire length or substantially the entire length of the shaft 832.

The steerable section 838 can comprises a slotted metal tube 842 and an outer sleeve or jacket made of, for example, 32D Pebax® or ProPell. In particular embodiments, the steerable section 838 has a bend radius of approximately 10-14 mm, and can bend up to at least 180 degrees. The outer jacket of the steerable section can be corrugated or ridged to facilitate bending. When the steerable section 838 is fully deflected such that the tip portion 878 extends substantially parallel to the third section 874, the distance $D_1$ from the distal most location of the steerable section 838 to the distal end 840 of the shaft can be approximately 2 cm. The longitudinal spacing between the distal end 840 of the shaft and the side opening 834 extends a distance $D_2$, which can approximately 1 cm.

FIG. 26 shows a crossing catheter 900, according to one embodiment, which is configured to cross or extend through a native leaflet or the annulus 812 of the mitral valve for subsequent placement of the suture 802. The crossing catheter 900 comprises an elongated shaft 902 that can have a lumen extending along its length for receiving the needle wire 1000. The crossing catheter 900 can further include a Luer fitting 904 connected to the proximal end of the shaft to facilitate insertion of the needle wire 1000 into the lumen of the shaft. The fitting 904 can also be configured to lock or retain the needle wire in place relative to the crossing catheter. The shaft 902 desirably has a pre-shaped or pre-curved distal end portion 906, which helps prevent or minimize kinking as it is advanced through the steerable section 838 of the steerable catheter when the steerable section is placed in the curved configuration.

In particular embodiments, the shaft 902 of the crossing catheter 900 has an outside diameter of about 0.27 inch, an inner diameter (the diameter of the lumen) of about 0.18 inch, and an overall length of about 69 inches or greater. The shaft 902 can comprise a polymer extrusion of one or more layers and can have a braided sleeve or outer layer extending over the extrusion. In one specific implementation, shaft 902 can comprise a multilayer extrusion comprising an inner layer made of ProPell, an intermediate layer made of nylon 12, and an outer layer made of ProPell. In an alternative implementation, the extrusion comprises a PTFE inner layer and the outer layer can contain barium sulfate. The barium sulfate can provide contrast during fluoroscopy. The braided outer sleeve can be similar to the braiding described above in connection with the shaft 832 of the steerable catheter, except that the crossing catheter shaft 902 desirably is stiffer. Thus, for example, a 5 mil by 25 mil 304V stainless steel wire can be used to form the braid. The braid PPI can be approximately 80-90. The distal end portion 906 can be pre-curved to a diameter of about 1 inch.

FIG. 27 shows an example embodiment of a needle wire 1000 for puncturing a native leaflet or the annulus 812 of the mitral valve 814. The needle wire 1000 comprises a proximal portion 1002, a distal portion 1004, and a sharpened tip 1006 configured to puncture native tissue, such as the annulus 812 or a leaflet 814. The proximal portion 1002 can be substantially straight in an un-deflected state and the distal portion 1004 can be curved in an un-deflected state. The distal portion 1004 can be, for example, shape-set or pre-curved to form a 360-degree curve having a diameter of, for example, about 19 mm. The overall length of the needle wire 1000 is preferably longer than the crossing catheter 900 to allow for insertion and manipulation. In one specific implementation, the needle wire 1000 has a length greater than 75 inches, is made of solid Nitinol, and has an outside diameter of approximately 0.16 inch to allow for insertion through the crossing catheter 900.

FIGS. 28 and 29 show different embodiments of a snare catheter that can be used for capturing an end of the suture 802 once it is passed through the native leaflet or the annulus 812. FIG. 28 shows an embodiment of a snare catheter 1100 comprising an elongated shaft 1102 and a snare loop 1104 extending from the distal end of the shaft 1102. The snare loop 1104 is radially expandable from a collapsed delivery state to an expanded, functional state (shown in FIG. 28) for capturing the end of the suture 802. In the delivery state, opposite sides 1108 of the loop 1104 are compressed toward each other such that the sides 1108 are generally straight and are in close proximity to each other such that the snare catheter 1100 can be advanced through the lumen 852 of the steerable catheter 816. When the snare loop 1104 is advanced from the distal opening 834 of the steerable catheter 816, the snare loop 1104 can expand to its functional size for capturing the suture 802, as further described below.

The snare loop 1104 can extend from the shaft 1102 at an angle less than 180 degrees, such as a 90-degree angle to facilitate placement of the snare loop at a desired position inside the heart when capturing the suture 802. The snare loop 1104 can be generally oval in shape and can have a radially protruding section 1106 diametrically opposed to the location where the loop is attached to the shaft. The protruding section 1106 helps the snare loop 1104 collapse from the expanded state to the delivery state when the opposite sides 1108 of the loop are pressed toward each other. In one specific implementation, the loop 1104 can be constructed from an 8-mil shape-set Nitinol wire. The loop 1104 can alternatively be constructed from gold plated tungsten, or other suitable materials that allow flexibility, shape memory, and/or contrast under fluoroscopy.

FIG. 29 shows an alternate embodiment of a snare catheter 1150 comprising an elongated shaft 1152 and a snare loop 1154 extending from the distal end of the shaft 1152. The snare loop 1154 can be shape-set such that it defines a distal protruding portion 1156 and a recessed portion 1158. In the expanded state of the loop (shown in FIG. 29), the recessed portion 1158 wraps or extends partially around an imaginary line extending along the central longitudinal axis of the shaft 1152. The recessed portion 1158 can promote suture capturing inside the body. Shapes for the snare catheters 1100, 1150 are not limited to those discussed above and shown in the figures. Other shapes for the snare loops, such as multiple loops, baskets, and hexagonal or asymmetrical loops, can be used.

Feeding a flexible suture through a relatively long catheter can be difficult. Because a suture is not ridged, advancing it through a catheter lumen can cause kinking at the insertion point, typically a luer fitting, and prevent deployment at the other end of the catheter. To prevent kinking, the suture 802 can be affixed to one end of a small diameter wire. The wire, which has much higher column strength than the suture, can be used to pull the suture distally through the steerable catheter 816. The wire can be, for example, a Nitinol wire having a diameter approximately the same as the diameter of the suture.

In certain embodiments, the distal end of the wire can be advanced through the crossing catheter 900 (which extends through the steerable catheter 816) and captured by the snare catheter 1100 inside the heart. The distal end of the wire can be retrieved by the snare catheter and pulled into the steerable catheter 816 via the distal side opening 834. The wire, along with the suture 802, can be pulled proximally through the lumen 852 of the steerable catheter 816 until the distal end of suture 802 exits the steerable catheter via the opening in the y-connector 824. Alternatively, a short length suture can be affixed to the distal end of the wire to aid in capturing by the snare catheter 1100.

In lieu of or in addition to the use of a thin wire to advance a suture through a suture through a catheter lumen, a suture-feeding device 1250 (FIG. 30) can be used to advance a suture through a catheter lumen. As shown in FIG. 30, the suture-feeding device 1250 in the illustrated embodiment comprises an inner stability tube 1252 and an outer feeding tube 1254, which can translate telescopingly along the inner stability tube 912 in the directions of double-headed arrow 1256. In use, the distal end of the inner stability tube 1252 is coupled to the proximal end of a catheter shaft 1260. In the illustrated embodiment, for example, the inner stability tube 1252 can be connected to a luer fitting 1258 disposed on the proximal end of the catheter shaft 1260. Alternatively, the distal end of the inner stability tube 1252 can be removably affixed to the luer fitting 1258 with a tuohy borst adapter or can be connected directly to the proximal end of the catheter shaft 1260.

The inner diameter of the outer feeding tube 1254 can be slightly larger than the outer diameter of the inner stability tube 1252. The inner diameter of the stability tube 1252 is preferably slightly larger than the outer diameter of the suture 802.

In use, the outer feeding tube 1254 can be placed around inner stability tube 1252 and a suture 802 can be fed into the inner stability tube 912 and into the catheter shaft 1260. The feeding tube 1254 is positioned such that a distal portion 1262 surrounds the inner stability tube 1252 and a proximal portion 1264 surrounds a portion of the suture 802, as depicted in FIG. 30. The proximal portion 1264 can be pinched, for example, using fingers, a hemostat, or other suitable tool, such that the proximal portion is compressed against and engages the suture. The feeding tube 1254 is then advanced distally over the inner tube 1252, thereby pushing the suture 802 further into the catheter shaft 1260. After advancing the suture, the pinching force on the outer feeding tube 1254 can be released and the feeding tube is retracted to the distal position to repeat the process of engaging and advancing the suture 802 through the catheter shaft 1260.

In one specific implementation, the suture-feeding device 1250 can be connected to the crossing catheter 900 and used to advance a suture through the lumen of the crossing catheter shaft 902 into the heart.

FIGS. 31A-31J show cross-sections of a heart showing the implantation of the suture-rail 800 (for example, via a transseptal approach) through the posterior leaflet 814, using the suture-rail delivery assembly of FIGS. 21-30, for subsequent introduction of a prosthetic device (e.g., prosthetic device 100) into the heart.

Figure 31A:
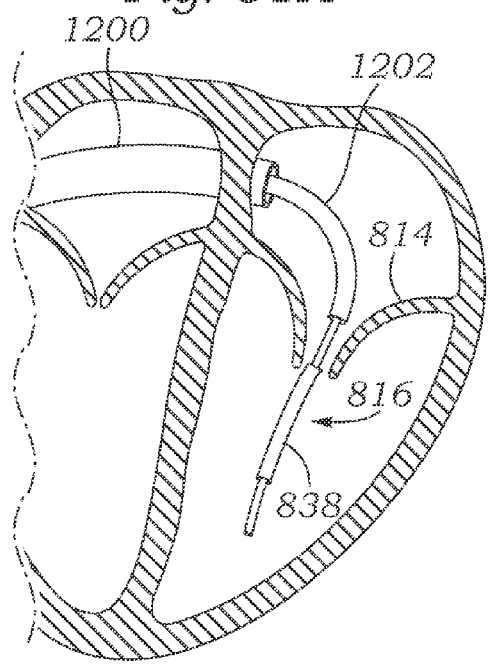
FIG. 31A-31H show cross sections of a heart showing the implantation of a suture rail through the posterior leaflet of the mitral valve leaflet using the tools shown in FIGS. 22-29.

FIG. 31A shows the delivery of a first, outer catheter 1200 in an antegrade direction into the right atrium (via the superior or inferior vena cava), through the interatrial septum and into the left atrium. A second, intermediate catheter 1202 is advanced through the first catheter 1200 into the left atrium and directed downwardly to an area above the native mitral valve leaflets. The first catheter 1200 and/or the second catheter 1202 can have steering mechanisms configured to control the deflection of the catheters to assist in advancing the catheters into the left atrium. Alternatively, the distal end portions of the first catheter 1200 and/or the second catheter 1202 can be pre-curved to assume the curved shapes shown in FIG. 31A. The steerable catheter 816 can then be advanced through the second catheter 1202 and the native mitral valve leaflets until the steerable portion 838 is advanced into the left ventricle downstream of the native valve leaflets.

Figure 31C:
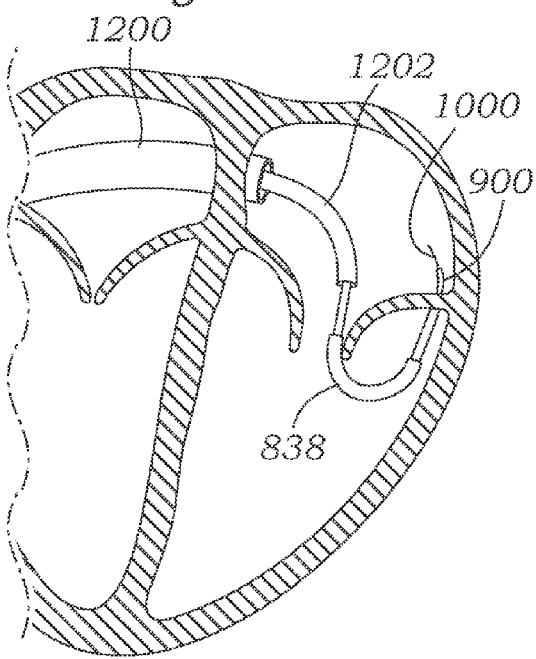
Figure 31B:
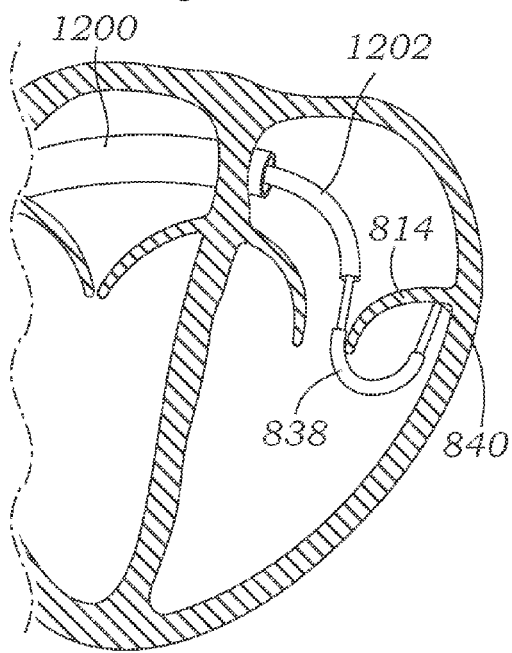

Referring to FIG. 31B, the steerable portion 838 is then deflected and torqued as needed to position the distal end 840 of the steerable catheter 816 against the subannular groove of the native leaflet 814. In the example shown, the steerable portion 838 wraps around the posterior leaflet 814 and does not extend deep into the ventricle. With the distal end 840 positioned against the subannular groove, the crossing catheter 900 and the needle wire 100 can be advanced through the lumen 854 (FIG. 24) of the steerable catheter 816. Alternatively, the crossing catheter and needle wire can be inserted into the steerable catheter before deflection and positioning of the distal end 840 of the steerable catheter 816.

As shown in FIG. 31C, the crossing catheter 900 and the needle wire 1000 are advanced in the distal direction until the crossing catheter and the needle wire puncture and extend through the native leaflet 814 into the left atrium. The crossing catheter and the needle wire can be locked axially relative to each other (e.g., at their proximal ends) with the needle wire extending slightly beyond the distal end of the crossing catheter to prevent relative movement between these two components in the axial direction as they are advanced through the native leaflet. As noted above, the crossing catheter 900 and the needle wire 1000 can have curved distal end portions that curve away from the atrium wall to avoid trauma to adjacent tissue. The curvature of the crossing catheter 900 also helps direct the suture 802 back toward the portion of the steerable catheter 816 in the left atrium, as further described below.

Figure 31D:
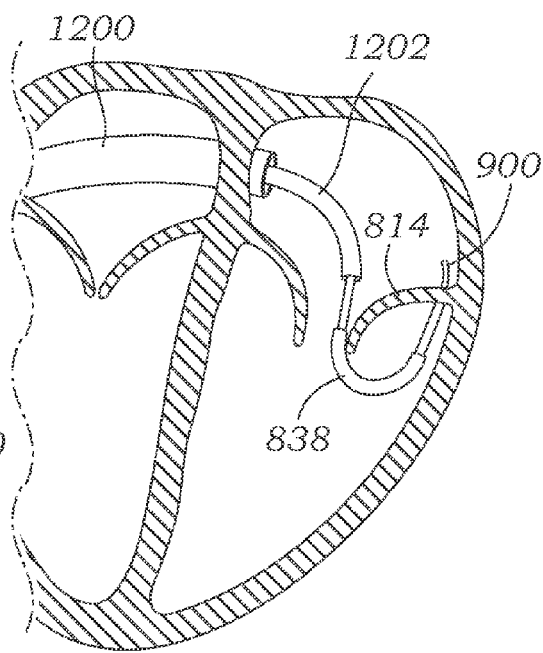

Once the crossing catheter 900 is advanced through the native leaflet 814, the needle wire 1000 can be unlocked from the crossing catheter and removed from the body, leaving the crossing catheter in place within the heart, as shown in FIG. 31D.

Figure 31E:
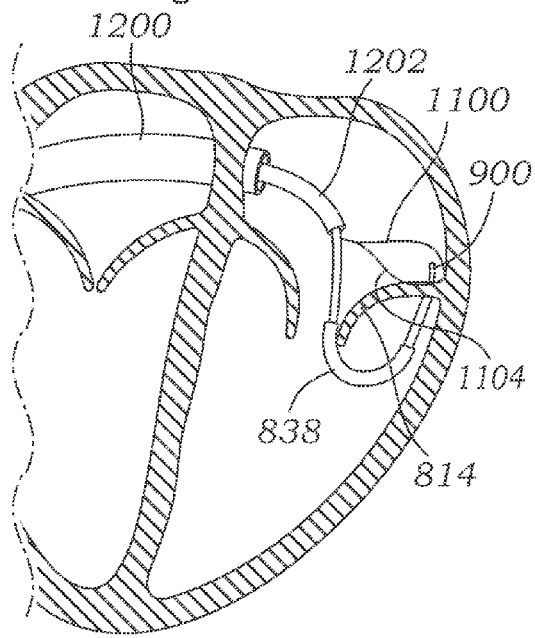
Figure 31F:
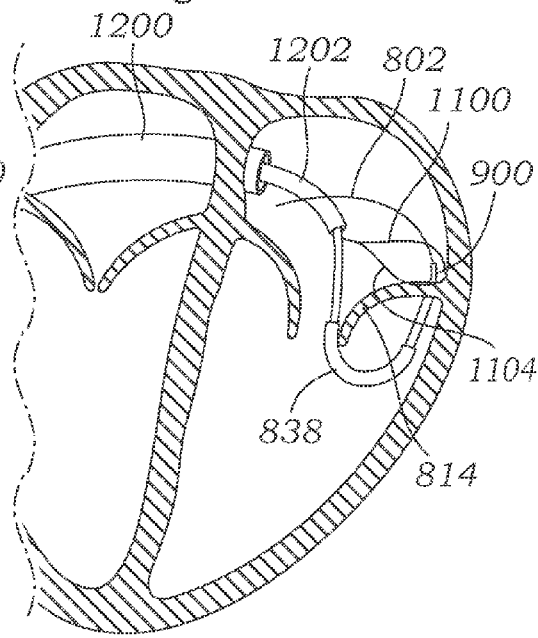

Referring to FIG. 31E, the snare catheter 1100 can then be advanced through the lumen 852 (FIG. 24) of the steerable catheter until the snare loop 1104 emerges from the distal side opening 834 into the left atrium. The snare loop 1104 can be positioned around the distal end portion of the crossing catheter 900, as depicted in FIG. 31E. With the snare loop 1104 positioned around crossing catheter 900 on the atrial side of the native leaflet 814, the suture 802 can be advanced through the crossing catheter 858 until it extends beyond the crossing catheter and through the snare loop 1104 in the left atrium, as shown in FIG. 31F.

Figure 31G:
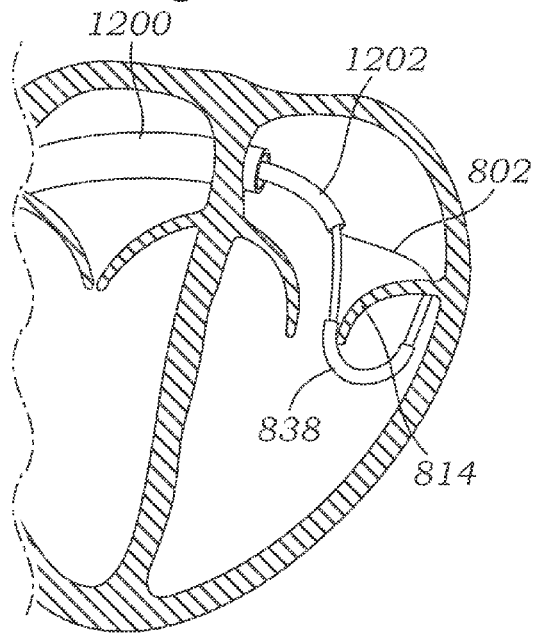

With the suture 802 extending through the snare loop 1104, the snare catheter 1100 can be retracted back into the steerable catheter 816, drawing the suture 802 proximally into the distal side opening 834, as shown in FIG. 31G. The snare catheter 1100 can be fully retracted from the steerable catheter, drawing the suture 802 outwardly from the port of the y-connector 824 (FIG. 22). The suture 802 can thus extend from outside the body, through the inner lumen of the crossing catheter 900, though the native leaflet 814 and back through the snare lumen 852 of the steerable catheter 816 with both end portions of the suture residing outside the body.

Figure 31H:
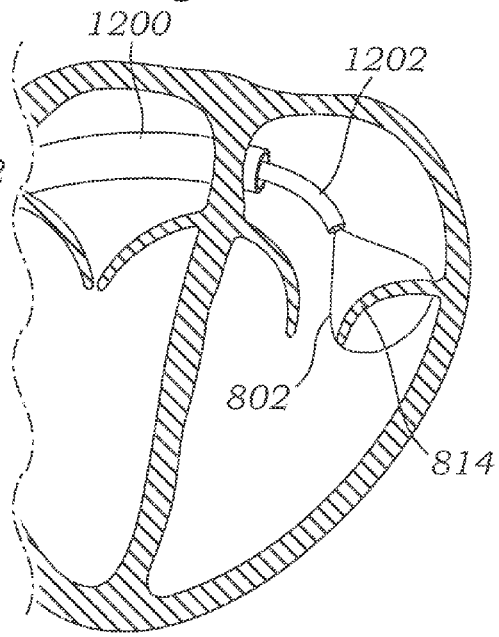
Figure 34:
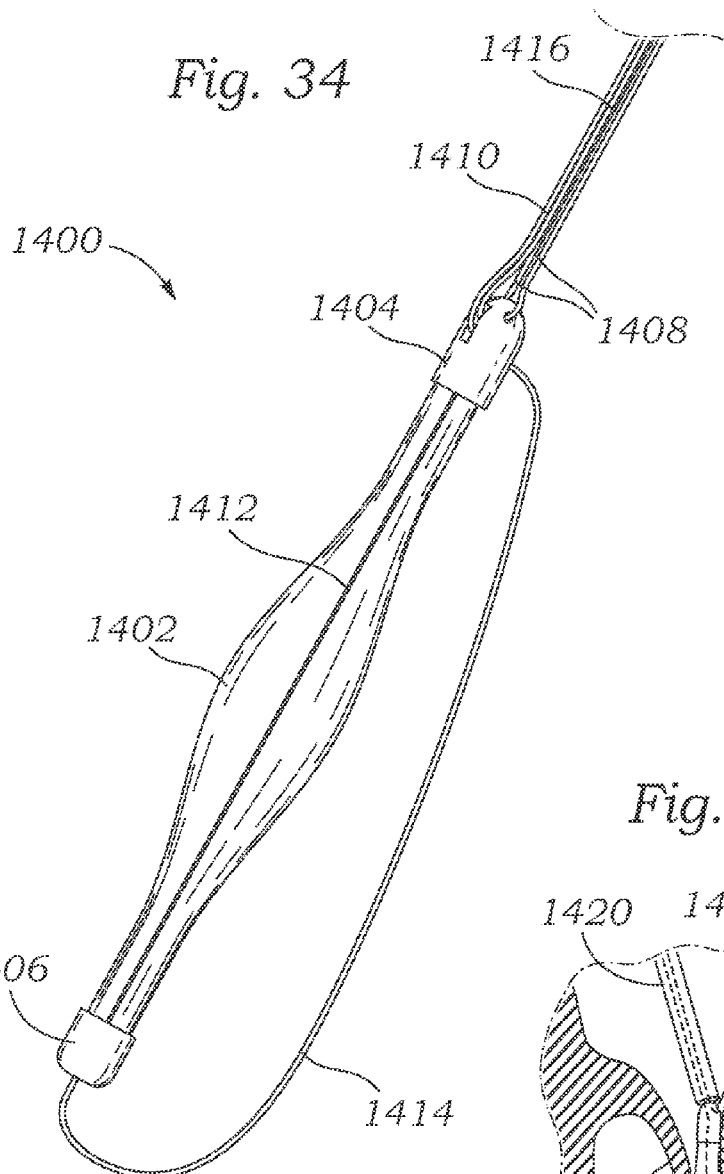
FIG. 34 is a perspective view of another embodiment of a prosthetic device for treating mitral valve regurgitation shown being advanced along a suture rail.

The crossing catheter 900 can then be retracted and removed from the steerable catheter 816, leaving the suture 802 in place within the heart, as shown in FIG. 31H. The first catheter 1200 and the second catheter 1202 can be left in place within the left atrium for subsequent delivery and implantation of a prosthetic device on the native leaflet.

FIGS. 32A-32D and 33A-33B illustrate another exemplary prosthetic device 1300, which can be used to augment a heart valve leaflet to improve valve coaptation and treat valve regurgitation. As described elsewhere herein, the device 1300 can be secured to and/or around a heart valve leaflet, such as a mitral valve leaflet, to add bulk to the leaflet and/or extend the length of the leaflet, which can help the leaflet seal the heart valve and prevent or reduce regurgitation of blood through the valve. The device 1300 can be delivered and implanted using transcatheter techniques, as are described elsewhere herein, and can expand from a crimped delivery configuration to a functional configuration once positioned inside the heart.

The device 1300 includes a flexible, expandable body 1302, a first end portion 1304 coupled to one end of the body, and a second end portion 1306 coupled to the other end of the body. The body 1302 can comprise a generally tubular structure defining an internal lumen extending from the first end portion 1304 to the second end portion 1306. As used herein, the term "tubular" means that the body has an annular cross section (in a plane perpendicular to the length of the body) that defines a lumen and does not necessarily require the body to have a true cylindrical shape. Indeed, the body 1302 in the illustrated embodiment has a wider intermediate portion that tapers in both directions toward the opposite ends of the body.

FIG. 32A shows a delivery configuration wherein the device 1300 is collapsed and has a minimal cross-sectional profile and can be contained within a delivery catheter. FIG. 32B shows a configuration wherein the body 1302 is released from its delivery catheter and has expanded to a larger cross-sectional profile. FIG. 32C shows the device 1300 curled up with the end portions 1304 and 1306 positioned adjacent to each other, which illustrates a configuration where the body 1302 is curled or wrapped around the free end of a leaflet with the end portions 1304 and 1306 being positioned on opposite sides of the leaflet. In the position of FIG. 32C, the end portions 1304 and 1306 can be secured to the leaflet, such as with one or more sutures or fasteners passing through the leaflet, to anchor the device 1300 to the leaflet. FIG. 32D shows the device 1300 in an implanted configuration with the body 1302 being further radially or laterally expanded, which allows the body to fill a gap between the native leaflets and reduce regurgitation between the native leaflets.

FIGS. 33A and 33B show two orthogonal side views of the device 1300, while FIG. 33C shows an end view. In its relaxed, natural state, the body 1302 can have a generally elliptical or flattened circular cross-sectional profile with a wider major lateral dimension (vertical dimension in FIG. 33C) and a smaller minor lateral dimension (horizontal dimension in FIG. 33C). This flattened profile allows the body 1302 to readily curl (see FIG. 32C) around a leaflet and lie with the flattened inner surface against the leaflet and with the major lateral dimension spread across the surface of the leaflet.

The device 1300 can include a passageway 1312 extending longitudinally through the body 1302 and through both end portions 1304 and 1306. The passageway 1312 allows the device 1300 to be advanced over a guide rail, such as a suture or cord, into the heart and around the target leaflet. As described elsewhere herein, a guide suture can be positioned through the leaflet before the device 1300 is delivered and the device 1300 can then be advanced over the guide suture and positioned with the first end portion 1304 on one side of the leaflet (e.g., the atrial side) and the second end portion 1306 on the other side of the leaflet (e.g., the ventricular side). The first end portion 1304 can include a lateral passageway 1308 and/or the second end portion 1306 can include a lateral passageway 1310, such that a guide suture or other guide rail can be passed transversely through the end portion rather than longitudinally through the end portion. For example, in the configuration of FIG. 32C, a guide suture can pass transversely through the passageway 1308 in first end portion 1304 and longitudinally through the passageway 1312 in second end portion 1306 (see also FIG. 36).

The body 1302 can comprise a tubular braided mesh made of Nitinol or other resiliently deformable and/or shapesettable material that can regain a desired shape when released from the delivery catheter inside the heart. The braided mesh also allows the body 1302 to expand laterally when it is shortened longitudinally, and contract laterally when in its lengthened longitudinally. In the delivery configuration, the braided mesh can have an elongated, narrow profile without wrinkling or folding, allowing it to fit efficiently within a narrow delivery catheter. When implanted around a leaflet, the braided mesh can have a shortened but laterally expanded profile. The braided mesh allows the body 1302 to move between these different configurations without substantial stretching of the material, such as could occur with a solid sheet of elastic material instead of a braided mesh.

The body 1302 can also include an outer layer covering the inner braided mesh to restrict or minimize blood flow through the body 1302. The outer layer can also comprise a braided mesh, or can comprise a more solid sheet of material. For example, the outer layer can comprise polyethylene terephthalate (PET), ultra-high-molecular-weight polyethylene (UHMWPE), polytetrafluoroethylene (PTFE, ePTFE), urethane, etc. The outer layer can allow some degree of blood porosity, but desirably restricts blood flow enough to prevent any substantial blood flow through the device when the heart valve is closed. The underlying inner braided mesh can serve more as a structural scaffold that is not necessarily non-porous, while the outer layer can be less structurally significant and serve more to restrict blood flow.

FIGS. 46A and 46B show an exemplary prosthetic device 1500 that includes a body comprising an inner tubular braided mesh layer 1506 and an outer tubular braided mesh layer 1504, along with end portions, or end caps, 1508 and 1510 secured to the ends of the mesh layers. The inner braided mesh 1506 can have larger openings between the strands of the mesh, and can be comprised of thicker, stronger strands to provide structure, whereas the outer braided mesh 1504 can comprise finer strands and smaller pores between the braided strands to restrict blood flow through the device. The outer braided mesh 1504 can extend the entire length of the body 1502 and be secured to the end portions 1508 and 1510 along with the inner braided mesh 1506. FIG. 46C illustrates the curled configuration of the device 1500 when a suture 1520 passing through the end portions 1508, 1510 is tensioned (as illustrated by arrows 1522, 1524). The outer braided mesh 1504 can shorten in length along with the suture 1520 and at the same time expand laterally without significant wrinkling or folding of the material, thereby enabling the outer surface to seal against the native tissue without undue blood leakage.

The end portions 1304, 1306 of the device 1300 can be more rigid than the body 1302 and can comprise various polymeric materials, such as polyether ether ketone (PEEK), or metal material such as Nitinol.

FIGS. 34-41 illustrate an exemplary prosthetic device 1400 that is similar to the device 1300 shown in FIGS. 32-33. The device 1400 includes a body 1402, a first end portion, or end cap, 1404 and a second end portion, or end cap, 1406. The body 1402 can have features similar to those describe for the body 1302 above.

The first end portion 1404 is secured to a tether 1408 that passes through a hole 1409 (FIG. 36) in the first end portion 1404. The tether 1408 can be used to apply a proximal force on the device 1400, such as to retain the device within a delivery catheter, to retract the device 1400 back into a delivery catheter, and/or to move the device proximally after being deployed.

Figure 35:
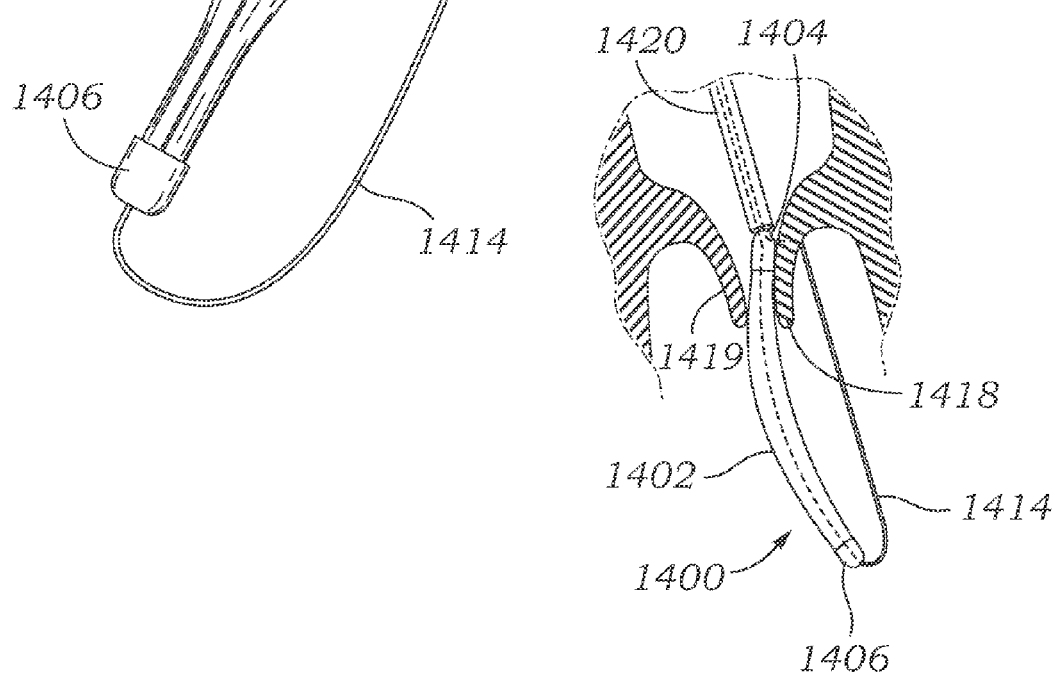
FIG. 35 is a cross sectional view of the mitral valve showing the implantation of the prosthetic device of FIG. 34.
Figure 36:
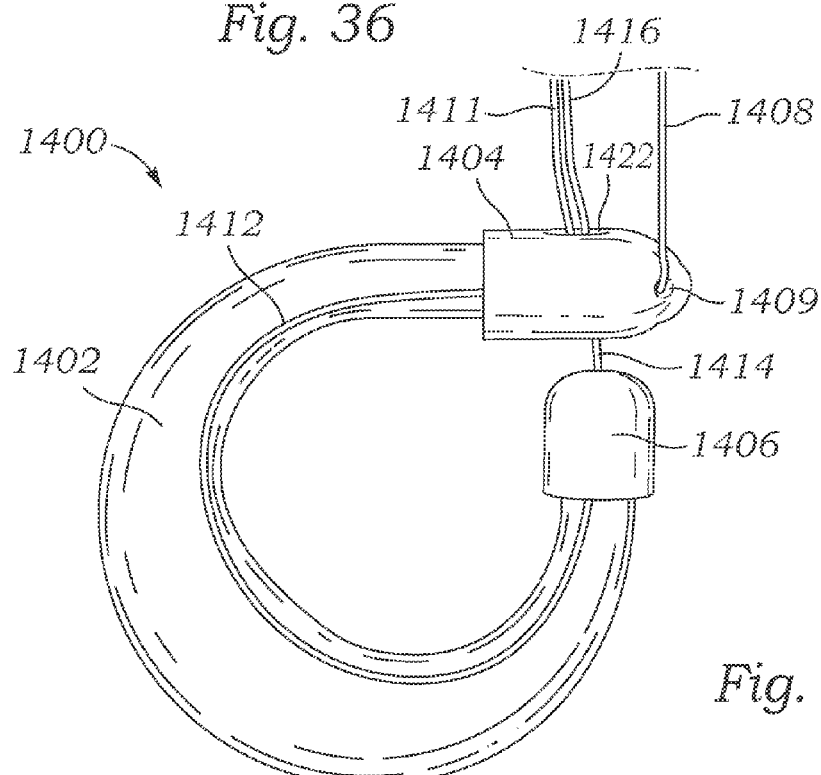
FIG. 36 is a side view of the prosthetic device of FIG. 34 shown in the deployed state.
Figure 37:
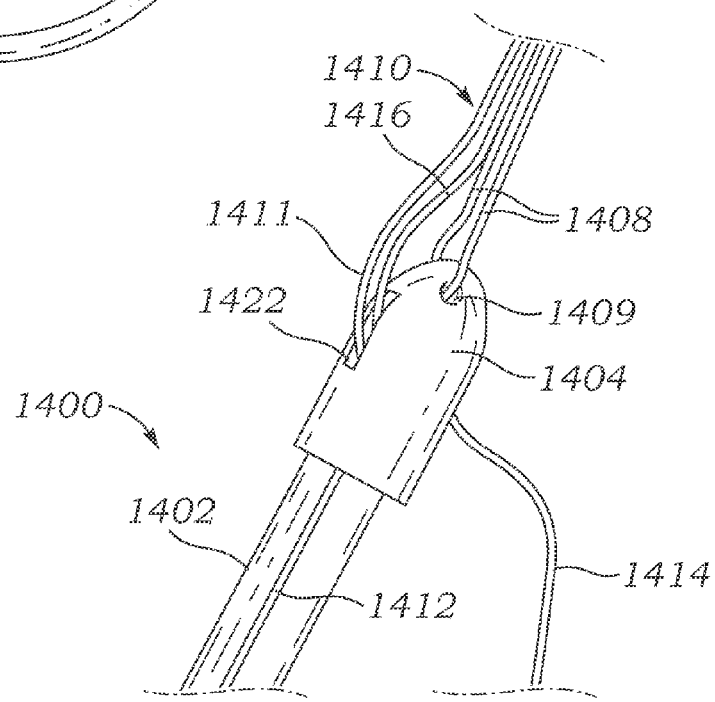
Figure 42:
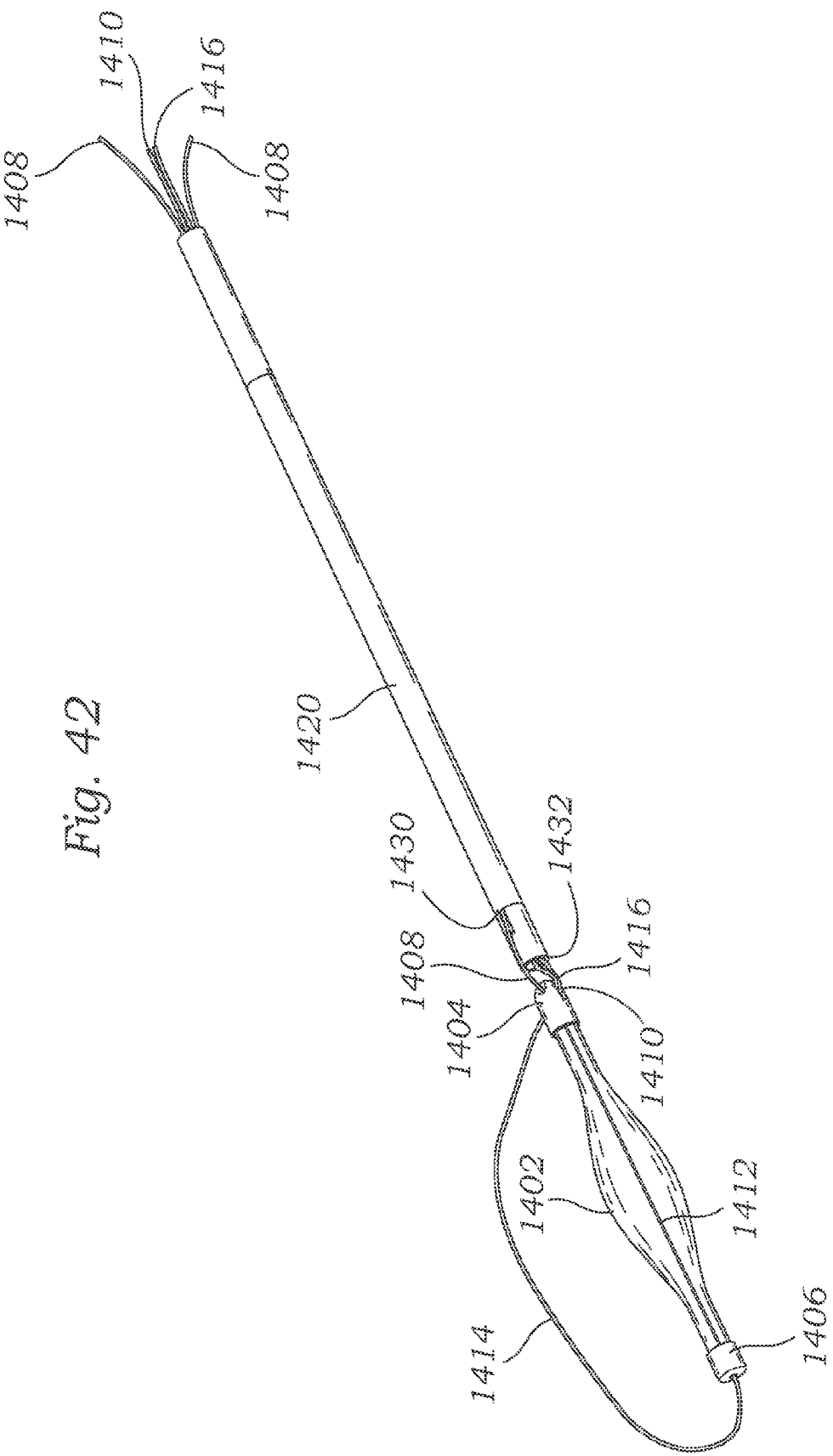
FIG. 42 is a perspective view of an embodiment of a delivery catheter and the prosthetic device of FIG. 34 coupled to the delivery catheter for delivery to a native leaflet.
Figure 43:
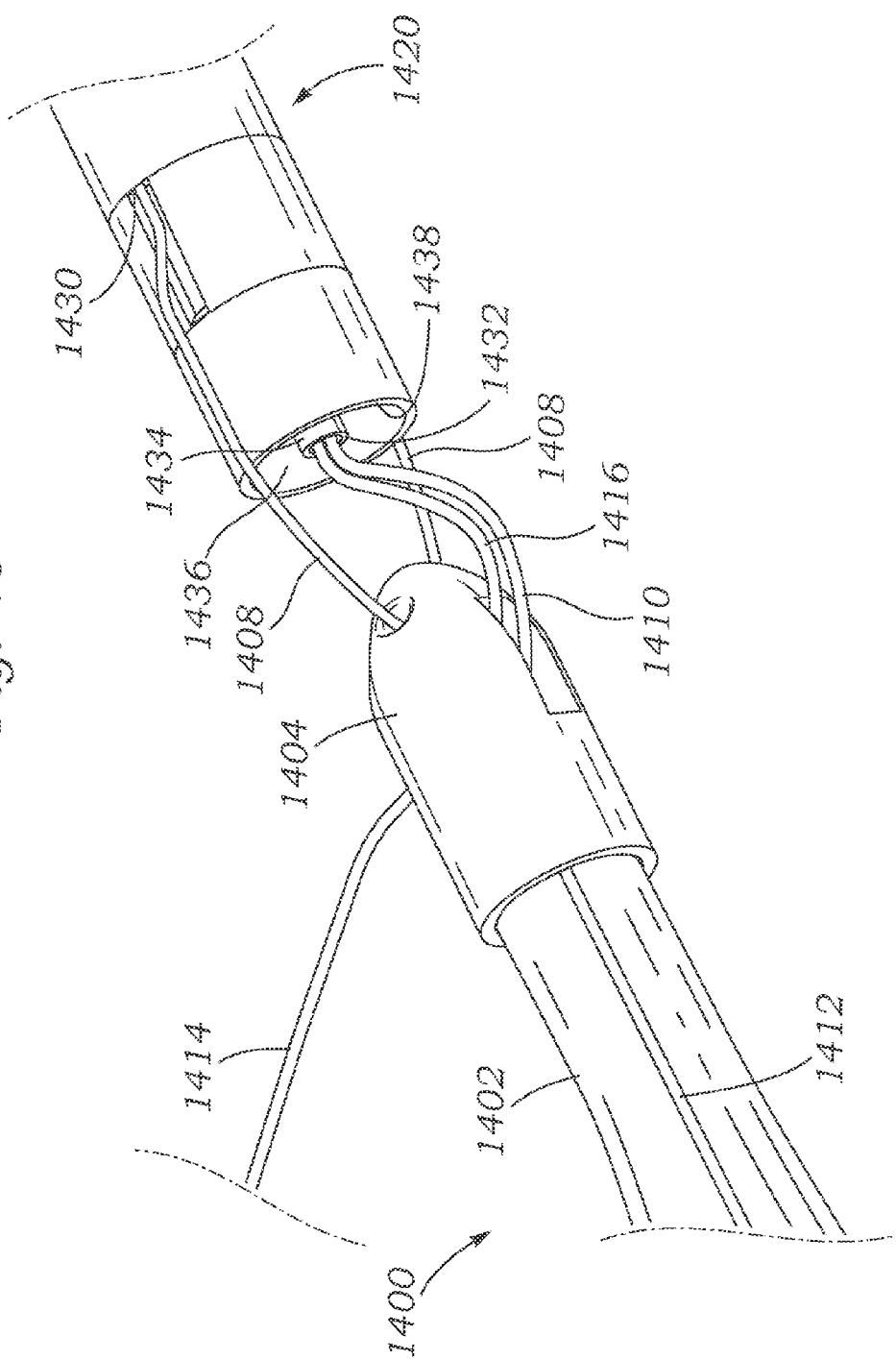
FIG. 43 is an enlarged view of the distal end portion of the delivery catheter and the prosthetic device shown in FIG. 42.

The first end portion 1404 can have internal passageways as illustrated in FIGS. 38 and 40 that route the passage of a guide suture 1410 through the first end portion 1404 and through the device 1400. The guide suture 1410 can be a previously implanted guide suture that extends through a native leaflet, as described in detailed above and shown in FIGS. 31A-31H. As shown in FIGS. 35 and 36, the guide suture 1410 can form a loop that extends through the prosthetic device 1400 and the native leaflet. The guide suture 1410 includes a first portion 1411 that extends outwardly from a proximally located delivery catheter 1420 (FIG. 42), passes through a first lateral opening 1422 in the first end portion 1404 and extends into the inside of the body 1402. A second portion 1412 of the guide suture 1410 extends through the body 1402 and through a longitudinal passageway in the second end portion 1406. A third portion 1414 of the guide suture 1410 extends from the second end portion 1406, through the native leaflet 1418, into a second lateral opening 1424 in the first end portion 1404, and out through the first lateral opening 1422. A fourth portion 1416 of the guide suture 1410 extends from the first lateral opening 1422 back into the proximally located delivery catheter 1420 (see FIGS. 42-45 for an exemplary delivery catheter). The proximal ends of the first portion 1411 and the fourth portion 1416 of the guide suture 1410 can be located outside of the patient's body.

As further shown in FIG. 38, the first end portion 1404 can also include a distal recess 1428 that receives and is secured to the proximal end of the body 1402. The recess 1428 communicates internally with the lateral openings 1422 and 1424.

During delivery of the device 1400, the body 1402 can be substantially straight or slightly curved, as shown in FIGS. 34, 35, 37 and 38. In this configuration, the two strands of the guide suture 1410 passing through the first lateral opening 1422 curve around a sloped surface 1423 (FIG. 38) of the first end portion and extend proximally, generally parallel with the longitudinal direction of the device 1400. The sloped surface 1423 provides a gradual curvature in the suture to minimize the risk of damaging the suture with a sharp right angled edge at the outlet of the first lateral opening 1422. Similarly, the third portion 1414 of the guide suture that passes through the second lateral opening 1424 can curve around a sloped surface 1425 that provides a gradual curvature in the suture to minimize the risk of damaging the suture with a sharp right angled edge at the outlet of the second lateral opening 1424.

When tension is applied to the guide suture 1410, such as by pulling proximally on one or both of first and fourth portions 1411, 1416, respectively, of the guide suture, the body 1402 begins to curl around the leaflet into the implanted configuration shown in FIGS. 36, 40, and 41. As length of the guide suture is taken out of the prosthetic device (causing the circumference of the loop extending through the body 1402 and the leaflet to decrease), the body 1402 curls up gradually. The distal end of the delivery catheter 1420 (see FIGS. 35 and 39) can be positioned against the first end portion 1404 to hold the first end portion in place against one side of the leaflet while the loop is decreased and the second end portion 1406 curls around against the opposite side of the leaflet (FIG. 41).

As shown in FIG. 40, when the body 1402 is curled into the deployed configuration, the second end portion 1406 can be oriented transverse to the first end portion 1404. In this configuration the portion 1414 of the guide suture can extend transversely through the two lateral openings 1422, 1424 of the first end portion, and can extend laterally from the first end portion into the delivery catheter along the other end of the guide suture 1410 and the tether 1408. As can be seen comparing FIGS. 38 and 40, the first end portion 1404 can rotate up to about 90° relative to the delivery catheter during the deployment of the device 1400.

FIG. 41 shows the device 1400 curled around a mitral leaflet 1406 during implantation, with the end portions 1404 and 1406 on opposite sides of the leaflet. In this position, the guide suture 1410 can be pulled and/or relaxed to cause the body 1402 to become tighter or looser around the leaflet and more or less bulky. For example, the guide suture can be tightened until the body 1402 expands far enough to contact and seal against the opposing leaflet 1419. The process can be facilitated by using imaging technology such as echocardiography and fluoroscopy to visualize the size and positioning of the device 1400, the native anatomy, and blood flow. For example, the body 1402 can be expanded until no substantial regurgitation is observed through the subject heart valve. The device 1400 can then be secured in that configuration by securing the guide suture, such as with a suture clip, suture lock, and/or knots, as described above.

FIGS. 42-45 show an exemplary delivery catheter 1420 that can be used to deliver and implant the device 1400 or similar devices. The catheter 1420 includes a central lumen through which the two strands of the guide suture 1410 pass and at least two outer side lumens 1430 spaced radially outward from the central lumen through which the two strands of the tether 1408 pass. The catheter 1420 can further include two additional outer side lumens 1431 to aid in providing uniform stiffness around the central longitudinal axis of the catheter. The outer lumens 1431 can be "dummy lumens" or can be used to pass instruments or other devices through the catheter into the patient's body. The delivery catheter 1420 includes a distal recess 1436 and distal outer rim 1438 that contact or are adjacent to the proximal end of the first end portion 1404 of the device 1400 during delivery into the heart.

Both the prosthetic device 1400 and the delivery catheter 1420 can be housed inside an outer catheter (not shown) during transvascular delivery into the heart (e.g., in the manner that outer catheter 50 is used to house inner catheter 52 and prosthetic device 100 in FIGS. 3A-3H during delivery of prosthetic device). Alternatively, the prosthetic device 1400 and the delivery catheter 1420 can be advanced through an outer catheter pre-inserted into the body such that a distal end of the outer catheter is positioned in the heart.

Figure 44:
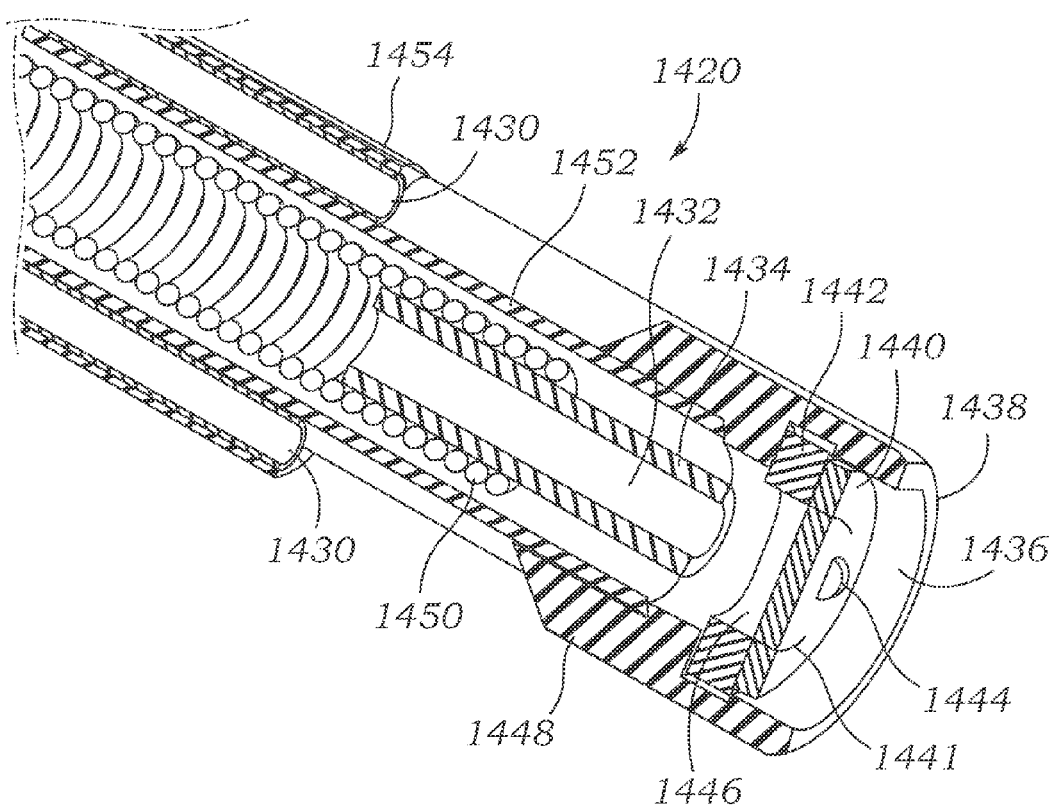
FIG. 44 is a perspective, cross sectional view of the distal end portion of the delivery catheter shown in FIG. 42.

As shown in FIG. 44, the delivery catheter 1420 can include at least one suture clip (or suture lock) 1440 positioned in the recess 1436 at the distal end of the catheter 1420. The suture clip 1440 can be generally disk shaped and can have one or more resiliently deformable flaps 1443 that can be deflected to open a passage 1441 that allows the strands of the guide suture 1410 to pass through the suture clip between the central lumen 1432 and the device 1400. The suture clip 1440 is positioned against an annular retainer 1442 that includes a projection 1444 that projects distally through the suture clip and holds the flap of the suture clip open during delivery to allow the guide suture to slide through the suture clip with minimal resistance during implantation. The annular retainer 1442 includes a central passage 1446.

The delivery catheter 1420 also includes a tubular pusher 1434 (FIG. 43, 44) that surrounds and/or defines the central lumen 1432 and is slidable longitudinally relative to the retainer 1442 and suture clip 1440. When the device 1400 is desirably positioned and the guide suture is desirable tensioned, the pusher 1434 can be advanced distally through the passage 1446 in the retainer 1442 to contact and push the suture clip 1440 distally apart from the retainer 1442, such that the projection 1444 comes out of the suture clip and the flap(s) 1443 of the suture clip can resiliently close against and engage onto the guide suture 1410. When released from the retainer 1442 and secured onto the guide suture 1410, the suture clip 1440 can exit out of the distal end of the recess 1436 of the delivery catheter 1420 as the delivery catheter is retracted proximally away from the implanted device 1400, leaving the suture clip 1440 engaged onto the two guide suture strands against the side of the first end portion 1404 of the prosthetic device 1400 adjacent the first lateral opening 1422 (see FIG. 40). FIG. 45B shows the delivery catheter 1420 after the pusher 1434 has moved distally and pushed out the suture clip 1440.

In FIGS. 44, 45A, and 45B, the pusher 1434 is shown extending only a short distance longitudinally from the distal end of the catheter 1420. In some embodiments, the pusher 1434 is attached to the inside of a wire coil 1450 of the catheter and the coil along with a coil cover layer 1460 can be moved longitudinally relative to the outer portions of the catheter to move the pusher 1434. The outer portions of the catheter 1420 can include an outer annular body or shaft 1454 defining the outer lumens 1430, 1431, one or more layers of material 1462, 1464 lining the inside of the outer shaft, and a distal outer body or tip portion 1448 that contains the retainer 1442 and the suture clip 1440. The inner layers 1462, 1464 can comprise an extruded polymeric layer or braided layer, such as described above in connection with the catheter 816 of FIGS. 22-25.

In alternative embodiments, the first end portion 1404 of the prosthetic device 1400 can include a suture locking mechanism that can engage the guide suture. This can eliminate the need to apply a suture clip from the delivery catheter or otherwise secure the guide suture, or can be used in addition to the application of a suture clip. A suture locking device can be located inside of or along the surface of the first end portion 1404 such that both strands of the suture 1410 pass through the suture locking mechanism. The suture locking mechanism can comprise a one-way restrictor that allows the suture strands to be pull proximally through the first end portion to tighten the suture within the body 1402, but prevents the suture strands from slipping back through the first end portion after implantation. In some embodiments, the suture locking mechanism can include a ratcheting mechanism. In some embodiments, the suture locking mechanism can be selectively releasable to allow a user to add slack back into the guide suture and then re-secure the locking mechanism.

FIGS. 47-49 illustrate devices that can be used to unwind and/or straighten two strands of a suture or other cord (e.g., the guide suture 1410) extending into a patient's vasculature. FIG. 49A illustrates a situation where a suture 1620 is looped at the left end and has two strands extending to the right. The looped end can represent a portion of a guide suture 802 or a guide suture 1410 that extends through a native leaflet (as depicted in FIG. 21 or FIG. 35, for example). In FIG. 49A, the two strands of the suture are twisted, which can inhibit the delivery of a device over the suture strands. The suture strands can become twisted in various ways, both inside the vasculature of a patient and outside of the patient.

FIGS. 47 and 48 show two exemplary devices 1600 and 1610 that can be passed over the twisted strands of the suture 1620 to untwist and straighten them. The device 1600 includes a solid outer body or shaft 1602, a single central lumen 1604 sized to accommodate both strands of the suture 1620, and two radially positioned lumens 1606 that create a weak spot along the length of the body 1602 to allow the body to be peeled apart into two halves, as shown in FIG. 49C. The device 1610 includes a solid outer body or shaft 1612, two separate inner lumens 1614 for each suture strand, and two outer lumens 1616 that similarly create a weak spot along the length of the body 1612 to allow the body to be peeled apart into two halves. The body 1602, 1612 can comprise any sufficiently torqueable and bendable material, such as an extruded polymeric material.

Using the device 1600 as an example (the device 1610 can equally be used in the same way), the free ends of the two suture strands can be inserted into the central lumen 1604 or into the two central lumens 1614 (as shown in FIG. 49A), and then the device 1600 can be advanced over the two suture strands (as shown in FIG. 49B) to untwist them. The untwisting of the suture strands can include rotation of the device 1600 such that the loop at the distal end of the suture can remain fixed and not need to rotate. The loop in the suture can extend through a leaflet or other tissue/object and be prevented from rotating to untwist the suture.

The free ends 1622 (FIG. 49C) of the suture strands can extend out of the proximal end of the device 1600 in the position shown in FIG. 49B, such that another catheter (e.g., containing the prosthetic device 1400 and delivery catheter 1420) can be advanced over one or both of the suture strands while the device 1600 is still on the suture strands. This other catheter can block the device 1600 from being pulled back proximally off of the suture strands as the other catheter is advanced distally. To remove the device 1600, the body 1602 can be peeled apart into two halves 1602A, 1602B (not necessarily equal is size) along the weak spots provided by the outer lumens 1606 (as shown in FIG. 49C). The peeling or tearing apart can occur outside of the patient's body. As the two halves 1602A, 1602B are peeled apart, the device 1600 can be pulled proximally over the suture strands out of the body until the entire device 1600 is out of the body and split into two parts that are removed from the suture strands and discarded, leaving the suture strands untwisted for the other catheter to be advanced over. The other catheter can be advanced over the suture strands at the same time as the device 1600 is being retracted and peeled apart, thereby preventing the suture strands from becoming twisted again.

FIG. 50 shows a prosthetic device 1700 for treating valve regurgitation, according to another embodiment. The prosthetic device 1700 can have an overall construction similar to the prosthetic device 1300 of FIGS. 32-33 and therefore can have an elongated body 1702 and first and second opposing end portions, or end caps, 1704,1706, respectively at opposite ends of the body. One or both of the first and second end portions 1704, 1706 can have one or more barbs 1708 that can provide enhanced frictional engagement with the native leaflet. In the illustrated embodiment, each of the first and second end portions 1704, 1706 has a plurality of barbs 1708. The barbs 1708 desirably have pointed ends that can penetrate the surface of the native leaflet to promote engagement of the end portions with the native leaflets.

FIG. 51 shows the prosthetic device 1700 implanted on a native leaflet. As shown, the barbs 1708 on the first end portion 1704 can engage and optionally penetrate the atrial surface of the native leaflet while the barbs on the 1708 on the second end portion 1706 can engage and optionally penetrate the ventricular surface of the native leaflet (the barbs are shown slightly spaced from the native leaflet for purposes of illustration). The prosthetic device 1700 can be further secured in place against the native leaflet with a suture and a fastener as described in detail above.

FIG. 52 shows a modification of the prosthetic device 1700 in which the second end portion 1706 includes one or more barbs 1708 and the first end 1704 includes one or more correspondingly shaped recesses 1710 shaped to receive tissue of the native leaflet. When implanted around a native leaflet, the barbs 1708 press tissue of the native leaflet into the recesses 1710 to promote anchoring of the prosthetic device. In certain embodiments, the barbs 1708 can be configured to penetrate completely through the native leaflet and extend into the recesses 1710.

In alternative embodiments, the first end portion 1704 can have one or more barbs 1708 and the second end portion 1706 can have one or more recesses 1710. Moreover, any of the embodiments disclosed herein can include one or more barbs on one or both ends of the prosthetic device, or one or more barbs on one end and one or more recesses on the other end.

FIGS. 53-54 shows a prosthetic device 1800, according to another embodiment, comprising an elongated body 1802 and first and second opposing end portions 1804,1806, respectively at opposite ends of the body. One or both of the first and second end portions 1804, 1806 can have one or more barbs 1808 that can provide enhanced frictional engagement with the native leaflet. As shown in the end view of the prosthetic device of FIG. 53, the end portion 1804, 1806 can have a flattened configuration so as to be able to lay flat against the surfaces of a native leaflet and therefore provide enhanced stability of the prosthetic device.

Figure 55A:
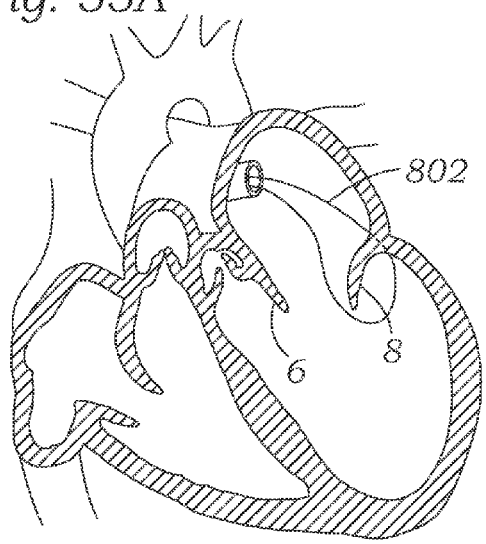
FIGS. 55A-55E show a method for implanting a prosthetic heart valve in the mitral position using a prosthetic device mounted on one of the native leaflets as a support structure for the prosthetic valve.
Figure 55B:
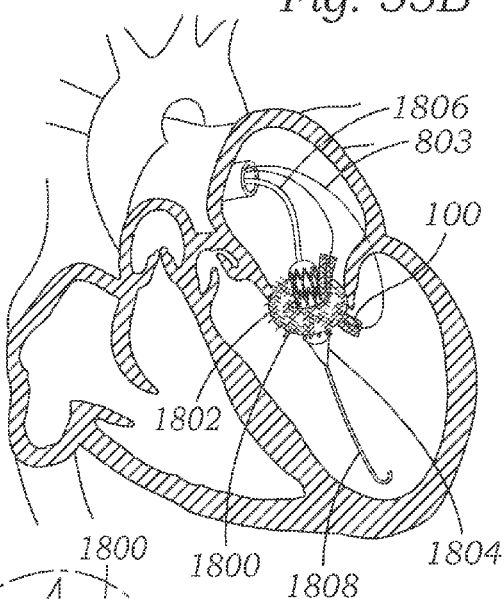

FIGS. 55A-55E illustrate a method for implanting a prosthetic heart valve in the mitral position using a prosthetic device mounted on one of the native leaflets as a support structure for the prosthetic valve. FIG. 55A shows a rail 802 implanted through the posterior leaflet 8 as previously described in detail above. FIG. 55B shows a first prosthetic device 100 partially deployed around the leaflet 8, which can be delivered to the native leaflet as previously described. The first prosthetic device 100 carries a second prosthetic device in form of a radially expandable support ring 1800. The first prosthetic device 100 in the illustrated embodiment can extend or loop through the support ring 1800 such that the two components are linked together similar to links of a chain. The support ring 1800 can comprise, for example, an annular stent formed from interconnected struts or can comprise a braided structure.

Figure 55E:
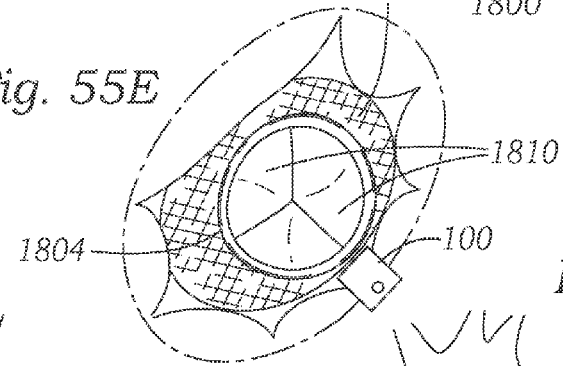
Figure 55C:
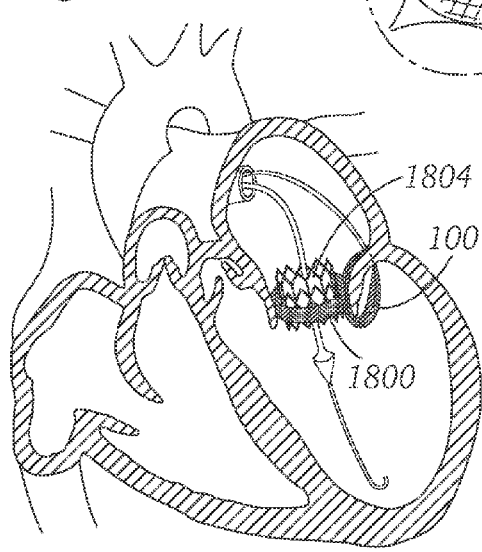
Figure 55D:
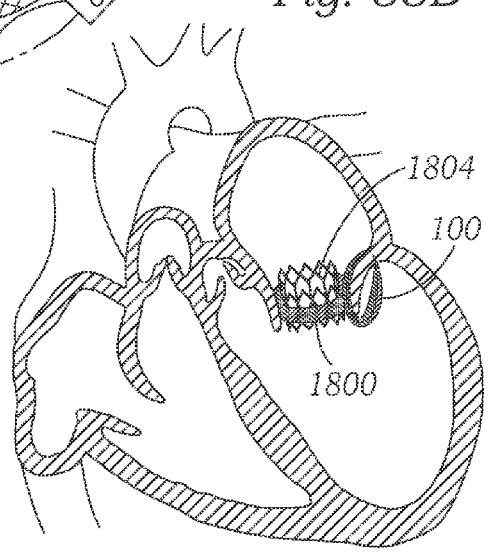

As shown in FIG. 55B, the support ring 1800 is positioned between the native leaflets and receives a transcatheter prosthetic heart valve 1804. The prosthetic heart valve 1804 can be mounted on a delivery catheter 1806, which can be advanced over a guidewire 1808. As shown in FIG. 55C, the first prosthetic device 100 can be fully deployed around the native leaflet and secured in place, and the prosthetic heart valve 1804 can be radially expanded against the inner surface of the support ring 1800. The prosthetic heart valve 1804 can be held in place by the frictional engagement between the prosthetic valve and the support ring. The outer surface of the support ring 1800 have a plurality of barbs or tissue engagement members 1802 that can engage the anterior leaflet 6 and/or other surrounding tissue to help anchor the support ring 1800 in place between the two native leaflets. FIGS. 55D and 55E and side and top views, respectively, showing the prosthetic valve 1804 expanded and held in place within the support ring 1802 with all delivery devices retracted from the heart. As shown in FIG. 55E, the prosthetic valve can have prosthetic leaflets 1810 that regulate the flow of blood through the prosthetic valve.

The prosthetic heart valve 1804 can be a self-expandable prosthetic valve or a plastically-expandable heart valve, as known in the art. A self-expandable heart valve can have a self-expandable frame made of a shape-memory material (e.g., Nitinol) that can radially expand to its functional size when released from a delivery sheath, as known in the art. A plastically-expandable heart valve can have a frame made of a ductile or plastically-expandable material (e.g., stainless steel or cobalt chromium alloy) that can be expanded to its functional size by a balloon or other expansion device, as known in the art. Examples of such prosthetic heart valves that can be used in the disclosed method and assembly are disclosed in U.S. Patent Application Publication Nos. 2012/0123529 and 2012/0239142, which are incorporated herein by reference.

Figure 56A:
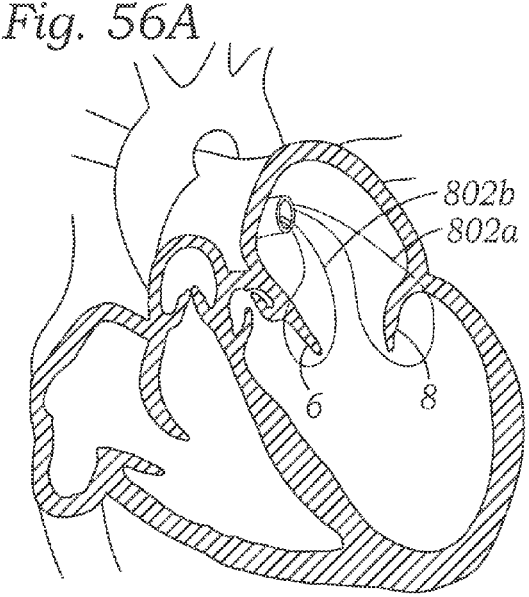
FIGS. 56A-56E show another method for implanting a prosthetic heart valve in the mitral position using two prosthetic devices mounted on the native leaflets as a support structure for the prosthetic valve.
Figure 56B:
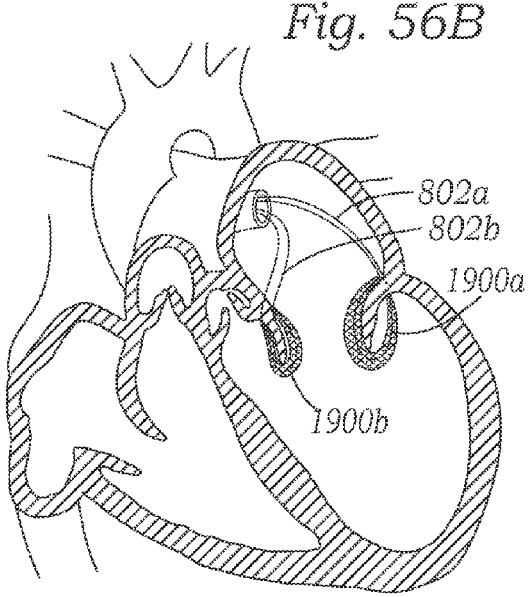

FIGS. 56A-56E show a method for implanting a prosthetic heart valve in the mitral position using multiple prosthetic devices mounted on the native leaflets as support structure for the prosthetic valve. In this method, a first rail 802a is implanted through the posterior leaflet 8 and a second rail 802b is implanted through the anterior leaflet 6, as shown in FIG. 56B. A first prosthetic device 1900a is implanted around the posterior leaflet 8 via the first rail 802a, and a second prosthetic device 1900b is implanted around the anterior leaflet 6 via the second rail 802b, as shown in FIG. 56B. Each of prosthetic devices 1900a, 1900b can be an expandable braided structure, such as described above and shown in FIGS. 32-33 and 46.

Figure 56E:
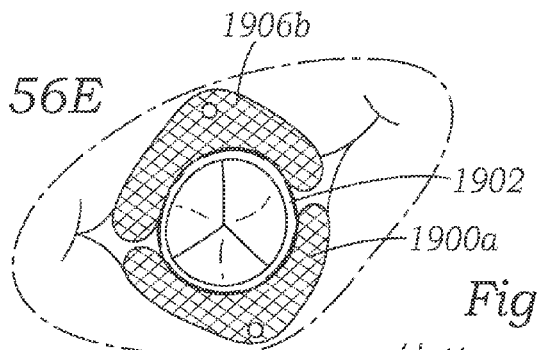
Figure 56C:
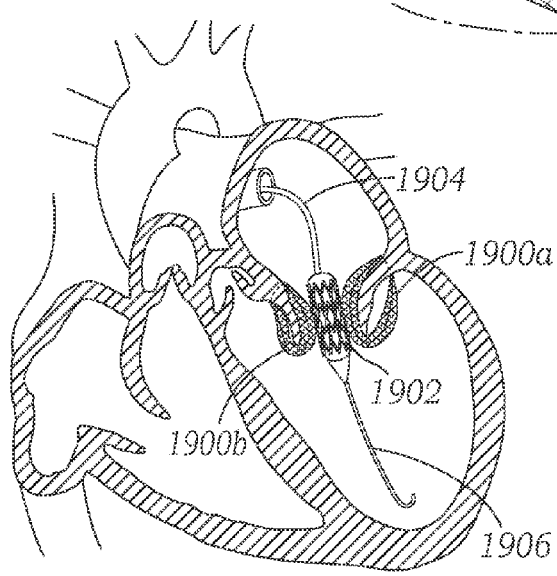
Figure 56D:
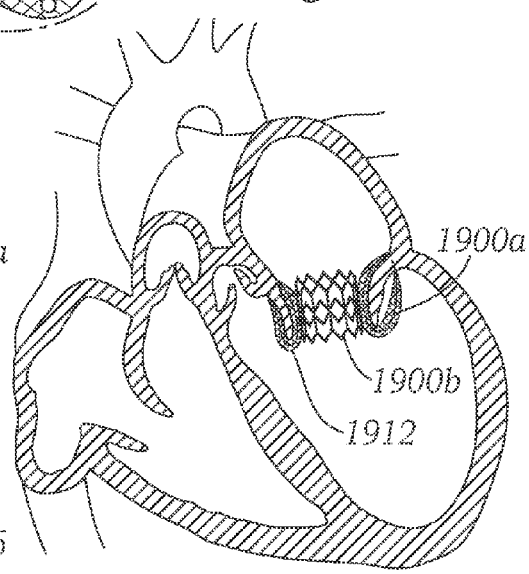

As shown in FIG. 56C, a prosthetic heart valve 1902 can be delivered to a position between prosthetic devices 1900a, 1900b via a delivery catheter 1904 that can be advanced over a guidewire 1906. The prosthetic heart valve 1902 can then be radially expanded to its functional size and held in place against the prosthetic devices 1900a, 1900b, as shown in FIGS. 56D and 56E. As shown in FIG. 56E, each of the prosthetic devices 1900a, 1900b can be sized and shaped to circumscribe about half of the outer surface of the prosthetic valve 1902 (about 180 degrees) such that collectively, the prosthetic devices 1900a, 1900b extend all the way around, or substantially all the way around the prosthetic valve. In other embodiments, more than two prosthetic devices can be implanted on the native leaflets for use as support structure for the prosthetic valve. For example, two or three such prosthetic devices can be implanted on one or both native leaflets for use as support structure. In another embodiment, a single prosthetic device can bridge or extend across one of the commissures of the mitral valve such that the single prosthetic device is implanted at least partially on both native leaflets.

Figure 57A:
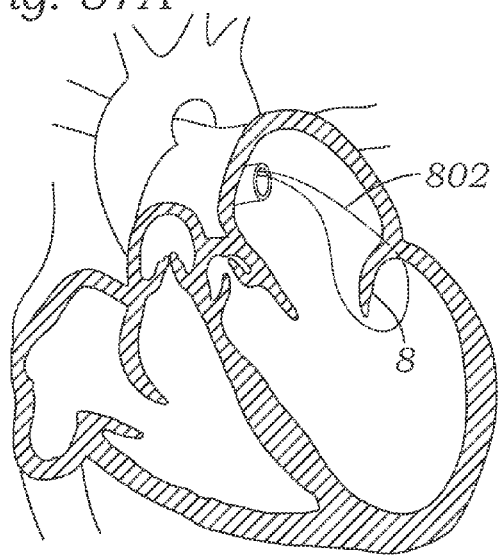
FIGS. 57A-57D show another method for implanting a prosthetic heart valve in the mitral position using a rail extending through one of the native leaflets as a support structure for the prosthetic valve.
Figure 57B:
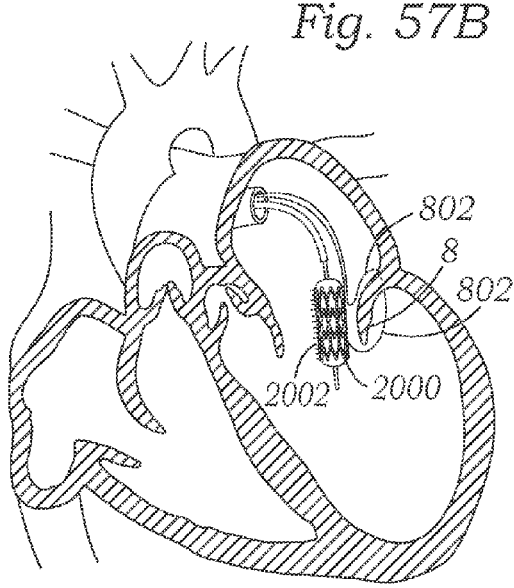
Figure 57C:
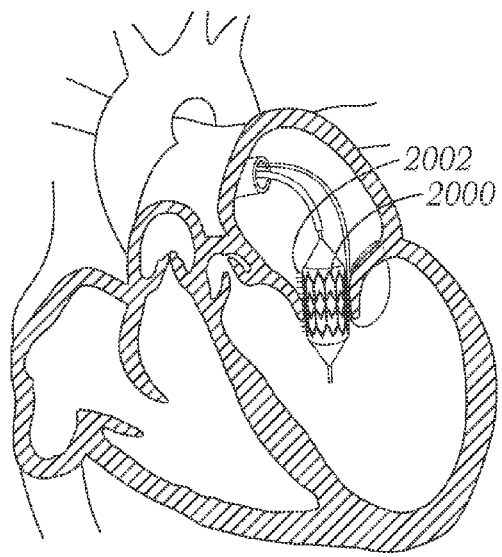
Figure 57D:
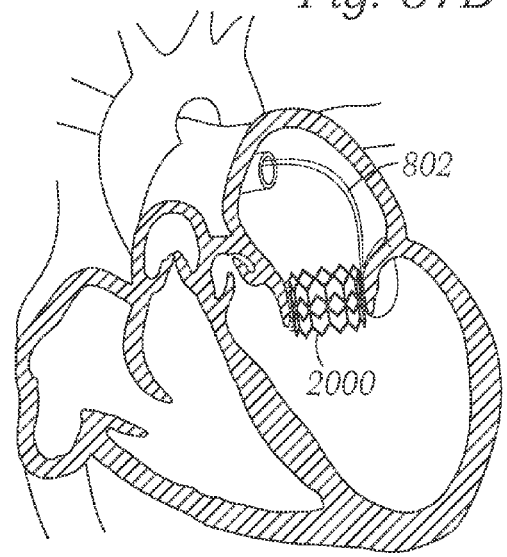

FIGS. 57A-57D show the use of a rail 802 alone as a support structure for a prosthetic heart valve. In the embodiment shown, the rail 802 is implanted through the posterior leaflet 8. For this application, the rail 802 desirably comprises a relatively stiffer material, such as a metal wire. As shown in FIGS. 57B-57C, a prosthetic heart valve 2000 is deployed between the native leaflets 6, 8 but bears against the rail 802 to help secure the prosthetic valve in place. The prosthetic valve 2002 can have a plurality of barbs or tissue engaging members 2002 that can engage the anterior leaflet or other to enhance frictional engagement of the prosthetic valve with native tissue. In alternative embodiments, a separate rail can be implanted through the anterior leaflet 6, or multiple rails can be implanted through one or both leaflets for use as support structure for a prosthetic valve.

FIGS. 58A-58E show another embodiment of a method for implanting a prosthetic heart valve in the mitral position using a prosthetic device mounted on one of the native leaflets as a support structure for the prosthetic valve. In this embodiment, a rail 802 is implanted through a posterior leaflet 8, and a prosthetic support device 2100 is implanted on the posterior leaflet via the rail as previously described. The support device 2100 can be an expandable braided structure, such as described above and shown in FIGS. 32-33 and 46.

Figure 58A:
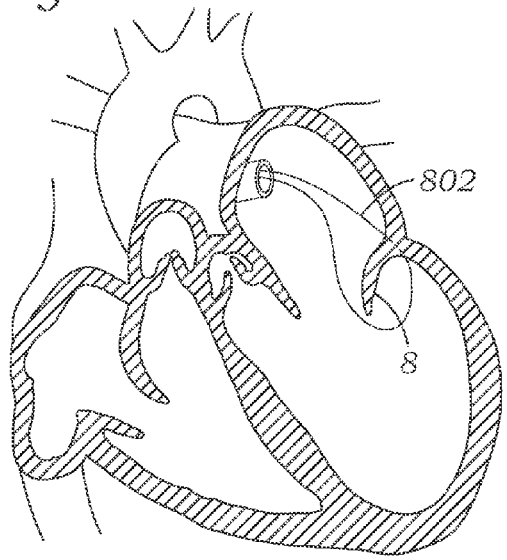
FIGS. 58A-58E show another method for implanting a prosthetic heart valve in the mitral position using a prosthetic device mounted on one of the native leaflets as a support structure for the prosthetic valve.
Figure 58B:
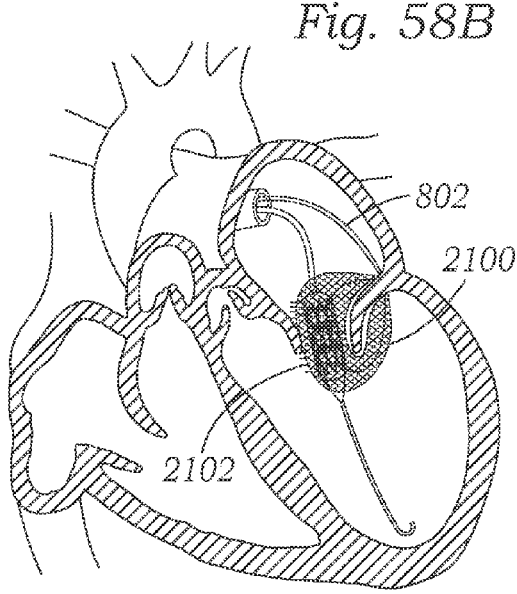
Figure 58E:
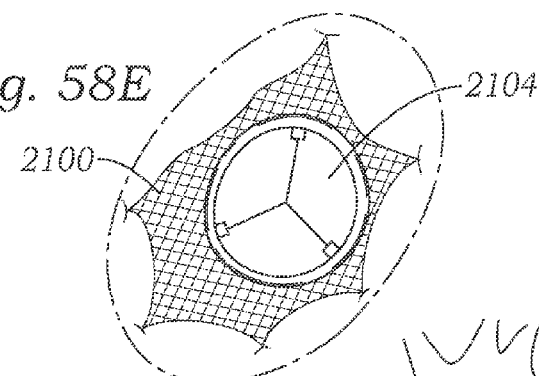
Figure 58C:
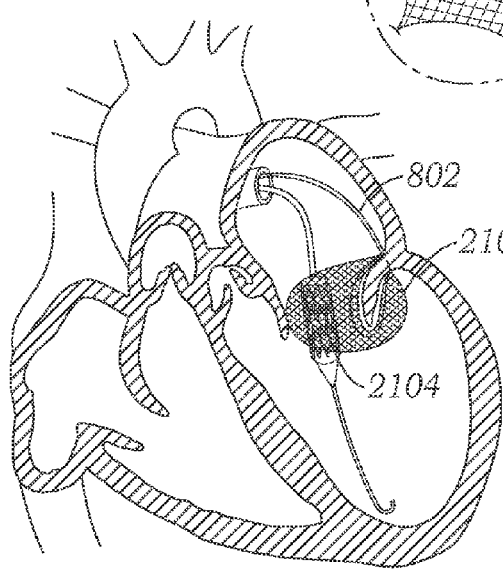
Figure 58D:
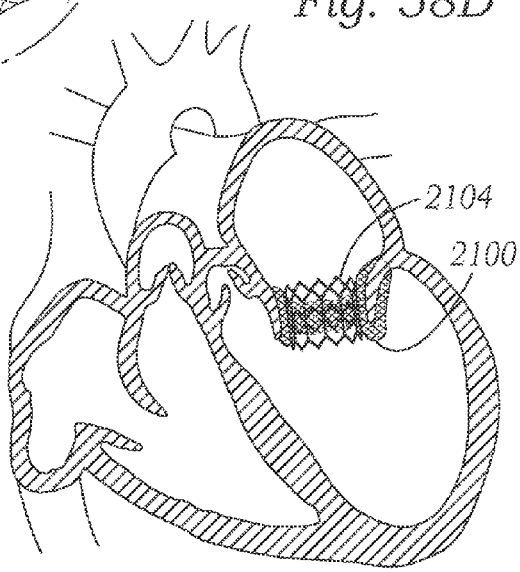

The support device 2100 can have barbs or tissue engaging members 2102 to enhance frictional engagement of the support device with adjacent tissue. The support device 2100 can further comprise a lumen that extends through the braided body of the support device in a direction from the left atrium towards the left ventricle. The lumen is sized to receive a prosthetic heart valve 2104, which can be expanded to its functional size within the lumen, as shown in FIGS. 58D and 58E.

FIG. 59 shows a prosthetic device 2200 for treating valve regurgitation, according to another embodiment. The prosthetic device 2200 can have an overall construction similar to the prosthetic device 1300 of FIGS. 32-33 and therefore can have an elongated body 2202 and first and second opposing end portions, or end caps, 2204, 2206, respectively at opposite ends of the body. One or both of the first and second end portions 2204, 2206 can have one or more barbs 2208 that can provide enhanced frictional engagement with the native leaflet. In the illustrated embodiment, each of the first and second end portions 2204, 2206 has a plurality of barbs 2208, with the barbs of the first end portion being offset from the barbs of the second end portion. In this way, the barbs of one end portion can mesh or nest within the barbs of the other end portion with a native leaflet therebetween.

The prosthetic device 2200 further includes a biasing member 2210 that is configured to move and retain the prosthetic device 2200 to a curled configuration around a native leaflet 8. In the illustrated embodiment, the biasing member 2210 extends through the body 2202 and has a first end secured to the first end portion 2204 and a second end secured to the second end portion 2206. The biasing member 2210 can comprise, for example, a leaf spring or resilient piece of metal or wire that is biased toward the curled configuration shown in FIG. 59. The biasing member 2210 can be made of Nitinol, stainless steel, or other flexible and resilient materials.

The biasing force applied by the biasing member 2210 on the end portions 2204, 2206 of the prosthetic device causes the end portions to bear against the tissue of the native leaflet and clamp the native leaflet therebetween. In particular embodiments, the biasing force of the biasing member 2210 is sufficient to retain the prosthetic device on the native leaflet without an additional securing mechanism extending through the leaflet (e.g., such as a suture). Thus, in such embodiments, the prosthetic device 2200 can be delivered and implanted on a native leaflet without the use of rail extending through the leaflet. Alternatively, the prosthetic device can be delivered to the native leaflet along a rail, which can then be completely removed from the body and not used to help secure the prosthetic device in place.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method comprising:
   implanting a flexible rail in the heart of a patient's body such that the rail forms a loop that extends through a leaflet of the native heart valve and first and second ends of the rail reside outside of the patient's body;
   coupling a prosthetic device to the rail and delivering the prosthetic device to the native leaflet via the rail, the prosthetic device comprising an elongate main body including a first end portion and a second end portion; and
   securing the prosthetic device to the native leaflet such that the first end portion is positioned against an atrial surface of the native leaflet and the second end portion is positioned against a ventricular surface of the native leaflet, and such that the main body extends around a free end portion of the native leaflet from the atrial surface to the ventricular surface so that the prosthetic device can coapt with and move away from an opposing native leaflet during operation of the heart valve.

2. The method of claim 1, wherein delivering the prosthetic device to the native leaflet comprises advancing the prosthetic device along the rail to the native leaflet.

3. The method of claim 1, wherein coupling the prosthetic device to the rail and delivering the prosthetic device to the native leaflet via the rail comprises securing the first end of the rail to the prosthetic device and retracting the second end of the rail such that the prosthetic device is pulled through the patient's body to the native leaflet.

4. The method of claim 1, wherein coupling the prosthetic device to the rail and delivering the prosthetic device to the native leaflet via the rail comprises securing the first end of the rail to the first end portion of the prosthetic device, inserting the second end of the rail through the second end portion of the prosthetic device, and advancing the prosthetic device along the rail to the native leaflet.

5. The method of claim 1, wherein coupling the prosthetic device to the rail and delivering the prosthetic device to the native leaflet via the rail comprises placing the prosthetic device on the rail such that the rail extends into the first end portion of the prosthetic device, through a lumen extending lengthwise through the main body of the prosthetic device, and outwardly from the second end portion of the prosthetic device, and then sliding the prosthetic device along the rail to the native leaflet.

6. The method of claim 1, wherein securing the prosthetic device to the native leaflet comprises securing a fastener on the rail adjacent the native leaflet.

7. The method of claim 1, wherein after delivering the prosthetic device to the native leaflet via the rail, tensioning the rail to cause lateral expansion of the prosthetic device.

8. The method of claim 1, wherein delivering the prosthetic device to the native leaflet via the rail comprises coupling the prosthetic device to a catheter, and advancing the catheter along the rail to advance the prosthetic device along the rail into the heart.

9. The method of claim 8, further comprising deploying a fastener from the catheter onto the rail at a location adjacent the native leaflet such that the prosthetic device is secured to the native leaflet by the rail and the fastener.

10. The method of claim 9, further comprising severing the rail adjacent the fastener such that a severed portion of the rail remains in the native leaflet with the fastener secured to the severed portion of the rail.

11. The method of claim 1, wherein the rail comprises a suture.

12. The method of claim 1, wherein the securing step further comprises securing the prosthetic device to the native leaflet such that the first end portion covers the atrial side of the native leaflet and the second end portion covers the ventricular side of the native leaflet.

\* \* \* \* \*